US008492357B2

(12) United States Patent
Worm et al.

(10) Patent No.: US 8,492,357 B2
(45) Date of Patent: *Jul. 23, 2013

(54) MICRO-RNA MEDIATED MODULATION OF COLONY STIMULATING FACTORS

(75) Inventors: Jesper Worm, Copenhagen (DK); Jan Stenvang, Copenhagen (DK); Susanna Obad, Malmö (SE); Sakari Kauppinen, Smørum (DK)

(73) Assignee: Santaris Pharma A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/057,146

(22) PCT Filed: Jul. 24, 2009

(86) PCT No.: PCT/EP2009/059608
§ 371 (c)(1),
(2), (4) Date: Apr. 28, 2011

(87) PCT Pub. No.: WO2010/012667
PCT Pub. Date: Feb. 4, 2010

(65) Prior Publication Data
US 2012/0115924 A1 May 10, 2012

Related U.S. Application Data

(60) Provisional application No. 61/085,644, filed on Aug. 1, 2008, provisional application No. 61/121,204, filed on Dec. 10, 2008.

(51) Int. Cl.
*A61K 48/00* (2006.01)
(52) U.S. Cl.
USPC ......... 514/44; 536/24.5; 536/24.31; 536/24.1
(58) Field of Classification Search
None
See application file for complete search history.

(56) References Cited

U.S. PATENT DOCUMENTS

| 4,914,210 A | 4/1990 | Levenson et al. |
| 4,920,115 A | 4/1990 | Nestler et al. |
| 4,962,029 A | 10/1990 | Levenson et al. |
| 5,919,795 A | 7/1999 | Chang et al. |
| 6,030,785 A | 2/2000 | Katze et al. |
| 6,121,283 A | 9/2000 | Chang et al. |
| 6,284,458 B1 | 9/2001 | Anderson et al. |
| 6,423,489 B1 | 7/2002 | Anderson et al. |
| 6,433,159 B1 | 8/2002 | Anderson et al. |
| 7,087,229 B2 | 8/2006 | Zhao et al. |
| 7,307,067 B2 | 12/2007 | Sarnow et al. |
| 7,683,036 B2 * | 3/2010 | Esau et al. .................. 514/44 R |
| 8,163,708 B2 | 4/2012 | Elmen et al. |
| 2003/0068320 A1 | 4/2003 | Dingivan |
| 2004/0204356 A1 | 10/2004 | Guenzler-Pukall et al. |
| 2005/0069522 A1 | 3/2005 | Colonno et al. |
| 2005/0182005 A1 | 8/2005 | Tuschl et al. |
| 2005/0227934 A1 | 10/2005 | Stoffel et al. |
| 2005/0261218 A1 | 11/2005 | Esau et al. |
| 2006/0035212 A1 | 2/2006 | Balakireva |
| 2006/0035858 A1 | 2/2006 | Geary et al. |
| 2006/0040989 A1 | 2/2006 | Meerpoel et al. |
| 2006/0058266 A1 | 3/2006 | Manoharan et al. |
| 2006/0185027 A1 | 8/2006 | Bartel et al. |
| 2006/0265771 A1 | 11/2006 | Lewis et al. |
| 2007/0049547 A1 | 3/2007 | Esau et al. |
| 2009/0082297 A1 | 3/2009 | Lioy et al. |
| 2009/0143326 A1 | 6/2009 | Obad et al. |
| 2009/0298916 A1 | 12/2009 | Kauppinen et al. |
| 2010/0004320 A1 | 1/2010 | Elmen et al. |
| 2010/0280099 A1 | 11/2010 | Elmen et al. |
| 2010/0286234 A1 | 11/2010 | Elmen et al. |
| 2010/0298410 A1 | 11/2010 | Obad et al. |
| 2010/0330035 A1 | 12/2010 | Hildebrandt-Eriksen et al. |
| 2011/0077288 A1 | 3/2011 | Kauppinen et al. |
| 2012/0083596 A1 | 4/2012 | Elmen et al. |

FOREIGN PATENT DOCUMENTS

| EP | 0 699 751 A1 | 3/1996 |
| EP | 1 099 442 A2 | 5/2001 |
| EP | 0 662 157 B1 | 6/2001 |
| EP | 1 222 309 B1 | 7/2005 |
| EP | 1747023 B1 | 1/2011 |
| EP | 1931782 B1 | 1/2011 |
| WO | WO 95/30746 A1 | 11/1995 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 02/28875 A2 | 4/2002 |
| WO | WO02/081494 A1 | 10/2002 |
| WO | WO 02/094250 A2 | 11/2002 |
| WO | WO 03/006475 A2 | 1/2003 |
| WO | WO 03/011887 A2 | 2/2003 |
| WO | WO 03/029459 A2 | 4/2003 |

(Continued)

OTHER PUBLICATIONS

Kluiver et al. Journal of Pathology 2005; 207:243-249.*
Abelson, J., et al., "Sequence Variants in *SLITRK1* Are Associated with Tourette's Syndrome," *Science* 310:317-320, American Assn. for the Advancement of Science, United States (2005).
Agrawal, S. and Zhao, Q., "Antisense therapeutics," Curr. Opin. Chem. Biol. 2:519-528, Elsevier, United Kingdom (1998).
Agrawal, S., et al, "Mixed-backbone oligonucleotides: as second generation antisense oligonucleotides: In vitro and in vivo studies", Proc. Natl. Acad. Sci. USA, vol. 94, pp. 2620-2625, National Academy of Sciences, United States (1997).
Agrawal, S. et al, "Pharmacokinetics, biodistribution, and stability of oligodeoxynucleotide phosphorothioates in mice", Proc. Natl. Acad. Sci. USA 88:7595-7599, National Academy of Sciences, United States (1991).

(Continued)

*Primary Examiner* — Kimberly Chong
(74) *Attorney, Agent, or Firm* — Sterne, Kessler, Goldstein & Fox P.L.L.C.

(57) ABSTRACT

The present invention relates to the modulation of immuno-regulatory proteins, including cytokines, such as colony stimulatory factors (CSF) via the use of microRNA-155 modulators.

16 Claims, 15 Drawing Sheets

FOREIGN PATENT DOCUMENTS

| | | |
|---|---|---|
| WO | WO 03/070750 A2 | 8/2003 |
| WO | WO 03/095467 A1 | 11/2003 |
| WO | WO 2004/044181 A2 | 5/2004 |
| WO | WO 2004/046160 A2 | 6/2004 |
| WO | WO 2004/069991 A2 | 8/2004 |
| WO | WO 2004/076622 A2 | 9/2004 |
| WO | WO 2005/013901 A2 | 2/2005 |
| WO | WO 2005/013905 A2 | 2/2005 |
| WO | WO 2005/023986 A2 | 3/2005 |
| WO | WO 2005/103298 A2 | 3/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/078139 A2 | 8/2005 |
| WO | WO 2005/079397 A2 | 9/2005 |
| WO | WO 2005/098029 A2 | 10/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/027776 A2 | 3/2006 |
| WO | WO 2006/036916 A2 | 4/2006 |
| WO | WO 2006/053430 A1 | 5/2006 |
| WO | WO 2006/069584 A2 | 7/2006 |
| WO | WO 2006/093526 A2 | 9/2006 |
| WO | WO 2006/112872 A2 | 10/2006 |
| WO | WO 2006/113910 A2 | 10/2006 |
| WO | WO 2006/133022 A2 | 12/2006 |
| WO | WO 2006/137941 A2 | 12/2006 |
| WO | WO 2007/021896 A2 | 2/2007 |
| WO | WO 2007/027775 A2 | 3/2007 |
| WO | WO 2007/027894 A2 | 3/2007 |
| WO | WO 2007/031081 A2 | 3/2007 |
| WO | WO 2007/031091 A2 | 3/2007 |
| WO | WO 2007/090073 A2 | 8/2007 |
| WO | WO 2007/112753 A2 | 10/2007 |
| WO | WO 2007/112754 A2 | 10/2007 |
| WO | WO 2007/134181 A2 | 11/2007 |
| WO | WO 2007/146511 A2 | 12/2007 |
| WO | WO 2008/025025 | 2/2008 |
| WO | WO 2008/034122 A2 | 3/2008 |
| WO | WO 2008/034123 A2 | 3/2008 |
| WO | WO 2008/046911 A2 | 4/2008 |
| WO | WO 2008/057234 A2 | 5/2008 |
| WO | WO 2008/061537 A2 | 5/2008 |
| WO | WO 2008/074328 A2 | 6/2008 |
| WO | WO 2008/091703 A2 | 7/2008 |
| WO | WO 2008/113832 A2 | 9/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |
| WO | WO 2009/043353 A2 | 4/2009 |
| WO | WO 2009/043354 A2 | 4/2009 |
| WO | WO 2009/109665 A1 | 9/2009 |
| WO | WO 2009/032083 A1 | 12/2009 |
| WO | WO 2010/000665 A1 | 1/2010 |
| WO | WO 2011/048125 A1 | 4/2011 |

OTHER PUBLICATIONS

Agrawal, S., "Importance of nucleotide sequence and chemical modifications antisense oligonucleotides" Biochimica et Biophysica Acta 1489:53-68, Elsevier Pub. Co., The Netherlands (1999).

Akhtar S., "Antisense Technology:Selection and delivery of optimally acting antisense oligonucleotides", Journal of Drug Targeting 5: 225-234, Informa Healthcare, United States (1998).

Alvarez-Garcia, I. and Miska, E., "MicroRNA functions in animal development and human disease," *Development* 132:4653-4662 The Company of Biologists, Ltd., United Kingdom (2005).

Ambros, V., "The functions of animal microRNAs," *Nature* 431:350-355, Nature Publishing Group, United Kingdom (2004).

Ameres, S.L., et al., "Molecular Basis Cell for Target RNA Recognition and Cleavage by Human RISC," Cell 130:101-112, Cell Press, United States (2007).

Asangani, I.A., et al., "MicroRNA-21 (miR-21) post-transcriptionally downregulates tumor supressor Pdcd4 and stimulates invasion, intravasation and metastasis in colorectal cancer," Oncogene 27:2128-2136, Nature Publishing Group, United Kingdom (2008).

Bai, S., et al., "MicroRNA-122 inhibits tumorigenic Properties of Hepatocellular Carcinoma Cells and Sensitizes These Cells to Sorafenib," J. Biol. Chem. 284(46):32015-32027, American Society for Biochemistry and Molecular Biology, United States (2009).

Bartel, D., "MicroRNAs: Genomics, Biogenesis, Mechanism, and Function," *Cell* 116:281-297, Cell Press, United States (2004).

Bartenschlager R. and Pietschmann T., "Efficient hepatitis C virus cell culture system: What a difference the host cell makes," Proc. Natl. Acad. Sci. 102:9739-9740, National Academy of Sciences, United States (2005).

Bartosch, B. et al., "Cell Entry of Hepatitis C Virus Requires a Set of Co-receptors That Include the CD81 Tetraspanin and the SR-B1 Scavenger Receptor," J. Biol. Chem. 278:41624-41630, American Society for Biochemistry and Molecular Biology, United States (2003).

Beaucage, L. and Iyer, R., "Advances in the Synthesis of Oligonucleotides by the Phosphoramidite Approach," *Tetrahedron* 48:2223-2311, Pergamon Press, United Kingdom (1993).

Beaucage, L. and Iyer, R., "The Synthesis of Modified Oligonucleotides by the Phosphoramidite Approach and Their Applications," *Tetrahedron* 49:6123-6194, Pergamon Press, United Kingdom (1993).

Bennett, C.F., "MicroRNAs as therapeutic targets," Abstracts of Papers, 234th ACS National Meeting, Boston, MA, United States, Aug. 19-23, 2007, CARB-047, Database: CAPLUS (2007).

Bennett, C., et al., "Antisense Oligonucleotide-based Therapeutics," Gene and Cell Therapy (2nd Edition), pp. 347-374, Editor: N S Templeton, Marcel Dekker, Inc. (2004).

Bhat, B., et al., "2'-O-Methoxyethyl/2'-Fluoro Modified Oligonucleotides Result in More Potent Inhibition of micro RNA-122 in Vivo: A Target Implicated in HCV Replication," *Nucleic Acids Symposium Series* 52:69, Oxford University Press, United Kingdom (2008).

Boehm, M., and Slack, F., "A Developmental Timing MicroRNA and Its Target Regulate Life Span in *C. elegans*," *Science* 310:1954-1957, American Assn. for the Advancement of Science, United States (2005).

Boutla, A., et al., "Developmental defects by antisense-mediated inactivation of micro-RNAs 2 and 13 in *Drosophila* and the identification of putative target genes," *Nucleic Acids Res.* 31:4973-4980, Oxford University Press, United Kingdom (2003).

Boutla, A., et al., "Short 5'-phosphorylated double-stranded RNAs induce RNA interference in *Drosophila*," *Curr. Biol.* 11:1776-1780, Cell Press, United States (2001).

Braasch, D., et al., "Antisense inhibition of gene expression in cells by oligonucleotides incorporating locked nucleic acids: effect of mRNA target sequence and chimera design," *Nucleic Acids Res.* 30:5160-5167, Oxford University Press, United Kingdom (2002).

Branch, A., and Rice, C., "Antisense Gets a Grip on miR-122 in Chimpanzees," *Sci. Transl. Med.* 2:1-4, American Assn. for the Advancement of Science, United States (2010).

Branch, A.D., A good antisense molecule is hard to find, TIBS 23:45-50, Elsevier Trends Journals, United Kingdom (1998).

Brennecke, J., et al., "*bantam* Encodes a Developmentally Regulated microRNA that Controls Cell Proliferation and Regulates the Proapoptotic Gene *hid* in *Drosophila*," *Cell* 113:25-36, Cell Press, United States (2003).

Brennecke. J., et al., "Principles of MicroRNA-Target Recognition," *PLoS Biology* 3:E85/0404-E85/0418, Public Library of Science, United States (2005).

Calin, G., et al., "Frequent deletions and down-regulation of micro-RNA genes *miR15* and *miR16* at 13q14 in chronic lymphocytic leukemia," *Proc. Natl. Acad. Sci. USA* 99:15524-15529. National Academy of Sciences, United States (2002).

Calin, G., et al., "Human microRNA genes are frequently located at fragile sites and genomic regions involved in cancers," *Proc. Natl. Acad. Sci. USA* 101:2999-3004, National Academy of Sciences, United States (2004).

Calin, G., et al., "A MicroRNA Signature Associated with Prognosis and Progression in Chronic Lymphocytic Leukemia," *N. Engl. J. Med.* 353:1793-1801, Massachusetts Medical Society, United States (2005).

Calin, G. and Croce, C., "MicroRNA signatures in human cancers," *Nat. Rev. Cancer* 6:857-866, Nature Publishing Group, United Kingdom (2006).

Chan, J., et al., "MicroRNA-21 Is an Antiapoptotic Factor in Human Glioblastoma Cells," *Cancer Res.* 65:6029-6033, American Association for Cancer Research, United States (2005).

Chang, J., et al., "Liver-Specific MicroRNA miR-122 Enhances the Replication of Hepatitis C Virus in Nonhepatic Cells," *J. Virol.* 82(16):8215-8223, American Society for Microbiology, United States (2008).

Chang, J., et al., "miR-122, a Mammalian Liver-Specific microRNA, is Processed from *hcr* mRNA and May Downregulate the High Affinity Cationic Amino Acid Transporter CAT-1," *RNA Biol.* 1:106-113, Landes Bioscience, United States (2004).

Chen, X., "A MicroRNA as a Translational Repressor of *APETALA2* in *Arabidopsis* Development," *Science* 303:2022-2025, American Assn. for the Advancement of Science, United States (2004).

Chen, J.-F., et al., "The role of microRNA-1 and micro-RNA-133 in skeletal muscle differentiation," *Nat. Genet.* 38:228-233, Nature Publishing Co., United States (2005).

Cheng, A., et al., "Antisense inhibition of human miRNAs and indications for an involvement miRNA in cell growth and apoptosis," *Nucleic Acids Res.* 33:1290-1297, Oxford University Press, United Kingdom (2005).

Choi, W.-Y., et al., "Target Protectors Reveal Dampening and Balancing of Nodal Agonist and Antagonist by miR-430," Science DOI:10.1126/science.1147535, American Assn. for the Advancement of Science, United States (2007).

Christensen, U. and Pedersen, E., "Intercalating nucleic acids containing insertions of 1-*O*-(1-pyrenylmethyl)glycerol: stabilisation of dsDNA and discrimination of DNA over RNA," *Nucleic Acids Res.* 30:4918-4925, Oxford University Press, United Kingdom (2002).

Connolly E. et al., "Elevated Expression of the miR-17-92 Polycistron and miR-21 in Hepadnavirus-Associated Hepatocellular Carcinoma Contributes to the Malignant Phenotype," Am. J. Pathol. 173(3):856-864, American Society for Investigative Pathology (2008).

Cook, P.D., "Antisense Medicinal Chemistry", In Antisense Research & Application, Edited by Stanley Crooke p. 51-101 (1998).

Corsten, M., et al., "MicroRNA-21 Knockdown Disrupts Glioma Growth In vivo and Displays Synergistic Cytotoxicity with Neural Precursor Cell-Delivered S-TRAIL in Human Gliomas," *Cancer Res.* 67:8994-9000, American Association for Cancer Research, United States (2007).

Coulouarn, C., et al., "Loss of miR-122 expression in liver cancer correlates with suppression of the hepatic phenotype and gain of metastatic properties," Oncogene 28:3526-36, Nature Publishing Group, United Kingdom (2009).

Crooke, R., "Chapter 3: In Vitro Cellular Uptake, Distribution, and Metabolism of Oligonucleotides," in *Antisense Research and Application* 131:103-140, Springer-Verlag, Germany (1998).

Crooke, S.T., "Mechanisms of Antisense Drug Action, an Introduction" in Antisense Technology, Principles, Strategies and Applications, Ed. Crooke S.T. p. 3-46 (2008).

Crooke, S.T., "An overview of Progress in Antisense Therapeutics", Antisense & Nucleic Acid Drug Development 8:115-122, Mary Ann Liebert, Inc., United States (1998).

Crooke S.T., "Basic Principles of Antisense Technology", in Antisense Drug Technology, Principles, Strategies and Applications, Ed. Crooke S.T. p. 1-28 (2001).

Czech, M., "MicroRNAs as Therapeutic Targets," *N. Engl. J. Med.* 354:1194-1195, Massachusetts Medical Society, United States (2006).

Dass, C., "Vehicles for oligonucleotide delivery to tumours," *J. Pharm. Pharmacol.* 54:3-27 Pharmaceutical Press, United Kingdom (2002).

Davidson, N. and Shelness, G., "Apolipoprotein B: mRNA Editing, Lipoprotein Assembly, and Presecretory Degradation," *Annu. Rev. Nutr.* 20:169-193, Annual Reviews, United States (2000).

Davis, S., et al., "Improved targeting of miRNA with antisense oligonucleotides," *Nucleic Acids Res.* 34:2294-2304, Oxford University Press, United Kingdom (2006).

Davis, S., et al., "Potent inhibition of microRNA in vivo without degradation," *Nucleic Acids Res.* 37:70-77, Oxford University Press, United Kingdom (2008).

Davis, S., et al., "Potent inhibition of microRNA in vivo without degradation," *Nucleic Acids Res.* 37:70-77, Oxford University Press, United Kingdom (2008) [Supplementary data].

Deere, J., et al., "Antisense Phosphorodiamidate Morpholino Oligomer Length and Target Position Effects on Gene-Specific Inhibition in *Escherichia coli,*" *Antimicrobial Agents and Chemotherapy* 49:249-255, American Society for Microbiology, United States (2005).

D Young & Co., Investigation of teachings of WO2008/061537 and WO2008/151639, Jan. 2009.

Diaz-Toledano, R., et al., "In vitro characterization of a miR-122-sensitive double-helical switch element in the 5' region of hepatitis C virus RNA," Nucl. Acids. Res. 37(16):5498-5510, : Oxford University Press, United Kingdom (2009).

Eis, P., et al., "Accumulation of miR-155 and *BIC* RNA in human B cell lymphomas," *Proc. Natl. Acad. Sci. USA* 102: 3627-3632, National Academy of Sciences, United States (2005).

Eisenberg, I., et al., "Distinctive patterns microRNA expression in primary muscular disorders." *Proc. Natl. Acad. Sci. USA* 104:17016-17021, National Academy of Sciences, United States (2007).

Elbashir, S., et al., "Analysis of gene function in somatic mammalian cells using small interfering RNAs," *Methods* 26:199-213, Academic Press, United States (2002).

Elmén, J., et al., "Locked nucleic acid containing antisense oligonucleotides enhance inhibition of HIV-1 genome dimerization and inhibit virus replication," *FEBS Letters* 578:285-290, Elsevier B.V., The Netherlands (2004).

Elmén, J., et al., "Antagonism of microRNA-122 in mice systematically administered LNA-antimiR leads to up-regulation of a large set of predicted target mRNAs in the liver," *Nucleic Acids Res.* 36:1-10, Oxford University Press, United Kingdom (2007).

Elmén, J., et al., "LNA-antimiRs: Promising candidates for therapeutic intervention of disease-related microRNAs," [poster] 71st Symposium on Quantitative Biology; Regulatory RNAs, Cold Spring Harbor, New York, United States (May 2006).

Elmén, J., et al., "LNA-antimiRs: Promising candidates for therapeutic intervention of disease-related microRNAs," [presentation abstract] 71st Symposium on Quantitative Biology; Regulatory RNAs, Cold Spring Harbor, New York, United States (May 2006).

Elmén, J., et al., "LNA-antimiRs: Promising candidates for therapeutic intervention of disease-related microRNAs," [conference abstract] Nov. 1-2, 2006, MicroRNAs: Biology to Development and Disease. Peterhouse, University of Cambridge, UK (2006).

Elmén, J., et al., "LNA-mediated microRNA silencing in non-human primates," *Nature* 452:896-900, Nature Publishing Group, United Kingdom (2008).

Esau, C., "MicroRNA-143 Regulates Adipocyte Differentiation," *J. Biol. Chem.* 279:52361-52365, American Society for Biochemistry and Molecular Biology, United States (2004).

Esau, C., "MicroRNA-143 Regulates Adipocyte Differentiation [Supplementary Methods]," *J. Biol. Chem.* 279, 25 pages, American Society for Biochemistry and Molecular Biology, United States (2004).

Esau, C., et al., "Identification of microRNAs involved in adipocyte development using second-generation antisense oligonucleotides in an in vitro adipocyte differentiation model," [poster abstract] siRNAs and miRNAs Keystone Symposium, Keystone Resort, Colorado United States (2004).

Esau, C., et al., "miR-122 regulation of lipid metabolism revealed by in vivo antisense targeting," *Cell Metab.* 3:87-98, Cell Press, United States (2006).

Esau, C., et al., "miR-122 regulation of lipid metabolism revealed by in vivo antisense targeting," [Supplemental data] *Cell Metab.* 3, 1 page, Cell Press, United States (2006).

Esau, C.C., and Monia, B.P., "Therapeutic potential for microRNAs," *Adv. Drug Deliv. Rev.* 59:101-114, Elsevier Science Publishers, B.V., The Netherlands (2007).

Esau, C., "Inhibition of mocroRNA with antisense oligonucleotides," *Methods* 44:55-60, Academic Press, United States (2008).

Esquela-Kerscher, A. and Slack, F., "Oncomirs—microRNAs with a role in cancer," *Nat. Rev. Cancer* 6:259-269, Nature Publishing Group, United Kingdom (2006).

Fabani, M., and Gait, M., "miR-122 targeting with LNA/2'-*O*-methyl oligonucleotide mixmers, peptide nucleic acids (PNA), and PNA-peptide conjugates," *RNA* 14:336-346, Cold Spring Harbor Laboratory Press, United States (2008).

U.S. Department of Health and Human Services, Food and Drug Administration, Center for Drug Evaluation and Research (CDER), "Guidance for Industry Antiviral Product Development—Conducting and Submitting Virology Studies to the Agency," Jun. 2006, Clinical Antimicrobial (2006).

Feld, J., et al., "Ribavirin Improves Early Response to PEG-interferon Through Improved Interferon Signaling," *Gastroenterology* 139:154-162, W.B. Saunders, United States (2010).

Feld, J.J, and Hoofnagle, J. H., "Mechanism of action of interferon and ribavirin in treatment of hepatitis C", Nature 436: 967-72, Nature Publishing Group, United Kingdom (2005).

Fluiter, K. et al., "In vivo tumor growth inhibition and biodistribution studies of locked nucleic acid (LNA) antisense oligonucleotides," Nucleic Acids Res. 31(3):953-962, Oxford University Press, United Kingdom (2003).

Fornari, F., et al., "MiR-122/Cyclin G1 Interaction Modulates p53 Activity and Affects Doxorubicin Sensitivity of Human Hepatocarcinoma Cells," *Cancer Res.* 69(14):5761-5767, American Assn. for Cancer Research, United States (2009).

Frankel, L.B., et al., "Programmed cell death 4 (PDCD4) is an important functional target of the microRNA miR-21 in breast cancer cells." J. Biol. Chem. 283:1026-1033, The American Society for Biochemistry and Molecular Biology, United States (2008).

Freier, S. and Altmann, K.-H., "The ups and downs of nucleic acid duplex stability: structure-stability studies on chemically-modified DNA: RNA duplexes," *Nucleic Acids Res.* 25:4429-4443, Oxford University Press, United Kingdom (1997).

Freier, S.M., "Methods of Selecting Sites in RNA for Antisense Targeting," *Antisense Drug Technology,* Edited by Stanley T. Crooke, CRC Press, ISBN: 978-0-8247-0566-4 (2001).

Frieden, M., et al., "Expanding the design horizon of antisense oligonucleotides with alpha-L-LNA," *Nucleic Acids Res.* 31:6365-6372, Oxford University Press, United Kingdom (2003).

Frieden, M. and Ørum, H. "Locked Nucleic Acid Holds Promise in the Treatment of Cancer," *Curr. Pharmac. Design* 14:1138-1142, Bentham Science Publishers, The Netherlands (2008).

Gabriely, G., et al., "MicroRNA 21 Promotes Glioma Invasion by Targeting Matrix Metalloproteinase Regulators," *Molec. Cell. Biol.* 28(17):5369-5380, American Society for Microbiology, United States (2008).

Galardi, S., et al., "miR-221 and miR-222 expression affects the proliferation potential of human prostate carcinoma cell lines by targeting p27Kip1" J. Biol. Chem. 282:23716-23724, The American Society for Biochemistry and Molecular Biology, United States (2007).

Geary, R.S., et al., "Pharmacokinetic Properties of 29-O-(2-Methoxyethyl)-Modified Oligonucleotide Analogs in Rats," *J. Pharm. Exper. Therap.* 296(3):890-897, American Society for Pharmacology and Experimental Therapeutics, United States (2001).

Gentleman, R., et al., "Bioconductor: open software development for computational biology and bioinformatics," *Genome Biol.* 5:R80, BioMed Central Ltd., United Kingdom (2004).

Gerwitz, A.M., "Nucleic Acid Therapeutics: State of the art and future prospects", Blood 92:712-736, American Society of Hematology, United States (1998).

Giles, R., et al., "Selecting optimal oligonucleotide composition for maximal antisense effect following streptolysin O-mediated delivery into human leukaemia cells," *Nucleic Acid Res.* 26:1567-1575, Oxford University Press, United Kingdom (1998).

Giraldez, A., et al., "MicroRNAs Regulate Brain Morphogenesis in Zebrafish," *Science* 308: 833-838, American Assn. for the Advancement of Science, United States (2005).

Girard M. et al., "miR-122, a paradigm for the role of microRNAs in the liver," *J. Hepatol.* 48:648-656 (2008).

Gramantieri, L., et al., "Cyclin G1 is a Target of miR-122a, a MicroRNA Frequently Down-regulated in Human Hepatocellular Carcinoma," *Cancer Res.* 64(13):6092-6099, American Assn. Cancer Research, United States (2007).

Greene, T. and Wuts, P., *Protective Groups in Groups in Organic Synthesis,* [Table of Contents], 3rd ed., John Wiley & Sons, Chichester, England (1999).

Griffiths-Jones, S., "The microRNA Registry," *Nucleic Acids Res.* 32:D109-D111 (Database Issue), Oxford University Press, United Kingdom (2004).

Griffiths-Jones, S., et al., "miRBase: microRNA sequences, targets and gene nomenclature," *Nucleic Acids Res.* 34:D140-D144 (Database issue), Oxford University Press, United Kingdom (2006).

Grimm, D. and Kay, M.A., "Therapeutic application of RNAi: is mRNA targeting finally ready for prime time?" J. Clinic. Invest. 117(12):3633-3641, American Society for Clinical Investigation, United States (2007).

Grimson, A., et al., "MicroRNA Targeting Specificity in Mammals: Determinants beyond Seed Pairing," *Mol. Cell.* 27:91-105, Elsevier, Inc., The Netherlands (2007).

Hanecak, R., et al., "Antisense Oligonucleotide Inhibition of Hepatitis C Virus Gene Expression in Transformed Hepatocytes," *J. Virol.* 70:5203-5212, American Society For Microbiology, United States (1996).

Haussecker, D. and Kay, M., "miR-122 Continues to Blaze the Trail for MicroRNA Therapeutics," *Molecular Therapy* 18:240-242, Nature Publishing Group, United States (2010).

He, L., et al., "A microRNA polycistron as a potential human oncogene," *Nature* 435:828-833, Nature Publishing Group, United Kingdom (2005).

Heid, C., et al., "Real Time Quantitative PCR," *Genome Res.* 6:986-994, Cold Spring Harbor Laboratory Press, United States (1996).

Henke, J. I., et al., "microRNA-122 stimulates translation of hepatitis C virus RNA," *EMBO Journal* 27:3300-3310, Nature Pub. Group, United Kingdom (2008).

Hildebrandt-Eriksen, E.S., et al., "A unique Therapy for HCV Inhibits mocroRNA-122 in Humans and Results in HCV Suppression in Chronically Infected Chimpanzees: Results from Primate and First-in-Human Studies," *Hepatology* LB19, 50(6):12A, Wiley, United States (2009).

Hogrefe, R.I., "An antisense oligonucleotide primer", Antisense & Nucleic Acid Drug Development 9:351-357, Mary Ann Liebert, Inc., United States (1999).

Hornstein, E., et al., "The microRNA *miR-196* acts upstream of Hoxb8 and Shh in limb development," *Nature* 438:671-674, Nature Publishing Group, United Kingdom (2005).

Horwich, M.D. and Zamore, P. D., "Design and delivery of antisense oligonucleotides to block microRNA function in cultured *Drosophila* and human cells," Nature Protocols 3(10):1537-1549, Nature Pub. Group, United Kingdom (2008).

Hu, Q., "Subcellular trafficking of antisense oligonucleotides and down-regulation of *bcl-2 gene* expression in human melanoma cells using a fusogenic liposome delivery system," *Nucleic Acid Res.* 30:3632-3641, Oxford University Press, United Kingdom (2002).

Huang, H., et al., "Hepatitis C virus production by human hepatocytes dependent on assembly and secretion of very low-density lipoproteins," *Proc. Natl. Acad. Sci. U.S.A.* 104:5848-5853, National Academy of Sciences, United States (2007).

Huber, W., et al., "Variance stabilization applied to microarray data calibration and to the quantification of differential expression," *Bioinformatics* 18:S96-S104, Oxford University Press, United Kingdom (2002).

Hutton, J., "Renaturation kinetics and thermal stability of DNA in aqueous solutions of formamide and urea," *Nucleic Acids Res.* 4:3537-3555, Oxford University Press, United Kingdom (1977).

Hutvágner, G., et al., "A Cellular Function for the RNA-Interference Enzyme Dicer in the Maturation of the *let-7* Small Temporal RNA," *Science* 293:834-838, American Assn. for the Advancement of Science, United States (2001).

Hutvágner, G., et al., "Sequence-Specific Inhibition of Small RNA Function," *PLoS Biology* 2:0465-0475, Public Library of Science, United States (2004).

Hutvagner, G., et al., "Sequence-specific inhibition of small RNA function," [Poster abstract] siRNAs and miRNAs Keystone Symposium, Keystone Resort, Colorado, United States, Apr. 14-Apr. 19, 2004, 1 page.

Hwang, H., et al., "Cell—cell contact globally activates microRNA biogenesis," *Proc. Natl. Acad. Sci.* 106:7016-7021, National Academy of Sciences, United States (2009).

Ikeda, M., et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," *J. Virol.* 76(6):2997-3006, American Society for Microbiology, United States (2002).

Iliopoulos, D., et al., "MicroRNA-370 controls the expression of MicroRNA-122 and Cpt1α and affects lipid metabolism," *J. Lipid. Res.* 51:1513-1523, American Society for Biochemistry and Molecular Biology, United States (2010).

Iorio, M., et al, "MicroRNA Gene Expression Deregulation in Human Breast Cancer," *Cancer Res.* 65:7065-7070, American Assn. for Cancer Research, United States (2005).

Ittig, D., et al., "Nuclear antisense effects in cyclophilin a pre-mRNA splicing by oligonucleotides: a comparison of tricyclo-DNA with LNA," *Nucleic Acids Res.* 32:346-353, Oxford University Press (2004).

Jackson, A. and Linsley, P., "The Therapeutic Potential of microRNA Modulation," discoverymedicine.com, at http://www.discoverymedicine.com/Aimee-Jackson/2010/04/10/the-therapeutic-potential-of-microrna-modulation/, accessed on May 5, 2010, 7 pages.

Jepsen, J., et al, "Locked Nucleic: A potential Nucleic Acid Analog in Therapeutics and Biotechnology," *Oligonucleotides* 14:130-146, Mary Ann Liebert, Inc., United States (2004).

Jepsen, J.S., and Wengel, J., "LNA-Antisense rivals siRNA forgene silencing." *Curr. Opin. Drug. Discov. Develop.* 7(2):1889-194, Thomson Reuters (Scientific) Ltd, United Kingdom (2004).

Jin, P., et al., "RNA and microRNAs in fragile X mental retardation," *Nat. Cell Biol.* 6:1048-1053, Nature Publishing Group, United States (2004).

Johansson, H., et al., "Target-specific arrest of mRNA translation by antisense 2'-O-alkyloligonucleotides," *Nucleic Acids Res.* 22: 4591-4598; Oxford University Press, United Kingdom (1994).

Johnson, C.D., et al., "The let-7 MicroRNA Represses Cell Proliferation Pathways in Human Cells," Cancer Research 67:7713-7722, American Association for Cancer Research, United States (2007).

Johnson, S., et al., "RAS is Regulated by the *let-7* MicroRNA Family," *Cell* 120:635-647, Cell Press, United States (2005).

Johnston, Jr., R., and Hobert, O., "A microRNA controlling left/right neuronal asymmetry in *Caenorhabditis elegans*," *Nature* 426:845-849, Nature Publishing Group, United Kingdom (2003).

Jopling, C., "Regulation of hepatitis C virus by microRNA-122," *Biochemical Society Transactions* 36:1220-1223, Portland Press, United Kingdom (2008).

Jopling, C., et al., "Liver-specific microRNA 122 Regulates Hepatitis C viral RNA Abundance," p. 124, Sarnow, P. Conference: Translational Control, Cold Spring Harbor Laboratory, Cold Spring Harbor, New York, United States, Sep. 7-12, 2004.

Jopling, C., et al., "Modulation of Hepatitis C Virus RNA Abundance by a Liver-Specific MicroRNA," *Science* 309:1577-1571, American Assn. for the Advancement of Science, United States (2005).

Jopling, C. L., et al., "Positive and negative Modulation of Viral and Cellular mRNAs by liver-specific MicroRNA miR-122," Cold Spring Harbor Symposia on Quantitative Biology (71):369-376 (2006).

Jopling, C. L., "Position-Dependent Function for a Tandem MicroRNA miR-122-Binding Site Located in the Hepatitis C Virus RNA Genome," Cell Host and Microbe 4:77-85, Cell Press, United States (2008).

Kauppinen, S., et al., "Locked nucleic acid (LNA): High affinity targeting of RNA for diagnostics and therapeutics," *Drug Discovery Today: Technologies* 2:287-290, Elsevier, Ltd., The Netherlands (2005).

Kauppinen, S., "Antagonizing microRNAs for therapeutics," Human Gene Therapy 19(10):1063, M.A. Liebert, United States (2008).

Kauppinen, S., et al., "Locked Nucleic Acid: High-Affinity Targeting of Complementary RNA for RNomics," Handbook of Experimental Pharmacology, Springer-Verlag Berlin Heidelberg 173:405-422 (2006).

Kaur, H., et al., "LNA-modified oligonucleotides effectively drive intramolecular-stable hairpin to intermolecular-duplex state," *Biochem. Biophys. Res. Comm.* 352:118-122, Academic Press, United States (2007).

Ketting, R., et al., "Dicer functions in RNA interference and in synthesis of small RNA involved in developmental timing in *C.elegans*," *Genes Dev.* 15:2654-2659, Cold Spring Harbor Laboratory Press, United States (2001).

Khan, AA et al., "Transfection of small RNAs globally perturbs gene regulation by endogenous microRNAs," A144:549-555, Nature Publishing Group, United States (2009).

Kinberger, G.A. et al., "Design, sythesis and in vivo reuslts of chemically-modified antisense oligonucleotides targeting microRNA-122", Abstracts of Papers 234th ACS Annual Meeting (2010).

Klein M E et al., "Homeostatic regulation of MeCP2 expression by a CREB-induced microRNA,"*Nat. Neurosci.* 10(12):1513-1514, Nature Publishing Group, United States (2007).

Kloosterman, W., et al., "Substrate requirements for *let-7* function in the developing zebrafish embryo," *Nucleic Acids Res.* 32:6284-6291, Oxford University Press, United Kingdom (2004).

Kloosterman, W. and Plasterk, R., "The Diverse Functions of MicroRNAs in Animal Development and Disease," *Dev. Cell* 11:441-450, Elsevier, Inc. The Netherlands (2006).

Kloosterman, W., et al., "In situ detection of miRNAs in animal embryos using LNA-modified oligonucleotide probe," *Nat. Methods* 3:27-29, Nature Publishing Group, United States (2006).

Kocerha, J., et al., "MicroRNA-219 modulates NMDA receptor-mediated neurobehavioral dysfunction," *Proc. Natl. Acad. Sci. USA* 106:3507-3512, National Academy of Sciences, United States (2008).

Kocerha, J. et al., "microRNAs in CNS Disorders", Neuromol. Med. 11:162-172, Humana Press, United States (2009).

Koch, T. and Ørum, H. "Locked Nucleic Acid", Drug Technology, Principles, Strategies and Applications, Ed. Crooke S.T. pp. 519-564 (2008).

Kock, T. et al., "Locked Nucleic Acid: Properties and Therapeutic Aspects", In Therapeutic Oligonucleotides (2008), 103-141. Editor(s) Kurreck, Jens. Publisher Royal Society of Chemistry, Cambridge, UK.

Krukemeyer, M., et al., "Description of B lymphocytes and plasma cells, complement, and chemokines/receptors in acute liver allograft rejection," *Transplantation* 78:65-70, Lippincott Williams & Wilkins, United States (2004).

Krützfeldt, J., et al., Silencing of microRNAs in vivo with 'antagomirs,' *Nature Letters* 438:685-689, Nature Publishing Group, United Kingdom (2005).

Krützfeldt, J., et al., Specificity, duplex degradation and subcellular localization of antagomirs, *Nucleic Acids Res.* 35:2885-2892, Oxford University Press, United Kingdom (2007).

Krützfeldt, J., et al., "Strategies to determine the biological function of microRNAs," *Nature Genetics* 38:S14-S19, Nature Publishing Group, United Kingdom (2006).

Kurreck, J., et al., "Design of antisense oligonucleotides stabilized by locked nucleic acids," *Nucleic Acids Res.* 30:1911-1918, Oxford University Press, United Kingdom (2002).

Kutay, H., et al., "Downregulation of miR-122 in the Rodent and Human Hepatocellular Carcinomas," *J. Cell. Biol.* 99:671-678, Wiley-Liss, United States (2006).

Kwon, C., et al., "MicroRNA1 influences cardiac differentiation in *Drosophila* and regulates Notch signaling," *Proc. Natl. Acad. Sci. USA* 102:18986-18991, National Academy of Sciences, Untied States (2005).

Lagos-Quintana, M., et al., "Identification of Tissue-Specific MicroRNAs from Mouse," *Curr. Biol.* 12:735-739, Elsevier Science Ltd., The Netherlands (2002).

Lagos-Quintana, M. et al., "Identification of Novel Genes Coding for Small Expressed RNAs", Science 294:853-858, American Assn. for the Advancement of Science, United States (2001).

Landthaler, M., et al., "The Human DiGeorge Syndrome Critical Region Gene 8 and Its *D. melanogaster* Homolog are Required for miRNA Biogenesis," *Curr. Biol.* 14:2162-2167, Elsevier Ltd., The Netherlands (2004).

Landthaler, M., et al., "Sequence-specific inhibition of microRNA and siRNA-induced RNA silencing" [poster abstract] siRNAs and miRNAs Keystone Symposium, Keystone Resort, Colorado United States (2004).

Lanford, R.E. et al., "Antagonizing MicroRNA-122 and Treatment of Hepatitis C Virus Infection", Hepatology 51:1461-1465, Wiley, United States (2010).

Lanford, R., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77:1092-1104, American Society for Microbiology, United States (2003).

Lanford, R., et al., "Lack of response to exogenous interferon-alpha in the liver of chimpanzees chronically infected with hepatitis C virus," *Hepatology* 46:999-1008, Wiley, United States (2007).

Lanford, R., et al., "Therapeutic Silencing of MicroRNA-122 in Primates with Chronic Hepatitis C Virus Infection," *Science* 327:198-201, American Assn. for the Advanncement of Science, United States (2010).

Lanford, R. E. et al., "The Accelerating Pace of HCV Research; A Summary of the 15th International Symposium on Hepatitis C Virus and Related Viruses", Gastroenterology 136: 9-16, W.B. Saunders, United States (2009).

Leaman, D., et al., "MiRNA function in *Drosophila* development," [poster abstract] siRNAs and miRNAs Keystone Symposium, Keystone Resort, Colorado, United States (2004).

Leaman, D., et al., "Antisense-Mediated Depletion Reveals Essential and Sepcific Functions of MicroRNAs in *Drosophila* Development,"*Cell* 121: 1097-1108, Cell Press, United States (2005).

Lecellier, C.-H., et al., "A Cellular MicroRNA Mediates Antiviral for the Defense in Human Cells," *Science* 308:557-560, American Assn. for the Advancement of Science, United States (2005).

Lecellier, C.-H., et al, "A Cellular MicroRNA Mediates Antiviral Defense in Human Cells," [Supporting online material] *Science* 308:557-560, American Assn. for the Advancement of Science, United States (2005).

Lee, Y.S. and Dutta, A. "The tumor suppressor microRNA let-7 represses the HMGA2 oncogene" A182:1025-1030, Cold Spring Harbor Laboratory Press, United States (2007).

Lee, Y., et al., "The nuclear RNase III Drosha initiates microRNA Processing," *Nature* 425:415-419, Nature Publishing Group, United Kingdom (2003).

Lee, Y., et al., "Depletion of Human Micro-RNA miR-125b Reveals That it is Critical for the Proliferation of Differentiated Cells but Not for the Down-reglation of Putative Targets during Differentiation," *J. Biol. Chem.* 280:16635-16641, The American Society for Biochemistry and Molecular Biology, Inc., United States (2005).

Le Sage, C., et al., "Regulation of the CDKN1B/p27 tumor suppressor by miR-221 and miR-222 promotes cancer cell proliferation" *Cell*6:3699-3708, Nature Publishing Group, United Kingdom (2007).

Lewis, B., et al., "Conserved Seed Pairing, Often Flanked by Adenosines, Indicates that Thousands of Human Genes are MicroRNA Targets," *Cell* 120:15-20, Elsevier, Inc., The Netherlands (2005).

Li, X. and Carthew, R., "A microRNA Mediates EGF Receptor Signaling and Promotes Photoreceptor Differentiation in the *Drosophila* Eye," *Cell* 123:1267-1277, Elsevier, Inc., The Netherlands (2005).

Lim, L., et al., "Microarray analysis shows that some microRNAs downregulate large numbers of target mRNAs," *Nature* 433:769-773, Nature Publishing Group, United Kingdom (2005).

Lima, W., et al., "Combinatorial Screening and Rational Optimization for Hybridization to Folded Hepatitis C Virus RNA of Oligonucleotides with Biological Antisense Activity," *J. Biol. Chem.* 272:626-638, American Society for Biochemistry and Molecular Biology, United States (1997).

Lin, C. J.-F., et al., "mir-122 targets an anti-apoptotic gene, Bcl-w. in human hepatocellular carcinoma cell lines," *Biochem. Biophys. Res. Comm.* DOI:10.1016/j.bbrc.2008.07.15, Academic Press, United States (2008).

Lindenbach, B.D., et al., "Complete Replication of Hepatitis C Virus in Cell Culture", Science 309:623-626, American Assn. for the Advancement of Science, United States (2005).

Lisziewicz, J., et al., "Long-term treatment of human immunodeficiency virus-infected cells with antisense oligonucleotide phosphorothioates," *Proc. Natl. Acad. Sci.* 90:3860-3864, National Academy of Sciences, United States (1993).

Liu, J., et aL, "The microRNAs of *Caenorhabditis elegans*," [powerpoint slides], 36 slides, Sep. 22, 2004.

Love, T.M., et al., "Not miR-ly small RNAs: Big potential for microRNAs in therapy," *J. Allergy. Clin. Immunol.* 121:309-319, Mosby, United States (2008).

Lu, J., et al., "MicroRNA expression profiles classify human cancers," *Nature* 435:834-838, Nature Publishing Group, United Kingdom (2005).

Lupberger, J., et al., "RNAi—A powerful tool to unravel hepatitis C virus-host interactions within the infectious live cycle", J. Hepatol. 48(3):523-525, Elsevier, United Kingdom (2007).

Machlin, E., et al., "Masking the 5' terminal nucleotides of the hepatitis C virus genome by an unconventional microRNA-target RNA complex," Proc. Natl. Acad. Sci. USA 108:3193-3198, National Academy of Sciences, USA (2011).

McLeod, B.W. et al., "The 'real world' utility of miRNA patents: lessons learned from expressed sequence tags," Nature Biotechnology 29: 129-133, Nature Publishing Group, United Kingdom (2011).

Manoharan, M., et al., "Novel Functionalization of the Sugar Moiety of Nucleic Acids for Multiple Labeling in the Minor Groove," *Tetrahedron Letters* 34:7171-7174, Pergamon Press, PLC., United Kingdom (1991).

Martinez, J., et al., Single-Stranded Antisense siRNAs Guide Target RNA Cleavage in RNAi, *Cell* 110:563-574, Cell Press, United States (2002).

Matz, M., et al., "Early post-transplant urinary IP-10 expression after kidney transplantation is predictive of short- and long-term graft function," *Kidney Int.* 69:1683-1690, Nature Publishing Group (2006).

Mayr, C., et al., "Disrupting the Pairing Between let-7 and Hmga2 Enhances Oncogenic Transformation," *Science* 315:1576-1579, American Assn. for the Advancement of Science, United States (2007).

McManus, M., and Sharp, P., "Gene Silencing in Mammals by Small Interfering RNAs," *Nat. Rev. Genet.* 3:737-747, Nature Publishing Group, United Kingdom (2002).

Meister, G., "Sequence-specific inhibition of micro-RNA- and siRNA-induced RNA silencing" *RNA* 10:544-550, Cold Spring Harbor Press, United States (2004).

Metzler, M., et al., "High expression of precursor microRNA-155/BIC RNA in children with Burkitt lymphoma", Genes Chromosomes Cancer 39: 167-169, Wiley-Liss, United States (2004).

Michael, M., et al., "Reduced Accumulation of Specific MicroRNAs in Colorectal Neoplasia," *Mol. Cancer Res.* 1:882-891, American Association for Cancer Research, United States (2003).

Mirnezami, A. H. F. et al., "MicroRNAs: Key players in carcinogenesis and novel therapeutic targets", Eur. J. Surg. Oncol. 35: 339-347, Elsevier, Netherlands (2009).

Miska, E.A., et al., "Most *Caenorhabditis elegans* microRNAs are individually not essential for development or viability", PLoS Genet. 3(12): e215, Public Library of Science, United States (2007).

Moore, S., "'Antisense' touted as medical hope, but critics ask if promise is reasonable," *Wall Street Journal (Eastern edition)*, New York, NY, May 10, 1996 p. A5A, 6 pgs (1996).

Möröy, T., et al., "Structure and expression of *hcr*, a locus rearranged with *c-myc* in a woodchuck hepatocellular carcinoma," *Oncogene* 4:59-65, Nature Publishing Group, United Kingdom (1989).

Mourelatos, Z., et al., "miRNPs: a novel class of ribonucleoproteins containing numerous microRNAs," *Genes Dev.* 16:720-728, Cold Spring Harbor Laboratory Press, United States (2002).

Naguibneva, I., et al., "The microRNAs in terminal muscle differentiation," [poster abstract] siRNAs and miRNAs Keystone Symposium, Keystone Resort, Colorado United States (2004).

Naguibneva, I., et al., "The microRNA *miR-181* targets the homeobox protein Hox-A11 during mammalian myoblast differentiation," *Nature Cell Biol.* 8:278-284, Nature Publishing Group, United States (2006).

Naguibneva, I., et al., "The microRNA *mir-181* targets the homeobox protein Hox-A11 during mammalian myoblast differentiation," *Nature Cell Biol.* 8 [Supplementary Information], Nature Publishing Group, United States (2006).

Naguibneva, I., et al., "An LNA-based loss-of-function assay for micro-RNAs," Biomed. & Pharmacother. 60:633-638, Elsevier Ltd., United Kingdom (2006).

Nelson, P., "The microRNA world: small is mighty," *Trends in Biochem. Sci.* 28:534-540, Elsevier Ltd., United Kingdom (2003).

Neuman, B., et al., "Antisense Morpholino-Oligomers Directed against the 5' End of the Genome Inhibit Coronavirus Proliferation and Growth," *J. Virol.* 78:5891-5899, American Society for Microbiology, United States (2004).

Nielsen S. U. et al., "Association between Hepatitis C Virus and Very-Low-Density Lipoprotein (VLDL)/LDL Analyzed in Iodixanol Density Gradients", Journal of Virology 80: 2418-2428, American Society for Microbiology, United States (2006).

Niepmann, M. "Activation of hepatitis C virus translation by a liver-specific microRNA", Cell Cycle 8: 1473-1477, Landes Bioscience, United States (2009).

Norman, K., and Sarnow, P., "Hepatitis C virus' Achilles' heel-dependence on liver-specififc microRNA miR-122," *Cell Res.* 20:247-249, Nature Publishing Group, United Kingdom (2010).

Norman, K. L. and Sarnow, P. Modulation of Hepatitis C Virus RNA Abundance and the Isoprenoid Biosynthesis Pathway by MicroRNA miR-122 Involves Distinct Mechanisms, Journal of Virology 84: 666-670, American Society for Microbiology, United States (2010).

Nulf, C. and Corey, D., "Intracellular inhibition of hepatitis C virus (HCV) internal ribosomal entry site (IRES)-dependent translation by, peptide nucleic acids (PNAs) and locked nucleic acids (LNAs)," *Nucleic Acids Res.* 32:3792-3798, Oxford University Press, United Kingdom (2004).

Obad, S., et al., "Targeting of cancer-associated microRNAs using short LNA-antimiR oligonucleotides," *European Journal of Cancer Supplements* 6:142, 20th Meeting of the European Association for Cancer Research, Lyon, France, Jun. 5-8, 2008.

Ørom, U., et al., "LNA-modified oligonucleotides mediate specific inhibition of microRNA function," *Gene* 372:137-141, Elsevier, Inc., The Netherlands (2006).

Ouellet, D., et al., "MicroRNAs in Gene Regulation: When the Smallest Governs It All," Article ID 69616, *Journal of Biomedicine and Biotechnology* 2006:1-20, Hindawi Publishing Corporation, United States (2006).

Pan, Q. et al., "New therapeutic opportunities for Hepatitis C based on small RNA", World J. Gastroenterol. 13: 4431-4436, Baishideng Pub., China (2007).

Pan, Q. et al., "Prospects of RNAi and microRNA-based therapies for hepatitis C," *Expert Opin. Biol. Ther.* 9(6):713-724, Informa Healthcare, United Kingdom (2009).

Park, J.-K., et al., "Antisense Inhibition of microRNA-21 or -221 Arrests Cell Cycle, Induces Apoptosis, and Sensitizes the Effects of Gemcitabine in Pancreatic Adenocarcinoma," *Pancreas* 38(7):e190-e199, Lippincott Williams & Wilkins, United States (2009).

Pasquinelli, A.E., et al., "Conservation of the sequence and temporal expression of let-7 heterochronic regulatory RNA," *Nature* 408:86-89, Nature Publishing Group, United Kingdom (2000).

Paushkin, S., et al., "The SMN complex, an assemblyosome of ribonucleoproteins," *Curr. Opin. Cell Biol.* 14:305-312, Elsevier Science Ltd., United Kingdom (2002).

Pavio, N. and Lai, M.M.C., "The hepatitis C virus persistence: how to evade the immune system?" *J. Boisci.* 28:287-304, Springer, India (2003).

Pedersen, D., et al., "Preparation of LNA Phosphoramidites," *Synthesis* 6:802-808, Thieme/Academic Press, Germany (2002).

Pedersen, D., and Koch, T., "Analogues of LNA (Locked Nucleic Acid), Synthesis of the 2'Thio-LNA Thymine and 5-Methyl Cytosine Phosphoramidites," Synthesis 4:578-582, Thieme/Academic Press, Germany (2003).

Pedersen, I., et al., "Interferon modulation of cellular microRNAs as an antiviral mechanism," *Nature* 449:919-923, Nature Publishing Group, United Kingdom (2007).

Petri, A., et al., "MicroRNA Silencing in Primates: Towards Development of Novel Therapeutics," *Can Res.* 69:393-395, American Association for Cancer Research, United States (2009).

Pietschmann, T. et al., "Construction and characterization of infectious intragenotypic and intergenotypic hepatitis C virus chimeras", Proc. Natl. Acad. Sci. USA 103: 7408-7413, National Academy of Sciences, United States (2006).

Pietschmann, T. et al., "Production of Infectious Genotype 1b Virus Particles in Cell Culture and Impairment by Replication Enhancing Mutations", PLoS Pathogens 5:1-14, Public Library of Science, United States (2009).

Poy, M., "A pancreatic islet-specific microRNA regulates insulin secretion," *Nature* 432:226-230, Nature Publishing Group, United Kingdom (2004).

Prakash, T., et al., "Antisense Oligonucleotides Containing Conformationally Constrained 2',4'-(*N*-Methoxy)aminomethylene and 2',4'-Aminooxymethylene and 2'-O,4'-*C*-Aminomethylene Bridged Nucleoside Analogues Show Improved Potency in Animal Models," *J. Med. Chem.* 53:1636-1650, American Chemical Society, United States (2010).

Regulus Therapeutic, Press release, "Regulus Therapeutics and GlaxoSmithKline Establish New Collaboration to Develop and Commercialize microRNA Therapeutics Targeting miR-122," Feb. 25, 2010, 2 pages.

Randall, G., et al., "Cellular cofactors affecting hepatitis C virus infection and replication," Proc. Natl. Acad. Sci. USA 104:12884-12889, National Academy of Sciences, United States (2007).

Robertson B. et al., "Specificity and functionality of microRNA inhibitors", Silence 1:10, BioMed Central, United Kingdom (2010).

Roberts, A.P.E. & Jopling, C.L., "Targeting viral infection by microRNA inhibition," *Genome Biology* 1:201, Biomed Central Ltd., England (2010).

Rosenbohm, C., et al., "Synthesis of 2'-amino-LNA: a new strategy," *Org. Biomol. Chem.* 1:655-663, Royal Society of Chemistry, United Kingdom (2003).

Saeed, A., et al., "TM4: A Free, Open-Source System for Microarray Data Management Analysis," *Bio Techniques* 34:374-378, Informa Healthcare USA, Inc., United Kingdom (2003).

Samuel, D., "Hepatitis C, Interferon, and Risk of Rejection After Liver Transplantation," *Liver Transpl.* 10:868-887, Wiley InterScience, United States (2004).

Santaris Pharma, In house Memo to attorney at Horton, Jan. 27, 2009 Santaris Memo 2009 (confidential).

Santaris Pharma, "LNA-antimiRs—Towards Effective MicroRNA Antagonists," Nature Genetics, vol. 38 Ad, , microRNA Supplement, Jun. 2006 [powerpoint slide], 1 page.

Sarasin-Filipowicz, M., et al., "Decreased levels of microRNA miR-122 in individuals with hepatitis C responding poorly to interferon therapy." *Nature Medicine* 15(1):31-33, Nature Publishing Company, United States (2009).

Sarnow, P. et al., "MicroRNAs: expression, avoidance and subversion by vertebrate viruses," *Nat. Rev. Microbiol.* 4:651-659, Nature Publishing Group, England (2006).

Sazani, P., et al., "Nuclear antisense effects of neutral, anionic and cationic oligonucleotide analogs," *Nucleic Acids. Res.* 29:3965-3974, Oxford University Press, United Kingdom (2001).

Schwarz, D., et al., "Evidence that siRNAs Function as Guides, Not Primers, in the *Drosophila* and Human RNAi Pathways," *Mol. Cell* 10:537-548, Cell Press, United States (2002).

Seth, P., et al., "Synthesis and Biophysical Evaluation of 2',4'-Constrained 2'*O*-Methoxyethyl and 2',4'-Constrained 2'*O*-Ethyl Nucleic Acid Analogues," *J. Org. Chem.* 75:1569-1581, American Chemical Society, United States (2010).

Shan, Y., et al., "Reciprocal Effects of Micro-RNA-122 on Expression of Heme Oxygenase-1 and Hepatitis C Virus Genes in Human Hepatocytes," *Gastroenterology* 133:1166-1174, W.B. Saunders, United States (2007).

Shan, Y., et al., "Reciprocal Effects of Micro-RNA-122 on Expression of Heme Oxygenase-1 and Hepatitis C Virus Genes in Human Hepatocytes," Hepatology 80A. AASLD abstract #181. Wiley, United States (2006).

Shan, V., et al., "An Antagomir of Mir-122 Down-Regulates Hepatitis C Virus infection and Up-Regulates Herne Oxygenase-1 Expression in Human Hepatocytes", Gastroenterology 132: A824, W.B. Saunders, United States (2007).

Singh, S. and Wengel, J., "Synthesis of Novel Bicyclo[2.2.1] Ribonucleosides: 2'-Amino- and 2'- Thio-LNA Monomeric Nucleosides," *J. Org. Chem.* 63:6078-6079, American Chemical Society, United States (1998).

Soifer, H., et al., "MicroRNAs in Disease and Potential Therapeutic Applications," *Mol. Ther.* 15:2070-2079, The American Society of Gene Therapy, United States (2007).

Sokol, N. and Ambros,V., "Mesodermally expressed *Drosophila microRNA-1* is regulated by Twist and is required in muscles during larval growth," *Gene Dev.* 19:2343-2354, (2005).

Sørensen, M., et al.,"α-L-*ribo*-Configured Locked Nucleic Acid (α-L-LNA): Synthesis and Properties," J. Am. Chem. Soc. 124:2164-2176, American Chemical Society, United States (2002).

Song, J.J. et al., "Crystal Structure of Argonaute and Its Implications for RISC Slicer Activity", Science 305, 1434-1437, American Assn. for the Advancement of Science, United States (2004).

Stark, A., et al., "Identification of *Drosophila* MicroRNA Targets," *PLoS Biology* 1:397-409, Academic Press, United States (2003).

Stein, C.A., "How to Design an Antisense Oligodeoxynucleotide Experiment: A Consensus Approach", Antisense Nucleic Acid Drug Dev. 8:129-132, Mary Ann Liebert, Inc., United States (1998).

Stenvang, J. and Kauppinen, S., "MicroRNAs as targets for antisense-based therapeutics," *Expert. Opin. Biol. Ther.* 8(1):59-81, Informa Healthcare, United Kingdom (2008).

Stenvang J. et al., "Targeting of microRNAs for therapeutics", Biochem. Soc. Trans. 36: 1197-1200, Portland Press on the Behalf of the Biochemical Society, United Kingdom (2008).

Swayze, E.E., et al. "Antisense oligonucleotides containing locked nucleic acid improve in animals," Nucleic Acids Res. 35:687-700, Oxford University Press, United Kingdom (2007).

Tallet-Lopez, B., et al., "Antisense oligonucleotides targeted to the domain IIId of the hepatitis C virus IRES compete with 40S ribosomal subunit binding and prevent in vitro translation," *Nucleic Acids Res.* 31:734-742, Oxford University Press, United Kingdom (2003).

Tam, W., "Identification and characterization of human *BIC*, a gene on chromosome 21 that encodes a noncoding RNA," *Gene* 274:157-167, Elsevier, The Netherlands (2001).

Tijsterman, M., et al., "RNA Helicase MUT-14-Depedent Gene Silencing Triggered in *C. elegans* by Short Antisense RNAs," *Science* 295:694-697, American Assn. for the Advancement of Science, United States (2002).

Timmerman L., "Regulus, the microRNA child of Isis and Alnylam, strkes potential $150M deal with Glaxo." Xconomy on line publication, Feb. 25, 2010.

Triboulet, R., et al., "Suppression of MicroRNA-Silencing Pathway by HIV-1 During Virus Replication," *Science* 315:1579-1582, American Assn. for the Advancement of Science, United States (2007).

Tsai, W.-C., et al., "MicroRNA-122, a Tumor Suppressor MicroRNA that Regulates Intrahepatic Metastasis of Hepatocellular Carcinoma," *Hepatology* DOI:10.100/hep.22806, Wiley, United States (2009).

Tsuchiya, Y., et al., "MicroRNA Regulates the Expression of Human Cytochrome P450 1B1," *Cancer Res.* 66:9090-9098, American Association for Cancer Research, United States (2006).

Uhlmann, E., "Recent advances in the medicinal chemistry of antisense oligonucleotides," *Curr. Opin. Drug Discov.* 3:203-213, Pharma Press Ltd., United Kingdom (2000).

Uhlmann, E. and Peyman, A., "Antisense Oligonucleotides: A New Therapeutic Principle", Chemical Reviews 90: 543-584, American Chemical Society, United States (1990).

Válóczi, A., et al., "Sensitive and specific detection of microRNAs by northern blot analysis using LNA-modified oligonucleotide probes," Kingdom (2004).

van Rooij, E., et al., "Control of Stress-Dependent Cardiac Growth and Gene Expression by a MicroRNA," *Science* 316:575-579, American Assn. for the Advancement of Science, United States (2007).

van Rooij, E. and Olson, E., "MicroRNAs: powerful new regulators of heart disease and provocative therapeutic targets," *J. Clinic. Invest.* 117:2369-2376, American Society for Clinical Investigation, United States (2007).

Wagner, R., "Gene inhibition using antisense oligodeoxynucleotides," *Nature* 372:333-335, Nature Publishing Group, United Kingdom (1994).

Wagner, R., et al., "Potent and selective inhibition of gene expression by an antisense heptanucleotide," *Nat. Biotechnol.* 14:840-844, Nature Publishing Group, United Kingdom (1996).

Wahlestedt, C., et al., "Potent and nontoxic oligonucleotides containing locked nucleic acids," *Proc. Natl. Acad. Sci. USA* 97:5633-5638, National Academy of the Sciences, United States (2000).

Wakita T. et al., "Production of infectious hepatitis C virus on tissue culture from a cloned viral genome", Nat Med. 11(7): 791-796, Nature PublishingCompany, United States (2005).

Wakita T. et al., and Pietschmann T. et al., Abstracts O-33 & O-34, 11th International Symposium on HCV & Related Viruses, Heidelberg, Oct. 3-7, 2004.

Walter, T., et al., "Rejection Under Alpha Interferon Therapy in Liver Transplant Recipients," *American Journal of Transplantation* 7:177-184, Blackwell Munksgaard, Denmark (2007).

Wang, X., et al., "MicroRNA-122a functions as a novel tumor suppressor downstream of adenomatous polyposis coli in gastrointestinal cancers," *Biochem. Biophys. Res. Comm.* 387:376-380, Academic Press, United States (2009).

Wang, Z. et al., "miRNAs at the heart of the matter," *J. Mol. Med.* DOI:10.1007/s00109-008-0341-3, Springer International, Germany (2008).

Watanabe, T.A. et al., "Plasma Protein Binding of an Antisense OligonucleotideTargeting Human ICAM-I (ISIS 2302)", Oligonucleotides 16:169-180, Mary Ann Liebert, Inc., United States (2006).

Wehner, K.A. & Sarnow, P., "Regulation of mRNA molecules by microRNAs," Translational Control in Biology & Medicine, Cold Spring Harbor Monograph Series 48:297-318, Cold Spring Harbor Laboratory Press, United States (2007).

Weiler, J., et al., "Anti-miRNA oligonucleotides (AMOS): ammunition to target miRNAs implicated in human disease?" *Gene Ther.* 13:496-502, Nature Publishing Group, United Kingdom (2006).

Wengel J., "LNA (Locked Nucleic Acid", in Antisense Drug Technology, Principles,Strategies and Applications, Ed. Crooke S.T. p. 339-357 (2001).

Wengel, J., et al., "Chemistry of locked nucleic acids (LNA): Design, synthesis, and bio-physical properties," Letters in Peptide, 10:237-253, Kluwer Academic Publishers, Germany (2004).

Wienholds, E., et al., "MicroRNA Expression in Zebrafish Embryonic Development," *Science* 309:310-311, American Assn. for the Advancement of Science, United States (2005).

Worm, J., et al., "Silencing of microRNA-155 in mice during acute inflammatory response leads to derepression of c/ebp Beta and down-regulation of G-CSF," Nucleic Acids Res. 37:5784-5792, Oxford University Press, United Kingdom (2009).

Wu, X., et al., "miR-122 affects the viability and apoptosis of hepatocellular carcinoma cells," *Scand. J. Gastroenter.* 44:1332-1339, Informa Healthcare, United Kingdom (2009).

Xiao, J. et al., "Novel Approaches for Gene-Specific Interference Via Manipulating Actions of MicroRNAs: Examination on the Pacemaker Channel Genes HCN2 and HCN4", J. Cell. Physiol. 212: 285-292, Wiley-Liss, New York, United States (2007).

Xie, Z-C. et al., "Transmission of Hepatitis C Virus Infection to Three Shrews", Virology 244: 513-520, Academic Press, New York, United States (1998).

Yang, B., et al., "The muscle-specific microRNA *miR-1* regulates cardiac arrhythmogenic potential by targeting *GJA1* and *KCNJ2*," *Nat. Med.* 13:486-491, Nature Publishing Company, United States (2007).

Yekta, S., et al., "MicroRNA-Directed Cleavage of *HOXB8* mRNA," *Science* 303:594-596, American Assn. for the Advancement of Science, United States (2004).

Yi, M.K. and Lemon, S. M., "Adaptive Mutations Producing Efficient Replication of Genotype 1a Hepatitis C Virus RNA in Normal Huh7 Cells", J. Virol. 78: 7904-7915, American Society for Micobiology (2004).

Yi-Ping, L. et al., "MicroRNA-122 antagonism against hepatitis C virusgenotypes 1-6 and reduced efficacy by host RNA insertion or mutations in the HCV 5' UTR", PNAS early edition, www.pnas.org/cgi/doi/10.1073/pnas.1016606108, National Academy of Sciences, United States (2011).

Yu, J., et al., "RNA interference by expression of short-interfering RNAs and hairpin RNAs in mammalian cells," *Proc. Natl. Acad. Sci.* 99:6047-6052, National Academy of Sciences, United States (2002).

Zamecnik, P. C. and Stephenson M. N., "Inhibition of *Rous sarcoma virus* replication and cell transformation by a specific oligodeoxynucleotide", Proc. Natl. Acad. Sci. USA 75:280-284, National Academy of Sciences, United States (1978).

Zhang, H., et al., "Antisense Oligonucleotide Inhibition of Hepatitis C Virus (HCV) Gene Expression in Livers of Mice Infected with an HCV-Vaccinia Virus Recombinant," *Antimicrobial Angets and Chemotherapy* 43:347-353, American Society for Microbiology, United States (1999).

Zhao, Y., et al., "Serum response factor regulates a muscle-specific microRNA that targets *Hand2* during cardiogenesis," *Nature* 436:214:220, Nature Publishing Group, United Kingdom (2005).

Zhong, J. et al., "Robust hepatitis C virus infection in vitro", Proc. Natl. Acad. Sci. USA 102:9294-9299, National Academy of Sciences, United States (2005).

Baofeng Y., et al. P.R.C patent application No. 200710072002. Extract from SIPO database, accessed in Jun. 6, 2007, 1 page.

Response and Amended Claims dated Sep. 17, 2007 in Office Action mailed on Mar. 16, 2007, U.S. Appl. No. 10/909,125, Esau et al., filed Jul. 30, 2004, 14 pages.

Response and Applicant dated May 13, 2008, in Office Action mailed Nov. 13, 2007 on U.S. Appl. No. 10/909,125, Esau et al., filed Jul. 30, 2004, 10 pages.

Response and Amended Claims dated Aug. 4, 2009 in reply to Office Action mailed on Mar. 16, 2007 in U.S. Appl. No. 10/909,125, 12 pages.

Response to Office Action mailed Sep. 13, 2006 in U.S. Appl. No. 11/122,328, Sarnow et al., filed May 3, 2005, 11 pages.

International Search Report and Written Opinion for International Appl. No. PCT/DK2007/000169, European Patent Office, Netherlands, mailed on Mar. 7, 2008.

International Search Report for International Appl. No. PCT/EP2007/060703, European Patent Office, Netherlands, mailed on Aug. 13, 2008.

International Search Report for International Appl. No. PCT/EP2008/053309, European Patent Office, Netherlands, mailed on Jul. 18, 2008.

International Search Report for International Appl. No. PCT/EP2008/066920, European Patent Office, Netherlands, mailed on Jun. 17, 2009.

Bartenschlager, R. and Lohmann, V., "Replication of hepatitis C virus," J. Gen. Virol. 81:1631-1648, Great Britain (2000).

Jannsen, H., et al., "A Randomized, Double-blind, Placebo (PLB) Controlled Safety and Anti-viral Proof of Concept Study of Miravirsen (MIR), an Oligonucleotide Targeting miR-122, In Treatment Naive Patients with Genotype 1 (GT1) Chronic HCV Infection," (Absract) American Association for the Study of Liver Diseases (AASLD) 2011 Annual Meeting Abstract, Nov. 7, 2011, San Francisco, California, 1 page.

"Declaration of Dr. Susanna Obad," from File History of European Patent No. 1747023, dated Sep. 27, 2011, 4 pages.

"Declaration under 37 CFR 1.132 of Dr. Christine Esau," dated Apr. 15, 2011, from the File History of U.S. Appl. No. 11/513,102, filed Aug. 29, 2006, 5 pages.

"Exclusive License and Nonexclusive Option Agreement Between Glaxo Group Limited Regulus Therapeutics Inc.," Isis Pharmaceutics (Confidential), Exhibit 10.2, License Agreement, 56 pages.

McNair, T., "Cholesterol," BBC Health, accessed at: http://www.bbc.co.uk/health/physical_health/conditions/cholesterol1.shtml, accessed at Nov. 7, 2011, 3 pages.

"Opposition against European Patent No. 1 931 782 B1 granted to Isis Pharmaceuticals Inc." Document No. G0119EP, Santaris Pharma A/S, Oct. 4, 2011, 46 pages.

Opposition Statement by Santaris Pharma A/S to EP-B-1747023, in the name of The Board of Trustees of the Leland Stanford Junior University, 94 pages.

Santaris Pharma A/S report new clinical data from miravirsen Phase 2a study to treat Hepatitis C in late-breaking oral presentation at the AASLD annual meeting, (Press Release) American Association for the Study of Liver Diseases (AASLD) 2011 Annual Meeting, Nov. 7, 2011, San Francisco, California, 2 pages.

Office Action mailed on Aug. 25, 2011 in U.S. Appl. No. 12/245,544, inventor Obad, filed Oct. 3, 2008, 38 pages.

Office Action mailed on Aug. 3, 2011 in U.S. Appl. No. 12/295,960, inventors Elmén, et al., filed Mar. 30, 2009, 43 pages.

Office Action mailed on Nov. 22, 2011 in U.S. Appl. No. 12/400,625, inventors Kauppinen, et al., filed Mar. 9, 2009, 42 pages.

Office Action mailed on May 10, 2012 in U.S. Appl. No. 13/006,099, inventors Elmen et al., filed Jan. 13, 2011, 12 pages.

Office Action mailed on May 2, 2012 in U.S. Appl. No. 12/400,625, inventors Kauppinen, et al., filed Mar. 9, 2009, 35 pages.

Office Action mailed on May 25, 2010 in U.S. Appl. 12/767,631, inventors Hildebrant-Eriksen, et al., filed Apr. 26, 2010, 19 pages.

Office Action mailed on Oct. 25, 2010 in U.S. Appl. No. 12/767,631, inventors Hildebrant-Eriksen, et al., filed Apr. 26, 2010, 15 pages.

Office Action mailed on Dec. 30, 2011 in U.S. Appl. No. 12/921,339, inventor Kauppinen, filed Nov. 29, 2010, 25 pages.

Office Action mailed on Jul. 13, 2010 25, in U.S. Appl. No. 12/296,084, inventors Elmen et al., filed Sep. 10, 2009.

Office Action mailed on Nov. 5, 2010 in U.S. Appl. No. 12/400,625, inventor Kauppinen, filed Mar. 9, 2009.

International Search Report for International Application No. PCT/DK2007/000168, European Patent Office, mailed on Jan. 28, 2008.

International Search Report for International Application No. PCT/DK2008/000345, European Patent Office, mailed on Oct. 7, 2009.

The Written Opinion of the International Searching Authority for International Application No. PCT/DK2008/000345, European Patent Office, mailed on Oct. 7, 2009.

International Search Report for International Application No. PCT/DK2008/000344, European Patent Office, mailed on Oct. 7, 2009.

International Search Report for International Application No. PCT/DK2007/000169, European Patent Office, mailed on Jul. 3, 2008.

International Search Report for International Application No. PCT/EP2009/052728, European Patent Office, mailed on Jul. 31, 2009.

Co-pending U.S. Appl. No. 13/415,685, filed Mar. 8, 2012, United State Patent Office, Alexandria, Va, United State (Not Published).

Berezikov, et al. "Approaches to microRNA discovery," Nature Genetics Supplement 38:S2-S7, Nature Publishing Group, United Kingdom (2006).

Doench, et al. "Specificity of microRNA target selection in translational repression," Genes & Development 18:504-511, Cold Spring Harbor Laboratory Press, United States (2004).

Engels et al. "Principles and effects of microRNA-mediated post-transcriptional gene regulation", Oncogene 25:6163-6169, Nature Publishing Group, United Kingdom (2006).

Fluiter, et al. "On the in vitro and in vivo properties of four locked nucleic acid nucleotides incorporated into an anti-H-Ras antisense oligonucleotide," ChemBioChem. 6:1104-1109, Wiley-VCH Verlag GmbH & Co., Germany (2005).

Hornstein, et al. "Canalization of development by microRNAs," Nature Genetics Supplement 38:S20-S24, Nature Publishing Group, United Kingdom (2006).

Rajewsky, "MicroRNA target predictions in animals," Nature Genetics Supplement 38:S8-S13, Nature Publishing Group, United Kingdom (2006).

Roberts, et al. "Efficient and persistent splice switching by systemically delivered LNA oligonucleotides in mice," Molecular Therapy 14:471—(2006).

Office Action mailed on Sep. 20, 2012, in U.S. Appl. No. 13/006,099, inventors Elmen et al., filed Jan. 13, 2011, 12 pages.

Office Action mailed on Sep. 10, 2012, in U.S. Appl. No. 12/921,339, inventors Kauppinen et al., filed Nov. 29, 2010, 7 pages.

Advisory Action mailed on Oct. 25, 2012, in U.S. Appl. No. 12/767,631, filed Apr. 26, 2010, 3 pages.

Elayadi et al. "Implification of High-Affinity Hybridization by Locked Nucleic Acid Oligomers for Inhibition of Human Telomerase," Biochemistry 41:9973-9981, ACS Publicatons, United States (2002).

\* cited by examiner

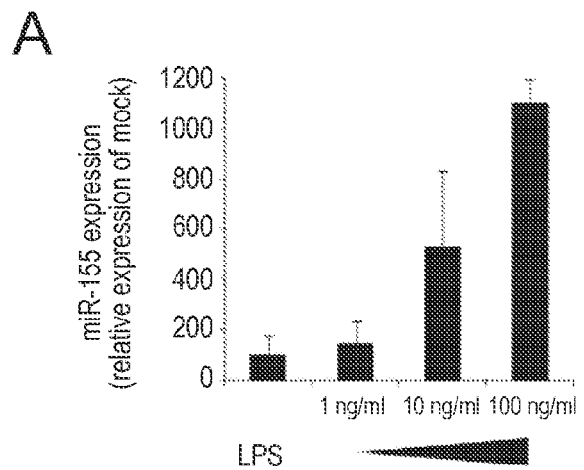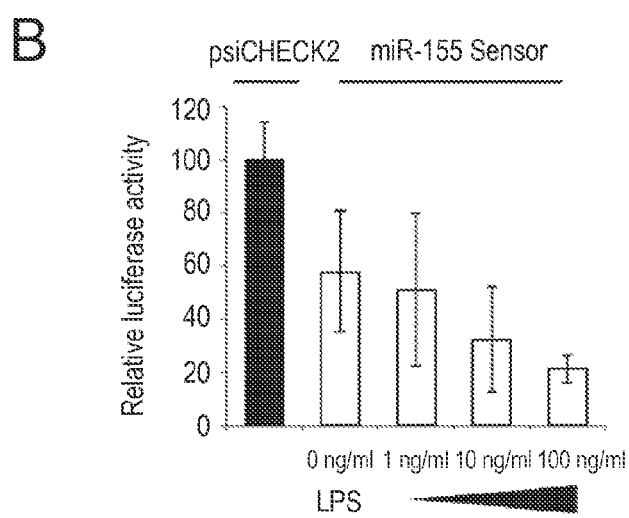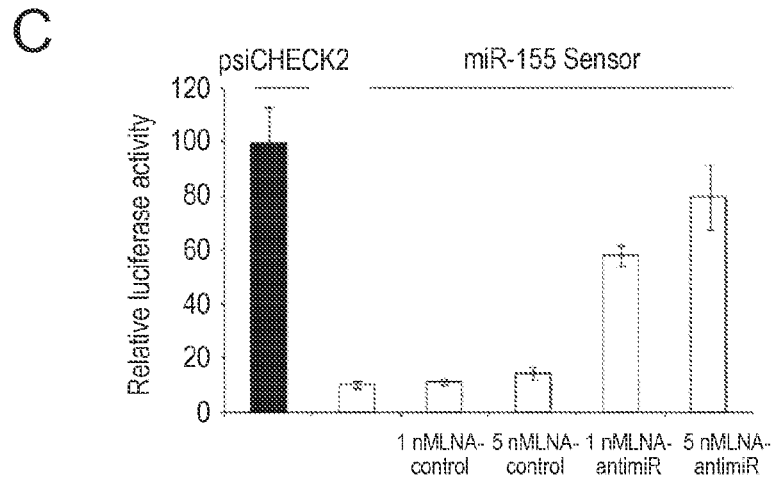
FIG. 1

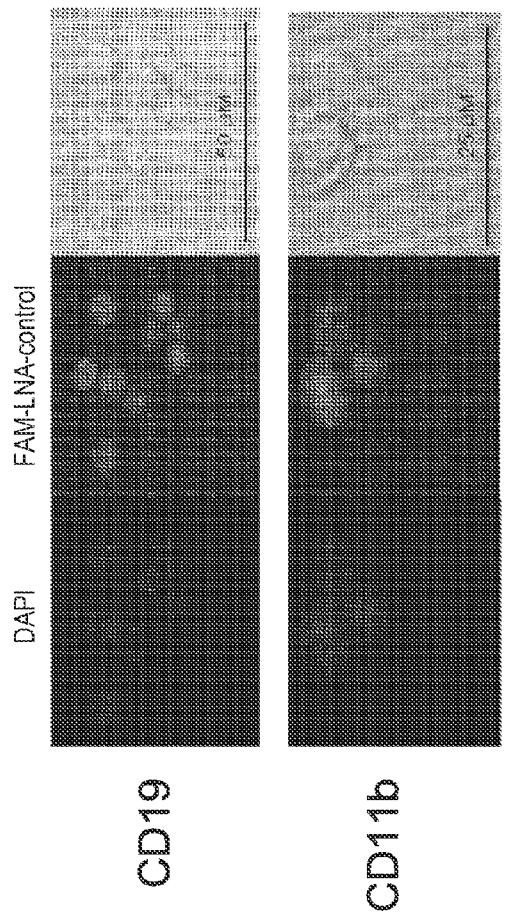

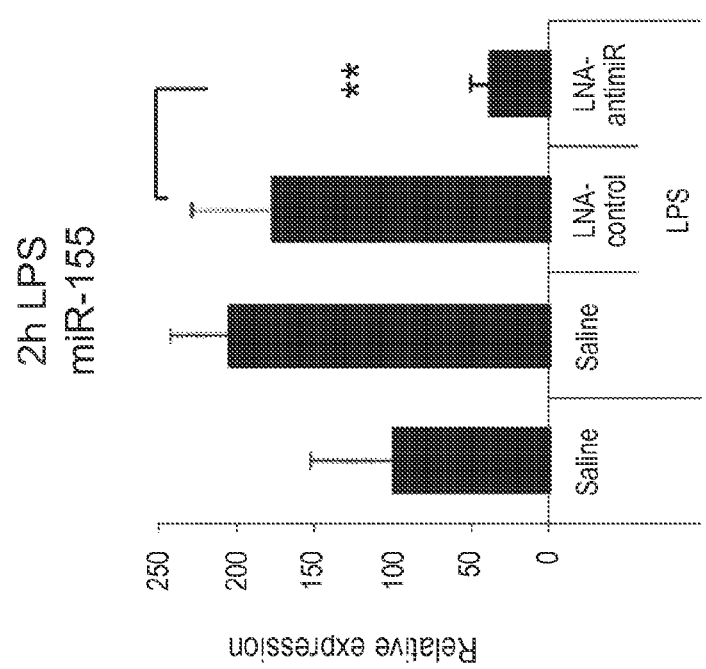

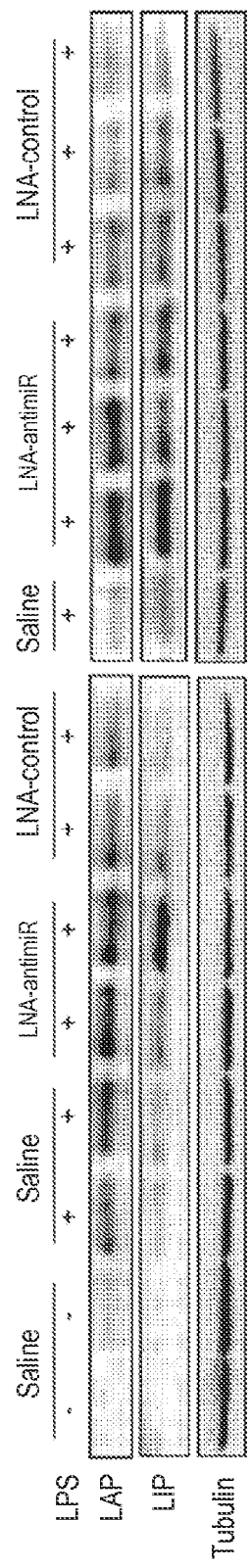

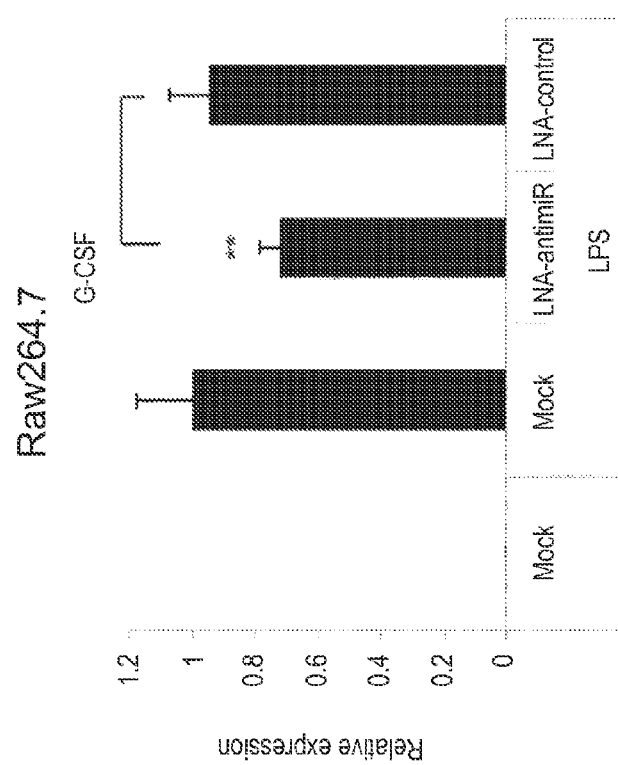

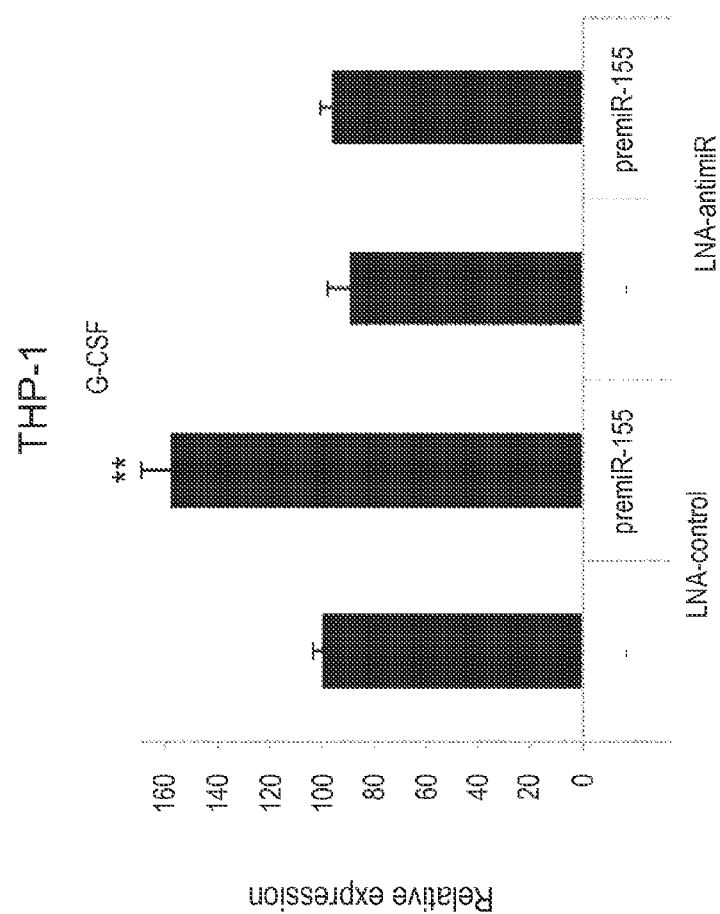

FIG. 6

| Assay | No LPS | st.dev. | LPS+ Mock | st.dev | LPS + LNA-antimiR | st.dev | LPS + LNA-control | st.dev. |
|---|---|---|---|---|---|---|---|---|
| 18S-Hs99999901_s1 | 0.9375 | 0.0004 | 1.0279 | 0.2677 | 0.8610 | 0.1219 | 0.7599 | 0.1857 |
| Actb-Mm00607939_s1 | 0.7388 | 0.2016 | 1.0096 | 0.1530 | 0.7417 | 0.0901 | 0.8452 | 0.1471 |
| B2m-Mm00437762_m1 | 1.0000 | 0.0000 | 1.0000 | 0.0000 | 1.0000 | 0.0000 | 1.0000 | 0.0000 |
| Bax-Mm00432050_m1 | 1.2480 | 0.3010 | 1.0064 | 0.1300 | 0.9081 | 0.2158 | 0.6668 | 0.1006 |
| Bcl2-Mm00477631_m1 | 2.2519 | 0.2083 | 1.0223 | 0.2355 | 1.1066 | 0.3723 | 1.1092 | 0.3027 |
| Bcl2l1-Mm00437783_m1 | 0.1991 | 0.0384 | 1.0024 | 0.0792 | 0.7747 | 0.0464 | 0.6049 | 0.0819 |
| Ccl2-Mm00441242_m1 | 0.0253 | 0.0078 | 1.0031 | 0.0879 | 0.7080 | 0.1112 | 0.8733 | 0.1057 |
| Ccl5-Mm01302426_m1 | 0.0097 | 0.0002 | 1.0311 | 0.2767 | 0.7837 | 0.2088 | 0.6619 | 0.2531 |
| Ccr2-Mm99999051_gH | 0.3607 | 0.0768 | 1.0173 | 0.2206 | 0.9392 | 0.3163 | 1.0573 | 0.3798 |
| Cd40-Mm00441895_m1 | 0.0245 | 0.0069 | 1.0333 | 0.3095 | 0.5908 | 0.1918 | 0.5971 | 0.1193 |
| Cd63-Mm00839636_g1 | 1.3071 | 0.0866 | 1.0140 | 0.1842 | 1.1925 | 0.5203 | 1.1315 | 0.2784 |
| Col4a5-Mm00801606_m1 | 1.5525 | 0.0868 | 1.0150 | 0.1930 | 0.8615 | 0.2284 | 0.9067 | 0.2539 |
| Csf1-Mm00432688_m1 | 0.0820 | 0.0113 | 1.0098 | 0.1583 | 0.5355 | 0.1996 | 0.6288 | 0.2083 |
| Csf2-Mm00438328_m1 | 0.0054 | 0.0010 | 1.0057 | 0.1193 | 0.8158 | 0.3177 | 0.8675 | 0.1253 |
| Csf3-Mm00438334_m1 | 0.0006 | 0.0006 | 1.0140 | 0.1819 | 0.7346 | 0.0606 | 0.9587 | 0.1268 |
| Cxcl10-Mm00445235_m1 | 0.0619 | 0.0083 | 1.0128 | 0.1801 | 0.5590 | 0.3970 | 0.4628 | 0.2324 |
| Cxcl11-Mm00444662_m1 | 0.0721 | 0.0042 | 1.0201 | 0.2329 | 0.6205 | 0.3733 | 0.3965 | 0.2425 |
| Cxcr3-Mm00438259_m1 | 0.6879 | 0.1250 | 1.0141 | 0.1913 | 1.6589 | 1.2262 | 1.3932 | 0.7609 |
| Edn1-Mm00438656_m1 | 0.0057 | 0.0046 | 1.0012 | 0.0561 | 0.6144 | 0.3441 | 0.5755 | 0.2039 |
| Fas-Mm00433237_m1 | 0.0240 | 0.0057 | 1.0221 | 0.2453 | 1.1592 | 0.3020 | 1.1681 | 0.5521 |
| Gapdh-Mm99999915_g1 | 1.3360 | 0.2801 | 1.0268 | 0.2593 | 1.0652 | 0.1755 | 1.0717 | 0.0859 |
| Gusb-Mm00446953_m1 | 1.4499 | 0.1742 | 1.0096 | 0.1570 | 0.9847 | 0.3647 | 1.0177 | 0.1633 |
| Hmox1-Mm00516004_m1 | 0.2595 | 0.0679 | 1.0166 | 0.2106 | 1.0389 | 0.3518 | 1.1968 | 0.3125 |
| Hprt1-Mm00446968_m1 | 1.2865 | 0.2521 | 1.0126 | 0.1761 | 1.0330 | 0.1590 | 0.9580 | 0.0894 |
| Ikbkb-Mm00833995_m1 | 1.2613 | 0.1259 | 1.0185 | 0.2196 | 0.8985 | 0.0924 | 0.9720 | 0.2798 |

| Assay | No LPS | st.dev. | LPS+ Mock | st.dev | LPS + LNA-antimiR | st.dev | LPS + LNA-control | st.dev. |
|---|---|---|---|---|---|---|---|---|
| Il10-Mm00439616_m1 | 0.0142 | 0.0087 | 1.0169 | 0.2036 | 0.6034 | 0.2930 | 0.4887 | 0.2002 |
| Il15-Mm00434210_m1 | 0.1162 | 0.0235 | 1.0128 | 0.1855 | 0.5932 | 0.1028 | 0.5972 | 0.1610 |
| Il18-Mm00434225_m1 | 0.3446 | 0.0047 | 1.0082 | 0.1449 | 0.5391 | 0.2131 | 0.5093 | 0.1543 |
| Il1a-Mm00439620_m1 | 0.0006 | 0.0005 | 1.0243 | 0.2393 | 0.9922 | 0.3170 | 1.0616 | 0.4361 |
| Il1b-Mm00434228_m1 | 0.0008 | 0.0007 | 1.0084 | 0.1451 | 1.2679 | 0.4510 | 1.2943 | 0.4952 |
| Il6-Mm00446190_m1 | 0.0092 | 0.0070 | 1.0212 | 0.2408 | 0.6995 | 0.2504 | 0.8726 | 0.0873 |
| Nfkb1-Mm00476361_m1 | 0.2822 | 0.0703 | 1.0450 | 0.3146 | 1.0648 | 0.2674 | 1.0596 | 0.1769 |
| Nfkb2-Mm00479807_m1 | 0.4927 | 0.0378 | 1.0262 | 0.2531 | 1.0900 | 0.5365 | 0.9908 | 0.2922 |
| Nos2-Mm00440485_m1 | 0.0058 | 0.0005 | 1.0166 | 0.2104 | 0.6834 | 0.3175 | 0.7239 | 0.2233 |
| Pgk1-Mm00435617_m1 | 1.1348 | 0.4384 | 1.0202 | 0.2212 | 1.0281 | 0.1465 | 1.0367 | 0.1242 |
| Ptgs2-Mm00478374_m1 | 0.0185 | 0.0078 | 1.0148 | 0.1869 | 0.8186 | 0.0984 | 0.8933 | 0.2053 |
| Ptprc-Mm00448463_m1 | 0.7932 | 0.1191 | 1.0135 | 0.1956 | 1.0371 | 0.3183 | 0.9987 | 0.1665 |
| Ski-Mm00448744_m1 | 1.7935 | 0.4346 | 1.0146 | 0.1999 | 0.9487 | 0.2828 | 1.1385 | 0.1931 |
| Smad3-Mm00489637_m1 | 16.1292 | 1.1624 | 1.0609 | 0.3625 | 1.9802 | 1.2987 | 1.9752 | 0.6622 |
| Smad7-Mm00484741_m1 | 0.4462 | 0.2992 | 1.0073 | 0.1386 | 1.1874 | 0.5784 | 1.2480 | 0.3949 |
| Socs1-Mm00782550_s1 | 0.1742 | 0.0039 | 1.0138 | 0.1922 | 0.5360 | 0.0675 | 0.6564 | 0.0521 |
| Stat1-Mm00439518_m1 | 0.4861 | 0.0600 | 1.0116 | 0.1763 | 0.6385 | 0.1285 | 0.8379 | 0.1344 |
| Stat3-Mm00456961_m1 | 0.3762 | 0.0992 | 1.0109 | 0.1704 | 0.6836 | 0.0788 | 0.7288 | 0.0564 |
| Stat6-Mm00447411_m1 | 22.2184 | 28.9697 | 9.9266 | 17.5966 | 2.7782 | 3.0628 | 0.3388 | 0.2099 |
| Tfrc-Mm00441941_m1 | 0.9249 | 0.1226 | 1.0095 | 0.1560 | 0.9890 | 0.3955 | 0.9834 | 0.1973 |
| Tgfb1-Mm00441724_m1 | 0.5160 | 0.0577 | 1.0136 | 0.1894 | 1.1053 | 0.4592 | 0.9811 | 0.3000 |
| Tnf-Mm00443258_m1 | 0.1424 | 0.0465 | 1.0124 | 0.1901 | 0.8968 | 0.2159 | 0.9019 | 0.1719 |
| Vegfa-Mm00437304_m1 | 0.4666 | 0.0576 | 1.0184 | 0.2105 | 1.7543 | 1.2141 | 1.4760 | 0.5834 |

MICRO-RNA MEDIATED MODULATION OF COLONY STIMULATING FACTORS

RELATED APPLICATIONS

This application is the National Stage of International Application No. PCT/EP2009/059608. filed Jul. 24, 2009, which claims the benefit of U.S. Provisional Application No. 61/085,644, filed Aug. 1, 2008, and U.S. Provisional Application No. 61/121,204, filed Dec. 10, 2008, all of which are incorporated herein by reference in their entireties.

REFERENCE TO SEQUENCE LISTING SUBMITTED ELECTRONICALLY VIA EFS-WEB

The content of the electronically submitted sequence listing (Name: 2763_0180001_Sequence_Listing.txt; Size: 14,882 bytes, and Date of Creation: Jan. 25, 2013) filed with the application is incorporated herein by reference in its entirety.

FIELD OF INVENTION

The present invention relates to the modulation of immunoregulatory proteins, including cytokines, such as colony stimulatory factors (CSF) via the use of microRNA-155 inhibitors or mimics. The present invention relates to novel LNA compounds which mediate simultaneous down-regulation of the Monocyte Chemoattractant Protein-1 (MCP-1 or CCL2) and Interleukine-6, as well as of M-CSF and G-CSF. Such LNA compounds are highly useful in the prevention or treatment of chronic or acute inflammatory or autoimmune diseases, especially those associated with aberrant lymphocyte or monocyte accumulation such as Chronic and acute inflammatory or autoimmune diseases, aberrant lymphocyte or monocyte accumulation, arthritis, juvenile idiopathic arthritis, rheumatoid arthritis, acute and chronic arthritis, asthma, atherosclerosis, diabetic nephropathy, inflammatory bowel disease, Crohn's disease, multiple sclerosis, nephritis, glomerulonephritis, pancreatitis, pulmonary fibrosis, psoriasis, restenosis, transplant rejection, early stages of allergic responses, inhibition of LTC4, to prevent AHR (airway hyper-responsiveness), tuberculosis infection and malignancy, stroke, castleman's disease, neoplasm, high-grade multiple myeloma, malignant mesotheliomas, paraneoplastic syndrome of mesotheliomas, immunosuppression, cachexia, thrombocytosis, amyloidosis, osteogenesis imperfect, homocystinuria, osteoporosis, osteopetrosis, inflammation of bone mass w arthritis and r. arthritis, peridontal disease, fibrous dysplasia, Paget's disease, chronic renal failure, endocrinopathies, hypercalcemia, deficiency states, malabsorption syndromes, cronic liver disease, cancer metastasis, mammary tumor progression to metastasis.

More specifically, the invention is related to pharmaceutical compositions comprising such LNA compounds and the use of these compounds and compositions in the prevention or treatment of such diseases.

RELATED CASES

The following related applications which disclose microRNA 155 inhibitors (antimiRs) are hereby incorporated by reference: WO2007/112754, WO2007/112753, EP Application number 08104780, and U.S. provisional applications U.S. 60/979217 and U.S. 61/028062.

BACKGROUND

Colony-stimulating factors (CSFs) are secreted glycoproteins which bind to receptor proteins on the surfaces of hemopoietic stem cells and thereby activate intracellular signaling pathways which can cause the cells to proliferate and differentiate into a specific kind of blood cell (usually white blood cells). In humans there are three CSF genes, CSF1 which encodes macrophage CSF (M-CSF), CSF2, which encodes the granulocytes macrophage CSF (GM-CSF), and CSF3, which encodes the granulocyte CSF (G-CSF).

Hamilton, Nature Reviews 8 (2008), pp 533-544 reports that depletion of CSFs have a therapeutic benefit in many inflammatory and/or autoimmune diseases and that there are numerous antibody therapies in clinical development targeted to CSFs for therapy of inflammation.

Neupogen®(Filgrastim) is a heterologously produced human G-CSF produced by Amgen for enhancing white blood cell concentration in cancer patients being treated with chemotherapy.

G-CSF has been indicated in chronic inflammatory autoimmune diseases, such as type II hypersensitivity responses, including rheumatoid arthritis.

MicroRNA-155 is induced during the macrophage inflammatory response (O'Connell et al., PNAS 104 (5) pp 1604-9).

WO2008/017126 refers antisense compounds which target the granulocyte colony-stimulating factor (G-CSF), and the use of such compounds for the treatment of pulmonary disease. G-CSF protein has been developed as a therapeutic agent for increasing white blood cell counts, and can enhance the immune system's ability to raise a Th-2 response that can decrease Th-1 mediated inflammatory responses, for example in Crohn's disease.

G-CSF

Granulocyte colony-stimulating factor (G-CSF) is a colony-stimulating factor hormone. It is a glycoprotein, growth factor or cytokine produced by a number of different tissues to stimulate the bone marrow to produce granulocytes and stem cells. G-CSF then stimulates the bone marrow to release them into the blood. It also stimulates the survival, proliferation, differentiation, and function of neutrophil precursors and mature neutrophils.

It is playing importance in inflammatory joint diseases as G-CSF-deficient mice are protected from acute and chronic arthritis. Reduced severity was associated with blunted mobilization of granulocytic cells from the bone marrow and less cellular infiltrate and cellular activation in inflamed joints. It has also been demonstrated that G-CSF blockade in established collagen-induced arthritis in WT mice markedly reduces disease manifestations and is as effective as tumor necrosis factor blockade. G-CSF plays a critical role in driving joint inflammation and G-CSF is a potential therapeutic target in inflammatory joint diseases, such as rheumatoid arthritis (Lawlor et al., PNAS, 2004).

Worsening of Psoriasis afte treatment with G-CSF have been reported (Feliu et al., JNCI, 1997) indicating a role for G-CSF in the pathogenesis of Psoriasis.

M-CSF

Macrophage colony-stimulating factor, or M-CSF, is a secreted cytokine which influences hemopoietic stem cells to differentiate into macrophages or other related cell types. Also the macrophage-colony stimulating factor, M-CSF supports osteoclast formation (Yoshida et al. Nature 345: 442-444, 1990). Osteoclasts mediate bone readsorption. Osteoclasts are multinucleated cells differentiating from haemopoietic cells (Walker, Science 190: 784-785, 1975) and they share a common stem cell with monocyte-macrophage lineage cells (Ash et al., Nature 283: 669-670, 1980). The differentiation of osteoclast precursors into mature multinucleated osteoclasts requires different factors including hormonal and local stimuli (Walker, Science 190: 784-785,1975)

and living bone and bone cells have been shown to play a critical role in osteoclast development (Hagenaars et al., Bone Miner 6: 179-189,1989). Osteoblastic or bone marrow stromal cells are also required for osteoclast differentiation and one of the factors produced by these cells that supports osteoclast formation is macrophage-colony stimulating factor, M-CSF (Yoshida et al., Nature 345: 442-444, 1990).

Thus, there remains a need in the art to identify new agents and methods for preventing or treating osteolysis or cancer metastasis, including osteolytic bone metastases. Metabolic bone diseases associated with relatively increased osteoclast activity, includes endocrinopathies (including hypercortisolism, hypogonadism, primary or secondary hyperparathyroidism, hyperthyroidism), hypercalcemia, deficiency states (including rickets/osteomalacia, scurvy, malnutrition), chronic diseases (including malabsorption syndromes, chronic renal failure (including renal osteodystrophy), chronic liver disease (including hepatic osteodystrophy)), drugs (including glucocorticoids (glucocorticoid-induced osteoporosis), heparin, alcohol), and hereditary diseases (including osteogenesis imperfecta, homocystinuria), cancer, osteoporosis, osteopetrosis, inflammation of bone associated with arthritis and rheumatoid arthritis, periodontal disease, fibrous dysplasia, and/or Paget's disease.

M-CSF plays a more general role in formation of cancer metastasis. Studies of M-CSF null mutant mice demonstrated that M-CSF plays an important role in mammary tumor progression to metastasis. M-CSF regulates these processes through the recruitment and regulation of macrophages, cells that become associated with mammary tumors and the terminal end buds at the end of the growing ducts. This phenomenon suggests that the tumors subvert normal developmental processes to allow invasion into the surrounding stroma, a process that gives the tumor access to the vasculature and consequently the promotion of metastasis. In addition, soluble M-CSF secreted from the tumor acts to divert antitumor macrophage responses and suppresses the differentiation of mature tumor-antigen-presenting dendritic cell (Lin et al., J. Exp.Med, 2002).

Chemokine (C-C Motif) Ligand 2 (CCL2) (Alt.: Monocyte Chemoattractant Protein-1 (MCP-1))

The chemoattractant cytokines, termed as chemokines, are a large family of low molecular weight proteins that share the ability to stimulate directed cell migration [Schall, Cytokine 3:165-183 (1991); Murphy, Rev Immun 12:593-633 (1994)]. Chemokines have been implicated as important mediators of allergic, inflammatory and autoimmune disorders and diseases, such as asthma, atherosclerosis, glomerulonephritis, pancreatitis, restenosis, rheumatoid arthritis, diabetic nephropathy, pulmonary fibrosis, multiple sclerosis, and transplant rejection. Accordingly, the use of antagonists of chemokine function may help reverse or halt the progression of these disorders and diseases.

With few exceptions, chemokines have four conserved cysteine residues that form disulfide bonds within the chemokine proteins. Two major chemokine subfamilies have been classified based on the chromosomal localization of the chemokine genes and the relative position of the first two cysteine residues (Van Collie et al., Cytokine Growth Factor Rev 10:61-86 (1999)). Monocyte chemoattractant protein-1 (CCL-2) is a member of the C-C class of the beta chemokine family and one of the key factors involved in the initiation of inflammation. CCL-2 is typically secreted in the prevalent forms, 9 and 13 kDa, respectively, as a result of differential O-glycosylation. It triggers chemotaxis and transendothelial migration of monocytes to inflammatory lesions by interacting with the membrane CC chemokine receptor 2 (CCR2) in monocytes (O'Hayre et al., 2008). CCL-2 is secreted by fibroblasts, endothelial cells, vascular smooth muscle cells, monocytes, T cells, and other cell types that mediate the influx of cells to sites of inflammation (Conti and DiGioacchino, 2001). CCL-2 expression has been observed in a large number of tissues during inflammation-dependent disease progression, including atherosclerosis (Shin et al., 2002), arthritis (Taylor et al., 2000) and cancer (O'Hayre et al., 2008). In these cases, the influx of macrophages into these tissues has been suggested to exacerbate the diseases. Thus, the expression of CCL-2, which is likely to be critical for fighting infectious disease, must be tightly regulated.

CCL-2 In Diseases

Elevated expression of CCL-2 has been observed in a number of chronic inflammatory diseases [Proost et al., Int J Clin Lab Res 26:211-223 (1996); Taub, D. D. Cytokine Growth Factor Rev 7:355-376 (1996)] including, but not limited to, rheumatoid arthritis [Robinson et al., Clin Exp Immunol 101: 398-407 (1995); Hosaka et al., ibid. 97:451-457 (1994); Koch et al., J Clin Invest 90:772-779 (1992); Villiger et al., J Immunol 149:722-727 (1992)], asthma [Hsieh et al., J Allergy Clin Immunol 98:580-587 (1996); Alam et al., Am J Respir Crit Care Med 153:1398-1404 (1996); Kurashima et al., J Leukocyte Biol 59:313-316 (1996); Sugiyama et al., Eur Respir J 8:1084-1090 (1995)], and atherosclerosis [Yla-Herttuala et al., Proc Natl Acad Sci USA 88:5252-5256 (1991); Nelken et al., J Clin Invest 88:1121-1127 (1991)].

CCL-2 appears to play a significant role during the early stages of allergic responses because of its ability to induce mast cell activation and LTC4 release into the airway, which directly induces AHR (airways hyper-responsiveness) [Campbell et al., J Immunol 163:2160-2167 (1999)].

CCL-2 has been found in the lungs of patients with idiopathic pulmonary fibrosis and is thought to be responsible for the influx of mononuclear phagocytes and the production of growth factors that stimulate mesenchymal cells and subsequent fibrosis [Antoniades et al., Proc Natl Acad Sci USA 89:5371-5375 (1992)]. In addition, CCL-2 is also involved in the accumulation of monocytes in pleural effusions implicated in both *Mycobacterium tuberculosis* infection and malignancy [Strieter et al., J Lab Clin Med 123:183-197 (1994)].

CCL-2 has also been shown to be constitutively expressed by synovial fibroblasts from rheumatoid arthritis patients, and its levels are higher in rheumatoid arthritis joints compared to normal joints or those from other arthritic diseases [Koch et al., J Clin Invest 90:772-779 (1992)]. These elevated levels of CCL-2 are probably responsible for the monocyte infiltration into the synovial tissue. CCL-2 also plays a critical role in the initiation and development of atherosclerotic lesions. CCL-2 is responsible for the recruitment of monocytes into atherosclerotic areas, as shown by immunohistochemistry of macrophage-rich arterial wall [Yla-Herttuala et al., Proc Natl Acad Sci USA 88:5252-5256 (1991); Nelken et al., J Clin Invest 88:1121-1127 (1991)] and anti-CCL-2 antibody detection [Takeya et al., Human Pathol 24:534-539 (1993)]. LDL-receptor/CCL-2-deficient and apoB-transgenic/CCL-2-deficient mice show significantly less lipid deposition and macrophage accumulation throughout their aortas compared with wild-type CCL-2 strains [Alcami et al., J Immunol 160: 624-633 (1998); Gosling et al., J Clin Invest 103:773-778 (1999); Gu et al., Mol. Cell. 2:275-281 (1998); Boring et al., Nature 394:894-897 (1998). Other inflammatory diseases marked by specific site elevations of CCL-2 include multiple sclerosis (MS), glomerulonephritis, and stroke. Together, these findings infer CCL-2 as a therapeutic target in the treatment of inflammatory disease and strongly suggest that the discovery and development of novel compounds that block or down-regulate CCL-2 activity would be highly beneficial in treating inflammatory diseases.

Interleukine-6 (IL-6)

IL-6 is a multifunctional cytokine originally identified as a T cell-derived factor that causes the terminal maturation of antigen-stimulated immature B-cells into immunoglobulin-producing plasma cells [Hirano T, Taga T, Nakano N, Yasukawa K, Kashiwamura S, Shimizu K, et al. Proc Natl Acad Sci USA 1985; 82: 5490-4]. A number of cell types produce IL-6, including T-cells, B-cells, monocytes, fibroblasts, keratinocytes, endothelial cells, mesangial cells and bone marrow stroma cells [Kawano M, Hirano T, Matsuda T, Taga T, Horii Y, Iwato K, et al. Nature 1988; 332: 83-5]. IL-6 also has a wide range of responder cells, including B-cells, T-cells, hepatocytes, hemotopoietic precursor cells, neural cells, epidermal keratinocytes, mesangial cells, and osteoclasts [Adachi et al. Current Pharmaceutical Design, 2008, 14, 1217-1224]. IL-6 functions as an immune regulator, acute phase protein inducer, cell differentiation factor, cell growth factor, and bone metabolism regulator against these effector cells. Additionally, IL-6 induces C-reactive protein (CRP) and serum amyloid A (SAA) on hepatocytes [Adachi et al. Current Pharmaceutical Design, 2008, 14, 1217-1224]. Both of these proteins are important markers of inflammation and are used clinically in monitoring patients suffering from inflammatory conditions. Recently, IL-6 has been implicated in the balance of Th17 and regulatory T cells has made the novel focus in immunology [Tato C M, O'Shea J J. Nature 2006; 441: 166-8.]. Given that aberrant helper T cell regulation is observed in chronic inflammatory states in humans, this action may confer superiority to anti-IL-6 treatments over approaches targeting other inflammatory cytokines.

IL-6 In Inflammatory Diseases

IL-6 is one of the key regulators of the inflammatory responses and induces the final maturation of B-cells into immunoglobulin-producing cells [Adachi et al. Current Pharmaceutical Design, 2008, 14, 1217-1224]. Owing to these properties, IL-6 is a pivotal molecule in the pathogenesis of several chronic inflammatory diseases, such as Castleman's disease, rheumatoid arthritis (RA), juvenile idiopathic arthritis, and Crohn's disease [Adachi et al. Current Pharmaceutical Design, 2008, 14, 1217-1224]. These diseases are often refractory to conventional therapies such as corticosteroids and immunosuppressants. Additionally, IL-6 overproduction plays an important pathological role in several neoplasms, including high-grade multiple myelomas [17-19] and malignant mesotheliomas [20, 21]. The paraneoplastic syndrome of mesothelioma including immunosuppression, cachexia, thrombocytosis, and amyloidosis, is related to IL-6 overproduction [Nakano et al. Br J Cancer 1998; 77: 907-912; Fitzpatrick et al. Am J Respir Cell Mol Biol 1995; 12: 455-60]. As such, anti-IL-6 treatment may both alleviate the clinically devastating paraneoplastic syndrome and suppress tumor growth. Thus, therapeutics targeting IL-6 show high potential for the treatment of inflammatory conditions and malignancies.

There is therefore a need to develop agents which can either down-regulate expression of genes such as M-CSF, G-CSF, CCL-2 and IL-6, or up-regulate genes such as M-CSF, GCSF, CCL-2 and IL-6 for use in the treatment of diseases wherein the modulation of expression of those factors will be beneficial. As is apparent herein, it may also be desirable for such agents to modulate the expression of other immune-related genes, such as Bcl2l1, Cd40, Nos2, Socs1, Stat1, and Cxcr3.

SUMMARY OF INVENTION

The present invention employs a microRNA-155 modulator, for use in modulating, such as inhibiting or enhancing (or supplementing) the function (or activity) of a microRNA, and thereby modulating, such as inhibiting (or suppressing) or enhancing, the expression of one or more cytokines, such as pro-inflammatory cytokines (target genes).

The present invention employs a microRNA-155 modulator, for use in modulating, such as inhibiting or enhancing (or supplementing) the function (or activity) of a microRNA, and thereby modulating, such as inhibiting (or suppressing) or enhancing, the expression of one or more genes selected from the group consisting of CSF, such as G-CSF, GM-CSF and/or M-CSF, Bcl2l1, Ccl2, Cd40, IL6, Nos2, Socs1, Stat1, and Cxcr3, in a cell.

The present invention employs a microRNA-155 modulator, for use in modulating, such as inhibiting or enhancing (or supplementing) the function (or activity) of a microRNA, and thereby modulating, such as inhibiting (or suppressing) or enhancing, the expression of one or more genes selected from the group consisting of CSF, such as G-CSF, GM-CSF and/or M-CSF, Ccl2, and IL6 in a cell.

The present invention employs a microRNA-155 inhibitor, for use in inhibiting the function of microRNA-155, and thereby reducing the expression of one or more cytokines, such as pro-inflammatory cytokines (target genes).

The present invention employs a microRNA-155 inhibitor, for use in inhibiting the function of microRNA-155, and thereby reducing the expression of one or more genes selected from the group consisting of CSF, such as G-CSF, GM-CSF and/or M-CSF, Bcl2l1, Ccl2, Cd40, IL6, Nos2, Socs1, and Stat1, in a cell.

The present invention employs a microRNA-155 inhibitor, for use in inhibiting the function of microRNA-155, and thereby reducing the expression of one or more genes selected from the group consisting of one or more genes selected from the group consisting of CSF, such as G-CSF, GM-CSF and/or M-CSF, Ccl2, and IL6 in a cell.

The present invention employs a microRNA-155 mimic, for use in enhancing or supplementing the function or activity of a microRNA, and thereby enhancing the expression of one or more cytokines, such as pro-inflammatory cytokines (target genes).

The present invention employs a microRNA-155 mimic, for use in enhancing or supplementing the function or activity of a microRNA, and thereby enhancing the expression of one or more genes selected from the group consisting of CSF, such as G-CSF, GM-CSF and/or M-CSF, Bcl2l1, Ccl2, Cd40, IL6, Nos2, Socs1, and Stat1, in a cell.

The present invention employs a microRNA-155 mimic, for use in enhancing or supplementing the function or activity of a microRNA, and thereby enhancing the expression of one or more genes selected from the group consisting of CSF, such as G-CSF, GM-CSF and/or M-CSF, Ccl2, and IL6 in a cell.

The invention provides a method of down-regulating (the expression of) one or more cytokines, such as pro-inflammatory cytokines (target genes) in a cell, said method comprising administering a microRNA 155 inhibitor to the cell.

The invention provides a method of down-regulating (the expression of) one or more genes selected from the group consisting of CSF, such as G-CSF, GM-CSF and/or M-CSF, Bcl2l1, Ccl2, Cd40, IL6, Nos2, Socs1, and Stat1, in a cell, said method comprising administering a microRNA 155 inhibitor to the cell.

The invention provides a method of down-regulating (the expression of) one or more genes selected from the group consisting of CSF, such as G-CSF, GM-CSF and/or M-CSF, Ccl2, and IL6 in a cell.

The invention provides a method of simultaneous down-regulation of G-CSF, M-CSF, CCL2 and IL-6 in a cell, said method comprising administering a microRNA 155 inhibitor to the cell.

The present invention employs a microRNA-155 inhibitor, for use in inhibiting the function of microRNA-155, and thereby enhancing the expression of Cxcr3, in a cell.

The present invention employs a microRNA-155 mimic, for use in enhancing or supplementing the function or activity of microRNA-155, and thereby suppressing the expression of Cxcr3 in a cell.

The invention provides a method of up-regulating (the expression of) Cxcr3 in a cell, said method comprising administering a microRNA-155 inhibitor to the cell.

The invention provides for a method of modulating the expression of one or more cytokines, such as pro-inflammatory cytokines (target genes), in a cell, said method comprising administering a modulator of microRNA-155 to the cell.

The invention provides a method of down-regulating (the expression of) one or more genes selected from the group consisting of CSF, such as G-CSF, GM-CSF and/or M-CSF, Ccl2, and IL6 in a cell.

The invention provides for a method of modulating the expression of one or more genes selected from the group consisting of CSF, such as G-CSF, GM-CSF and/or M-CSF, Bcl2l1, Ccl2, Cd40, IL6, Nos2, Socs1, Stat1, and Cxcr3, in a cell, said method comprising administering a modulator of microRNA-155 to the cell.

Suitably, when added to a cell, the microRNA modulator is administered to the cell in an amount effective to modulate the expression of the of one or more target genes, such as a target gene selected from the group consisting of CSF, such as G-CSF, GM-CSF and/or M-CSF, Bcl2l1, Ccl2, Cd40, IL6, Nos2, Socs1, Stat1, and Cxcr3.

Suitably, when added to a cell, the microRNA modulator is administered to the cell in an amount effective to modulate the expression of the of one or more target genes, such as a target gene selected from the group consisting of CSF, such as G-CSF, GM-CSF and/or M-CSF, Ccl2, and IL6 in a cell.

The invention provides for a modulator of microRNA-155 for use for modulating the expression of one or more cytokines, such as proinflammatory cytokines, in a cell, a tissue or an organism, such as a mammal, such as a human being.

The invention provides for a modulator of microRNA-155 for use for modulating the expression of one or more genes selected from the group consisting of CSF, such as G-CSF, GM-CSF and/or M-CSF, Bcl2l1, Ccl2, Cd40, IL6, Nos2, Socs1, Stat1, and Cxcr3, in a cell, a tissue or an organism, such as a mammal, such as a human being.

The invention provides for a modulator of microRNA-155 for use for modulating the expression of one or more genes selected from the group consisting of CSF, such as G-CSF, GM-CSF and/or M-CSF, and/or M-CSF, Ccl2, and IL6 in a cell.

The invention provides for an inhibitor of microRNA-155 for use for modulating the expression of one or more genes selected from the group consisting of CSF, such as G-CSF, GM-CSF and/or M-CSF, Bcl2l1, Ccl2, Cd40, IL6, Nos2, Socs1, Stat1, and Cxcr3, in a cell.

The invention provides for an inhibitor of microRNA-155 for use for modulating the expression of one or more genes selected from the group consisting of CSF, such as G-CSF, GM-CSF and/or M-CSF, Ccl2, and IL6 in a cell.

The present invention employs a microRNA modulator, for use in modulating, such as inhibiting or enhancing (or supplementing) the function (or activity) of a microRNA, and thereby modulating, such as inhibiting or enhancing, the expression of one or more colony stimulatory factor of factors, such as G-CSF, GM-CSF and/or M-CSF, in a cell.

The present invention employs a microRNA-155 inhibitor, for use in inhibiting the function of microRNA-155, and thereby reducing the expression of one or more colony stimulatory factor, such as G-CSF, GM-CSF and/or M-CSF, in a cell.

The present invention employs a microRNA-155 mimic, for use in enhancing or supplementing the function or activity of a microRNA, and thereby enhancing the expression of one or more colony stimulatory factor, such as G-CSF, GM-CSF and/or M-CSF, in a cell.

The invention provides a method of down-regulating one or more colony stimulatory factor, such as G-CSF, GM-CSF and/or M-CSF in a cell, said method comprising administering a microRNA inhibitor to the cell.

The invention provides for a method of modulating the expression of CSF, such as one or more of G-CSF, GM-CSF and/or M-CSF, in a cell, said method comprising administering a modulator of microRNA-155 to the cell.

Suitably, when added to a cell, the microRNA modulator is administered to the cell in an amount effective to modulate the expression of the one or more CSF factors, such as G-CSF, GM-CSF and/or M-CSF.

The invention provides a method of modulating the concentration of white blood cells, such as granulocytes and/or macrophages and/or eosinophils in a subject, said method comprising the step of administering of a modulator of microRNA-155 to said subject.

The invention provides a method of reducing the concentration of white blood cells, such as granulocytes and/or macrophages and/or eosinophils in a subject, said method comprising the step of administering of an inhibitor of microRNA-155 to said subject.

The invention provides a method of enhancing the concentration of white blood cells, such as granulocytes and/or macrophages and/or eosinophils in a subject, said method comprising the step of administering of a microRNA-155 mimic to said subject.

The invention provides for a modulator of microRNA-155 for use for modulating the expression of one or more CSF, such as G-CSF, GM-CSF and/or M-CSF, in a cell, a tissue or a organism, such as a mammal, such as a human being.

The invention provides for an inhibitor of microRNA-155 for use for down-regulating one or more CSF, such as G-CSF, GM-CSF and/or M-CSF, in a cell.

The invention provides for a microRNA-155 mimic for use for up-regulating one or more CSF in a cell, such as M-CSF, GM-CSF and/or G-CSF.

The invention provides for a microRNA-155 mimic for use for the treatment of an inflammatory disease.

The invention provides for the use of a microRNA-155 modulator in the preparation of a medicament for the treatment of an inflammatory disease.

The invention provides for a pharmaceutical composition comprising a modulator of microRNA-155, at least one further anti-inflammatory agent, and a pharmaceutical diluents, carrier or adjuvant.

The invention provides for a method of enhancing white blood cell count in a patient, such as a chemotherapy patient, said method comprising the step of administering a modulator of microRNA-155, such as the pharmaceutical composition of the invention, to said patient, such as during or subsequent to chemotherapy treatment.

BRIEF DESCRIPTION OF FIGURES

FIG. 1. LPS-mediated induction of miR-155 in cultured mouse Raw264.7 macrophages.

Figure 2A:
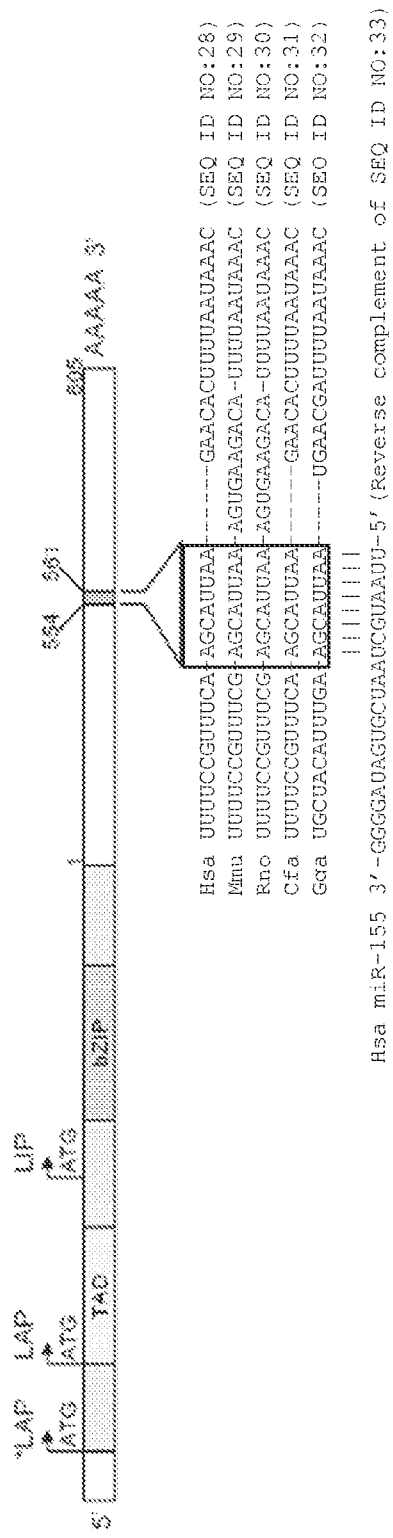
Figure 2B:
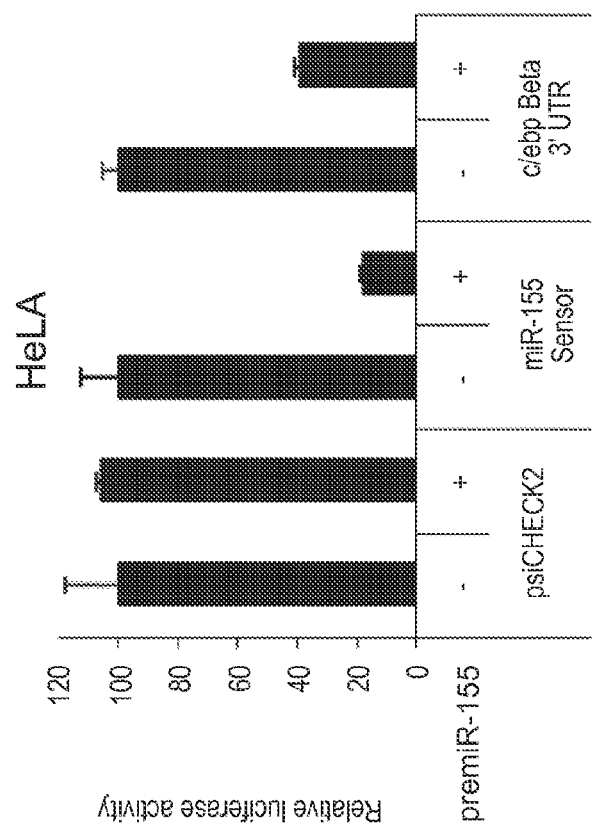

(A). Raw264.7 cells were stimulated with the indicated concentrations of LPS for 18 h and miR-155 expression was analyzed by qPCR. Values represent mean±SD. (B) Dual luciferase-reporter assay analysis of Raw264.7 cells transfected with either the empty *renilla*/firefly luciferase psiCHECK2 vector or the psiCHECK2 vector containing the miR-155 perfect match sequence in the 3' UTR of the *renilla*-luciferase transcript (miR-155 sensor). After transfection, the Raw264.7 cells were stimulated with the indicated concentrations of LPS for 18 h. Values represent mean±SD. (C) Dual luciferase-reporter assay analysis of Raw264.7 cells cotransfected with LNA-antimiR or LNA-control together with either the empty *renilla*/firefly luciferase psiCHECK2 vector (Data not shown) or the psiCHECK2 vector containing the miR-155 perfect match sequence in the 3' UTR of the *renilla* luciferase transcript (miR-155 sensor). Raw264.7 cells were stimulated with 100 ng/ml LPS for 18 h. Values represent mean±SD. Data are representative from three experiments each performed in triplicate.

FIG. 2. Translational repression of c/ebp Beta isoforms by miR-155.

(A) Schematic overview of the c/ebp Beta transcript. The boxed sequence area in the 3' UTR presents miR-155 (seed) target sequences in c/ebp Beta transcripts from human (Hsa) (SEQ ID NO:28) mouse (Mmu) (SEQ ID NO:29), rat (Rno) (SEQ ID NO:30), dog(Cfa) (SEQ ID NO:31), and chicken (Gga) ID NO:32). Also shown is the, sequence of human miR-155 (reverse complement of SEQ ID NO:33) indicating the interaction between its seed region and the seed targets. TAD =Transactivation domain, bZIP_=basic region leucine zipper domain, ATG_=translational start site; LAP_=liver-enriched transcriptional activation protein; LIP_=liver enriched transcriptional inhibitory protein. (B) Dual luciferase-reporter assay analysis of HeLa cells cotransfected with premiR-155_in combination with either the empty renilla-firefly luciferase psiCHECK2 vector, the psiCHECK2 vector (miR-155 sensor) containing the mik-155 perfect match sequence or the psiCHECK2 vector containing the c/ebp Beta 3' UTR in the 3' UTR of the renilla luciferase transcript. Values represent mean ±SD. Data are representative from three experiments each performed in triplicate. (C) Western blot analysis of c/ebp Beta LAP*, LAP and LIP in Raw264.7 cell lysates. Lysates from Raw264.7 cells cotransfected with 5 nM premiR155 together with either 5 nM LNA-control or 5 nM LNA-antimiR were subject to western analysis. Right panels: Columns showing quantification of LIP and LAP protein bands from the western analysis. (D) Western blot analysis of c/ebp Beta LAP*, LAP and LIP forms in Raw264.7 cell lysates. Raw264.7 cells were transfected with indicated concentrations of either LNA-control or LNA-antimiR and treated with LPS 100 ng/ml for 6 h. Bottom panels: Columns showing quantification of LIP and LAP protein bands from the western analysis. (E) Western blot analysis of c/ebp Beta LAP and LIP forms and PU.1 proteins in THP-1 cell lysates. Cell lysates from THP-1 cells cotransfected with 5 nM premiR-155 together with either 5 nM LNA-control or 5 nM LNA-antimiR were subjecte for Western analysis. Bottom panels: Columns showing quantification of Pu.1 and LIP protein bands from the western analysis. Data are representative of two experiments.

FIG. 3. miR-155 regulates c/ebp Beta in the splenocytes of LPS-treated mice.

(A) Confocal microscopy of the murine B cells (CD19) and monocyte/macrophages (CD11b) isolated from murine spleen after intravenous dosing with a 6-carboxyfluorescein (FAM)-labeled LNA oligonucleotide demonstrating that LNA oligonucleotides was readily taken up by these cells. (B) qPCR expression analysis of miR-155 expression in mouse splenocytes after intravenously dosing of either 25 mg/kg LNA-antimiR or 25 mg/kg LNA-control for three consecutive days. Spleen samples were dissected 2 h after 0.5 mg/kg LPS dosed intraperitonally. Values represent mean±SD from five mice in each group. P value (**; p<0.01) shown for two-sided Student's t-test. (C) Western blot analysis of c/ebp Beta LAP and LIP forms in mouse splenocytes after intravenously dosing of either 25 mg/kg LNA-antimiR or 25 mg/kg LNA-control for three consecutive days. Spleen samples were dissected 24 h after 0.5 mg/kg LPS dosed intraperitonally.

FIG. 4. miR-155 mediates regulation of granulocyte-colony stimulating factor (G-CSF).

(A) qPCR immune-array analysis of G-CSF transcripts normalized to β2-microglobulin transcripts. Raw264.7 cells were transfected with either 5 nM LNA-control or 5 nM LNA-antimiR and stimulated with 100 ng/ml LPS for 6 h. Values represent mean±SD from one experiment performed in five replicates. (B) qPCR expression analysis of G-CSF transcripts normalized to GAPDH transcripts after LPS-stimulation of THP-1 cells. THP-1 cells were cotransfected with 5 nM premiR-155 together with either 5 nM LNA-control or 5 nM LNA-antimiR before LPS stimulation for 6 h. Values represent mean±SD from one experiment performed in triplicates. P value (; p<0.01) shown for two-sided Student's t-test. (C) qPCR expression analysis of indicated transcripts normalised to GAPDH transcript in mouse splenocytes after intravenously dosing of either 25 mg/kg LNA-antimiR or 25 mg/kg LNA-control for three consecutive days. Spleen samples were dissected 2 h after 0.5 mg/kg LPS dosed intraperitonally. Values represent mean±SD from five mice in each group. P value (*; p<0.001) shown for two-sided Student's t-test. (D) left panel, Western blotting analysis of Raw264.7 cell lysates 24 h after transfection with either pCDNA3 or pCDNA3-LIP vectors, (C) right panel, qPCR expression analysis of G-CSF transcripts normalised to GAPDH transcripts after transfection of Raw264.7 cells with pCDNA3 or pCDNA3-LIP vectors. 24h after transfection the cells were stimulated with 100 ng/ml LPS for 6 h. Values represent mean±SD. P value (***; p<0.001) shown for two-sided Student's t-test from one experiment performed in triplicate.

Figure 5:
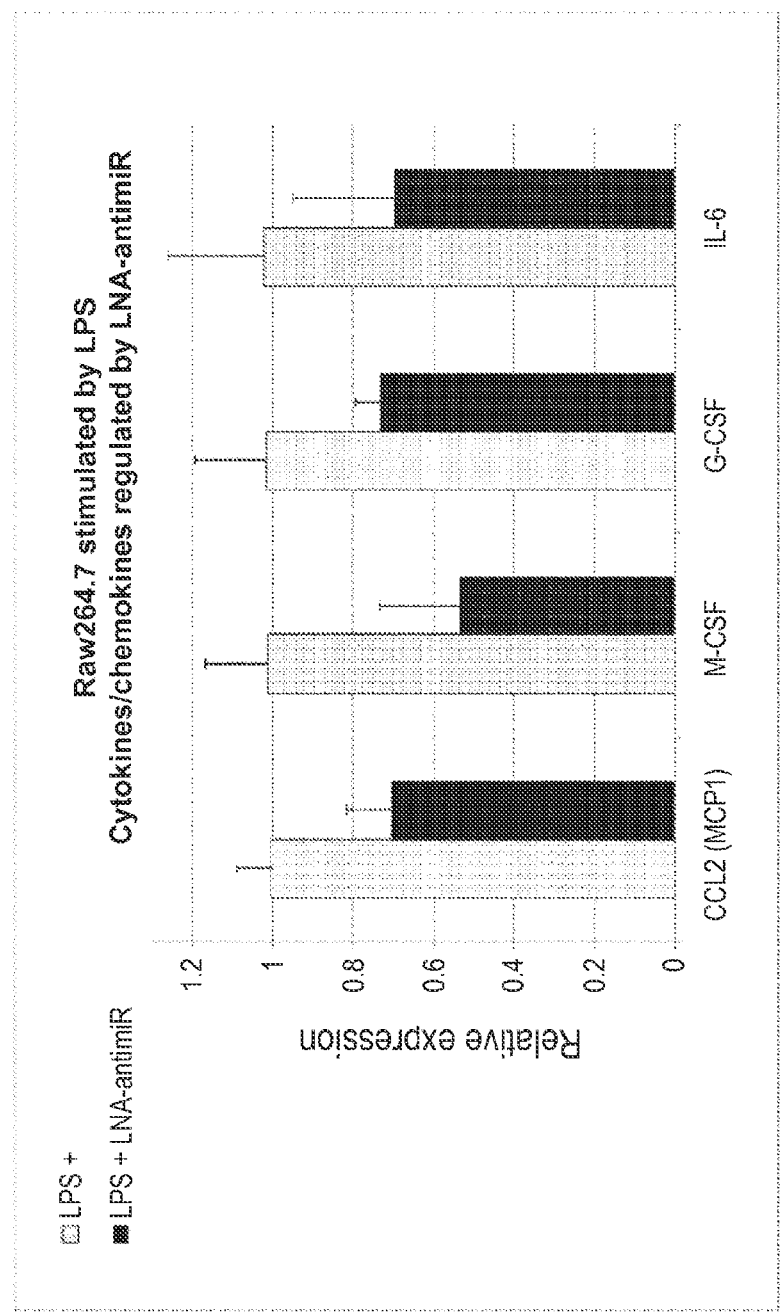

FIG. 5. Identification of CCL2 (Mcp-1), IL-6, M-CSF (Csf1) and G-CSF (Csf3), as miR-155 regulated transcripts. qPCR immune-array analysis of CCL2, IL-6, G-CSF and M-CSF transcripts normalized to β2-microglobulin transcripts. Raw264.7 cells were transfected with empty vehicle (LPS+) or 5 nM LNA-antimiR (LPS+LNA-antimiR) before stimulation with 100 ng/ml LPS for 6 h. Values represent mean±SD from one experiment performed in five replicates.

FIG. 6. Table 1. Identification of G-CSF as a miR-155 regulated transcript. Expression profiling data from RNA samples extracted from mouse Raw264.7 cells either untreated (No LPS), stimulated with 100 ng/ml LPS for 6 h (LPS+Mock) or transfected with either 5 nM LNA-antimiR-155 (SPC3989) (LPS+antimiR) or 5 nM LNA mismatch control (SPC4077) (LNA-control). The expression levels of the Csf3 gene encoding Granulocyte colony-stimulating factor (G-CSF) is shown in bold. All transcripts are normalized to β2-microglobulin transcripts.

DETAILED DESCRIPTION OF INVENTION

Modulation of Expression of the Target Genes, Such as Colony-Stimulating Factors The microRNA-155 modulators described herein have been found to be potent modulators of a group of immune related genes, including cytokines such as pro-inflammatory cytokines, CSF, such as G-CSF, GM-CSF, M-CSF as well as other genes such as Bcl2l1, Ccl2, Cd40, IL6, Nos2, Socs1, Stat1, and Cxcr3. Suppression of microRNA-155 activity by the use of an antimiR-155 resulted in decreased expression of CSF, such as G-CSF, GM-CSF, M-CSF, Bcl2l1, Ccl2, Cd40, IL6, Nos2, Socs1, and Stat1, and enhanced expression of Cxcr3. Use of a microRNA-155 mimic resulted in enhanced expression of CSF, such as G-CSF, GM-CSF, M-CSF, Bcl2l1, Ccl2, Cd40, IL6, Nos2, Socs1, and Stat1, and decreased expression of Cxcr3. MicroRNA-155 antimiR and mimics may therefore be used to modulate the expression of one or more, of even all, of these genes in a cell.

In some embodiments, the target gene or genes, is a gene encoding for a cytokine, such as a pro-inflammatory cytokine.

Suitably the target gene mRNA does not contain a microRNA

The "target gene(s)" referred to herein may therefore be one or more genes selected from the group consisting of CSF, such as G-CSF, GM-CSF, M-CSF, Bcl2l1, Ccl2, Cd40, IL6, Nos2, Socs1, and Stat1, and Cxcr3.

Preferred target genes include one or more or all the colony stimulating factors (CSFs), such as CSF1, CSF2 and or CSF3, optionally with one or more of Bcl2l1, Ccl2, Cd40, IL6, Nos2, Socs1, and Stat1, and Cxcr3.

In some aspects the target gene is the G-CSF gene—CSF3, such the human CSF3 gene (NCBI Accession records NM_172220, NM_172219 and/or NM_000759, Gene ID 1440, all hereby incorporated by reference), or the mouse CSF2 gene (NCBI Accession records NM_009971, M13926 hereby incorporated by reference).

In some aspects the target gene is the M-CSF gene—CSF1, such the human CSF1 (NCBI Accession records NM_000757, NM_172211.1, NM_172212.1 and/or NM_172210.1, GeneID: 1435, hereby incorporated by reference), or the mouse CSF1 gene (NCBI Accession records M_007778, M21952, S78392, BC066200, BC066205, BC066187, BC025593, all hereby incorporated by reference).

In some aspects the target gene is the GM-CSF gene—CSF2, such the human CSF2 (NCBI Accession records NM_000758.2 GeneID: 1437, hereby incorporated by reference), or the mouse CSF1 gene (NCBI Accession records, NM_009969, X03221, X05906, X03019, X02333 all hereby incorporated by reference).

In some aspect the target genes are CSF1 and CSF2; CSF2 and CSF3; CSF3 and CSF1; or CSF1, CSF2 and CSF3. The invention therefore provides a method for the simultaneous modulation of expression of multiple CSFs in the cell.

In some aspects the target gene is Cxcr3—GeneID: 2833 (human)—hereby incorporated by reference. In some aspects the target gene is BCL2L1—GeneID: 598 (human)—hereby incorporated by reference. In some aspects the target gene is CCL2—GeneID: 6347 (human)—hereby incorporated by reference. In some aspects the target gene is CD40—GeneID: 958 (human)—hereby incorporated by reference. In some aspects the target gene is STAT3—GeneID: 6774 (human)—hereby incorporated by reference. In some aspects the target gene is—GeneID: 6772 (human)—hereby incorporated by reference. In some aspects the target gene is SOCS1—GeneID: 8651 (human)—hereby incorporated by reference. In some aspects the target gene is—GeneID: 4843 (human)—hereby incorporated by reference. In some aspects the target gene is IL6—GeneID: 3569 (human)—hereby incorporated by reference.

In some aspects the modulation of expression of the target gene or genes is an enhancement of expression. In such cases, the administration of an effective amount of the microRNA-155 modulator, such as the microRNA-155 mimic, results in an increase in the concentration of the target gene mRNA and/or protein in the cell.

In some aspects the modulation of expression is an inhibition of expression. In such cases, the administration of an effective amount of a microRNA-155 inhibitor (antimiR), results in a decrease in the concentration of the target gene mRNA and/or protein in the cell.

In some embodiments the level of modulation (i.e. inhibition of enhancement) of the target gene expression is at least 10%, such as at least 20%, such as at least 30%, such as at least 40%, measured at the RNA or protein level.

Suitably, the oligomer is capable of modulating the expression of one or more of the target genes.

In some embodiments, the oligomer is capable of modulating the expression of CCAAT/enhancer binding protein beta (c/ebp Beta), (mRNA NM_005194.2 or NC_000020.9, protein NP_005185.2—NCBI Accession records are hereby incorporated by reference).

In some embodiments, the oligomer is capable of simultaneous downregulation of the expression of M-CSF, G-CSF, Ccl2 and IL-6.

In some embodiments, the oligomers of the invention effect inhibition of expression or enhance expression of the target gene by at least 10% or 20% compared to the normal expression level, more preferably at least a 30%, 40%, 50%, 60%, 70%, 80%, 90% or 95% compared to the normal expression level, as measured at the mRNA or protein level. In some embodiments, such modulation is seen when using between 0.04 and 25 nM, such as between 0.8 and 20 nM concentration of the compound of the invention. In the same or a different embodiment, the modulation of expression is less than 100%, such as less than 98%, less than 95%, less than 90%, less than 80%, such as less than 70%. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR.

The Cell

The cell is preferably a mammalian cell, such as an immune cell, such as a white blood cell, or precursor thereof. The term cell encompasses a population of cells, which may for example, be white blood cells.

In some embodiment the cell may be selected from the group consisting haematopoietic precursor cell, non-haematopoietic cell, white blood cell, monocytes, macrophages, splenocytes, neutrophils, eosinophils, basophils, dentritic cell, immature dentritic cell, myeloid cell, mature myeloid cell, fibroblast, and endothelial cell.

In some embodiments the cell may be a splenocyte. In some embodiments the cell may be a monocyte.

In some embodiments the cell may be a bone marrow cell or a bone marrow precursor cell.

In some preferred embodiments the cell is a macrophage or a macrophage precursor cell. In some embodiments the cell may be a neutrophil or a neutrophil precursor cell. In some embodiments the cell may be a basophil or a basophil precursor cell.

In some embodiments the cell is in vivo, such as in a subject or a patient. In some embodiments the cell is in vitro.

MicroRNA Modulator/Oligomer

A microRNA modulator is a compound which either inhibits (microRNA inhibitor) or supplements or enhances (microRNA mimic) the activity of a microRNA.

Preferably, the microRNA modulator, such as the microRNA inhibitor (antimiR) or microRNA mimic is an oligomeric compound (referred herein as an oligomer). Suitably, the oligomer is either homologous (miRNA mimic) or complementary (antimiR) to the microRNA sequence or a region thereof, although it is considered that the oligomer may comprise one or two mismatches with the corresponding microRNA sequence or reverse complement thereof.

In some embodiments, the present invention employs a microRNA inhibitor, such as an oligomer, for use in inhibiting the function of a microRNA, and thereby inhibiting the expression of one or more of the target genes, such as CSF(s) in a cell.

The term "oligomer" in the context of the present invention, refers to a molecule formed by covalent linkage of two or more nucleotides (i.e. an oligonucleotide). The oligomer, is some embodiments such as the antimiR oligomers, may consists or comprises of a contiguous nucleotide sequence of between 6-30 nucleotides in length. The length of the oligomer or contiguous nucleotide sequence thereof may be 6, 7, 8, 9, 10, 11, 12, 13, 14, 15, 16, 17, 18, 19, 20, 21, 22, 23, 24, 25, 26, 27, 28, 29 or 30 nucleotides in length. It will be recognised that in relation to microRNA mimics the size of the oligomer may longer, such as up to 70, up to 80, up to 90, or up to 100 nucleotides in length as premicroRNA mimics may be utilised which are processed in the cell to form a functional mature microRNA mimic. In some aspects, microRNA mimics may be at least 15, at least 16, at least 17, at least 18, at least 18, at least 20, at least 21 nucleotides in length.

gomer is essentially not double stranded, such as is not a siRNA. In various embodiments, the oligomer may consist entirely of the contiguous nucleotide region. Thus, in some embodiments, the oligomer is not substantially self-complementary.

In some embodiment, the contiguous nucleotide sequence of the oligomer is between 6-12 nucleotides in length, such as 6, 7, 8, 9, 10, 11 or 12 nucleobase units, wherein at least 50% of the nucleobase units of the oligomer consists of nucleotide analogues, such as, when the oligomer is an antimiR, LNA nucleotide analogues.

In some embodiments, the 3' nucleobase of the antimiR oligomer corresponds to the 5' nucleotide of the seed region of the microRNA, and the antimiR comprises a contiguous nucleotide sequence which is fully complementary to the microRNA seed sequence, and optionally between 1 and 15 further nucleotides, such 1, 2, 3, 4, 5, 6, 7, 8, 9 or 10, such as one or two further nucleotides corresponding to the microRNA nucleotides 3' to the seed sequence.

In one embodiment, the oligomer does not comprise a nucleotide which corresponds to the first nucleotide present in the microRNA sequence counted from the 5' end.

In one embodiment, at least 60%, 65%, 70%, 75%, 80%, 85%, 90%, 95% or all of the nucleotide units of the contiguous nucleotide sequence are nucleotide analogue units, such as high affinity nucleotide analogues. High affinity nucleotide analogues are nucleotide analogues which result in oligonucleotides which has a higher thermal duplex stability with a complementary RNA nucleotide than the binding affinity of an equivalent DNA nucleotide. This is typically determined by measuring the $T_m$.

In one embodiment, the nucleotide analogue units present in the contiguous nucleotide sequence are selected from the group consisting of 2'-O_alkyl-RNA unit, 2'-OMe-RNA unit, 2'-amino-DNA unit, 2'-fluoro-DNA unit, LNA unit, PNA unit, HNA unit, INA unit, and a 2'MOE RNA unit.

MicroRNA-155

The microRNA is preferably microRNA-155 or precursor thereof, such as a mammalian microRNA-155 such as the human or mouse microRNA-155, the pre-miR and mature miR-155 sequences are provided below:

```
>hsa-mir-155 MI0000681
                                                         (SEQ ID NO 1)
CUGUUAAUGCUAAUCGUGAUAGGGGUUUUUGCCUCCAACUGACUCCUACAUAUUAGCAUUAACAG >hsa-miR-155 MIMAT0000646
                                                         (SEQ ID NO 2)
UUAAUGCUAAUCGUGAUAGGGGU >mmu-mir-155 MI0000177
                                                         (SEQ ID NO 3)
CUGUUAAUGCUAAUUGUGAUAGGGGUUUUGGCCUCUGACUGACUCCUACCUGUUAGCAUUAACAG >mmu-miR-155 MIMAT0000165
                                                         (SEQ ID NO 4)
UUAAUGCUAAUUGUGAUAGGGGU
The seed regions - from position 2-7 or 8 of the mature microRNAs are shown)
```

In various embodiments, the oligomer may not comprise RNA (units), for example is some antimiR embodiments. The oligomer may be, in some embodiment, a linear molecule or is synthesised as a linear molecule. In some embodiment, theoligomer may be a single stranded molecule, and preferably does not comprise short regions of, for example, at least 3, 4 or 5 contiguous nucleotides, which are complementary to equivalent regions within the same oligomer (i.e. duplexes)— in this regards, the oligomer may, in some aspects, not be (essentially) double stranded. In some embodiments, the oligomer is essentially not double stranded, such as is not a MicroRNA Mimics The microRNA-155 mimics may inhibit the expression of Cxcr3 in a cell.

The microRNA-155 mimics may enhance the expression of the following target genes in a cell—CSF, such as G-CSF, GM-CSF and/or M-CSF, Bcl2l1, Ccl2, Cd40, IL6, Nos2, Socs1, and Stat1.

MicroRNA-155 mimics may be used to enhance the expression of pro-inflammatory cytokines in a cell.

MicroRNA mimics may be in the form of mimics of the mature microRNA or may be in the form or pre-microRNA mimics, such as the Pre-miR™ miRNA Precursor Molecules sold by Ambion.

In some embodiments, the present invention employs a microRNA mimic, such as an oligomeric compound (referred herein as an oligomer), for use in enhancing the expression of a colony stimulatory factor, such as G-CSF in a cell. Suitably, the enhancement of colony stimulatory factor in the cell is achieved via enhancing (such as supplementing) the microRNA activity in the cell.

A mimic may therefore be a compound which provides the microRNA activity, although it may, in some embodiments, not be identical in structure to microRNA whose activity it 'mimics'—for example it may be an oligomer which has a contiguous sequence of nucleotides which are present in the respective microRNA sequence, but some or even all of the nucleotides may be nucleotide analogues rather than RNA units, and/or is some aspects the microRNA mimic may be comprise or consist of a contiguous nucleotide sequence which is of sufficient length and % homology to the microRNA so that it can specifically modulate the expression of the same target molecules as the microRNA.

MicroRNA mimics are, in some embodiments, oligomeric compounds which have (retain) the same sequence of nucleotides as a microRNA, such as SEQ ID NO 1, 2, 3 or 4, or in some embodiments a functional fragment thereof (in some embodiments, the microRNA mimic may be truncated, but it has sufficient length and homology to the microRNA to provide the specific mimetic activity). microRNA mimics typically retain at least the seed sequence of the microRNA.

In some embodiment, the microRNA mimic may be in the form of a double stranded molecule, where one of the strands is an oligomer with the same sequence of nucleotides as a microRNA, such as SEQ ID NO 1, 2, 3 or 4, or a fragment thereof, and the second strand is a strand which is complementary so that the two strands hybridise to form a miRNA (sRNA) silencing complex. Such miRNA duplexes may have one or both ends as 3' overhands, typically of between 1-3 nts. MicroRNA mimics against microRNAs, such as microRNA 155 are available from Thermo Scientific (e.g. Dharmacon Meridian Product C-300647-05).

The microRNA mimic is capable of supplementing the microRNA function, and therefore can be used to enhance the repression of mRNAs targeted by the microRNA, such as in the case of microRNA 155, the CCAAT/enhancer binding protein beta (c/ebp Beta). In some embodiment therefore, micro-RNA 155 mimics may be identified by their ability to enhance the repression of CCAAT/enhancer binding protein beta (c/ebp Beta).

The MicroRNA Inhibitor (Antimir)

The microRNA-155 antimiR have been found herein to enhance the expression of Cxcr3 in a cell.

The microRNA-155 antimiR have been found herein to inhibit the expression of the following target genes in a cell—CSF, such as G-CSF, GM-CSF and/or M-CSF, Bcl2l1, Ccl2, Cd40, IL6, Nos2, Socs1, and Stat1.

MicroRNA-155 inhibitors (antimiR) may be used to inhibit the expression of pro-inflammatory cytokines in a cell.

In some embodiments, the microRNA inhibitor is, or may comprise of, an oligomer of between 6 and 30 contiguous nucleotides in length. Suitably the microRNA inhibitor may be a single stranded oligomer which consists or comprises of a contiguous nucleotide sequence which is fully complementary to, or fully complementary to, a corresponding region of a sequence selected from any one of SEQ ID 1, 2, 3 or 4, or comprises no more than 1 or 2 mismatches with the reverse complement of a sequence selected from SEQ ID 1, 2, 3 or 4, or a corresponding region thereof. Whilst it is recognised that antimiR oligomers may consist or comprise of a contiguous nucleotide sequence which is complementary to the entire microRNA sequence (such as SEQ ID NO 2), shorter oligomers which are complementary to a sub-sequence of the microRNA sequence may be highly effective, especially when they comprise affinity enhancing nucleotide analogues, such as LNA units. The length of the contiguous nucleotide sequence of the oligomer may be, for instance, 6, 7, 8, 9, 10, 11, 12, 13, 14, 15, 16, 17, 18, 19, 20, 21, 22, or 23 consecutive nucleotides which are fully complementary to SEQ ID NO 2, or comprise no more than 1 or 2 mismatches with the reverse complement of SEQ ID NO 2, or sub-sequence thereof, and, preferably comprise a region which is fully complementary to the microRNA 155 seed region. We have found that heavily modified antimiRs are particularly effective—WO2007/112754, WO2007/112753, EP Application number 08104780, and U.S. provisional applications 60/979217 and U.S. 61/028062 provide microRNA inhibitors which may be used in the present invention.

In some embodiments, the contiguous nucleotide sequence consists of or comprises a sequence which is complementary (such as 100% complementary) to the seed sequence of said microRNA (i.e. a seedmer'), such as miR-155.

Preferably, the antimiR oligomer comprises nucleotide analogues, such as LNA, which form part of, or may form the entire contiguous nucleotide sequence.

In one embodiment the antimiR oligomer, at least 60%, 65%, 70%, 75%, 80%, 85%, 90%, 95% or all of the nucleobase units of the contiguous nucleotide sequence are Locked Nucleic Acid (LNA) nucleobase units. In one embodiment, all of the nucleobase units of the antimiR oligomer contiguous nucleotide sequence are LNA nucleobase units. In one embodiment the antimiR oligomer, the contiguous nucleotide sequence comprises or consists of 7, 8, 9 or 10, preferably contiguous, nucleotide analogue units, such as LNA nucleobase units.

Whilst it is envisaged that other nucleotide analogues, such as 2'-MOE RNA or 2'-fluoro nucleotides may be useful in the antimiR oligomers according to the invention, in some embodiments the oligomers have a high proportion, such as at least 50%, LNA nucleotides. In one embodiment, at least 75%, such as 80% or 85% or 90% or 95% or all of the internucleoside linkages present between the nucleobase units of the contiguous nucleotide sequence are phosphorothioate internucleoside linkages. In one embodiment, said oligomer is conjugated with one or more non-nucleobase compounds. In one embodiment, the oligomer is constituted as a prodrug.

The following table provides examples of microRNA-155 inhibitors which may be used:

| target: hsa-miR-155 MIMAT0000646-AntimiRs: | |
|---|---|
| 5'-CCCCtatcacgattagcaTTAA-3' | SEQ ID NO: 5 |
| 5'-ccccctaTCACGATTagcattaa-3' | SEQ ID NO: 6 |
| 5'-cCccTatCacGatTagCatTaa-3' | SEQ ID NO: 7 |
| 5'-TcAcgATtaGcAtTA-3' | SEQ ID NO: 8 |
| 5'-TcAcGATtaGCAtTA-3' | SEQ ID NO: 9 |
| 5'-ACGATtAGCAtTA-3' | SEQ ID NO: 10 |

| target: hsa-miR-155 MIMAT0000646-AntimiRs: | |
|---|---|
| 5'-GATtAGCaTTA-3' | SEQ ID NO: 11 |
| 5'-TC$^M$AC$^M$G$^M$ATTA$^M$GC$^M$AT$^M$TA-3' | SEQ ID NO: 12 |
| 5'-TC$^F$AC$^F$G$^F$ATT$^F$A$^F$GC$^F$AT$^F$TA-3' | SEQ ID NO: 13 |
| 5'-cCcCtAtCaCgAtTaGcAtTaa-3' | SEQ ID NO: 14 |
| 5'-tcAcgAttAgcAttAa-3' | SEQ ID NO: 15 |
| 5'-tCaCgAtTaGcAtTa-3' | SEQ ID NO: 16 |
| 5'-TcAcAATtaGCAtTA-3' | SEQ ID NO: 17 |
| 5'-TcAaCATtaGACtTA-3' | SEQ ID NO: 18 |
| 5'-TATGTAGGA-3' | SEQ ID NO: 19 |
| 5'-TTAGCATTA-3' | SEQ ID NO: 20 |
| 5'-TAGCATTA-3' | SEQ ID NO: 21 |
| 5'-AGCATTA-3' | SEQ ID NO: 22 |
| 5'-TATGTAGGA-3' | SEQ ID NO: 23 |
| 5'-ATGTAGGA-3' | SEQ ID NO: 24 |
| 5'-TGTAGGA-3' | SEQ ID NO: 25 |

Capital Letters without a superscript M or F, refer to LNA units. Lower case=DNA, except for lower case in bold=RNA. The LNA cytosines may optionally be methylated). Capital letters followed by a superscript M refer to 2'OME RNA units, Capital letters followed by a superscript F refer to 2'fluoro DNA units, lowercase letter refer to DNA.

The above oligos may in one embodiment be entirely phosphorothioate, but other nucleobase linkages as herein described bay be used. In one embodiment the nucleobase linkages are all phosphodiester.

The antimiR oligomers according to the invention, such as those disclosed in table 2 may, in some embodiments, consist or comprise a sequence of nucleotides 5'-3' selected form the group consisting of: LdLddL(L)(d)(d)(L)(d)(L)(d)(L)(L), LdLdLL(L)(d)(d)(L)(L)(L)(d)(L)(L), LMLMML(L)(M)(M)(L)(M)(L)(M)(L)(L), LMLMLL(L)(M)(M)(L)(L)(L)(M)(L)(L), LFLFFL(L)(F)(F)(F)(L)(F)(L)(F)(L)(L), LFLFLL(L)(F)(F)(L)(L)(L)(F)(L)(L), and every third designs such as; LdLdLdd(L)(d)(d)(L)(d)(d)(d)(L)(d)(d)(L)(d) 'dLddLd(d)(L)(d)(d)(L)(d)(d)(L)(d)(d)(L), ddLddL(d)(d)(d)(L)(d)(d)(L)(d)(d)(L)(d)(d), LMMLMM(L)(M)(M)(L)(M)(M)(L)(M)(M)(L)(M), MLMMLM(M)(L)(M)(M)(L)(M)(M)(L)(M)(M)(L), MMLMML(M)(M)(L)(M)(M)(L)(M)(M)(L)(M)(M), LFFLFF(L)(F)(F)(L)(F)(F)(L)(F)(F)(L)(F), FLFFLF(F)(L)(F)(F)(L)(F)(F)(L)(F)(F)(L), FFLFFL(F)(F)(L)(F)(F)(L)(F)(F)(L)(F)(F)(L)(F)(F), and dLdLdL(d)(L)(d)(L)(d)(L)(d)(L)(d)(L)(d) and an every second design, such as; LdLdLd(L)(d)(L)(d)(L)(d)(L)(d)(L)(d)(L), MLMLML(M)(L)(M)(L)(M)(L)(M)(L)(M)(L)(M), LMLMLM(L)(M)(L)(M)(L)(M)(L)(M)(L)(M)(L), FLFLFL(F)(L)(F)(L)(F)(L)(F)(L)(F)(L)(F), and LFLFLF(L)(F)(L)(F)(L)(F)(L)(F)(L)(F)(L); wherein L=LNA unit, d=DNA units, M=2'MOE RNA, F=2'Fluoro and residues in brackets are optional.

SiRNA Complexes

In some embodiments, the oligomer, may be a first oligomer, which may form part of a (double stranded oligomer) complex with a second oligomer which comprises a region which is complementary to the first oligomer, such as an siRNA.

Nucleotide Analogues

The term "nucleotide" as used herein, refers to a glycoside comprising a sugar moiety, a base moiety and a covalently linked phosphate group and covers both naturally occurring nucleotides, such as DNA or RNA, preferably DNA, and non-naturally occurring nucleotides comprising modified sugar and/or base moieties, which are also referred to as "nucleotide analogues" herein.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; Nucl. Acid Res., 1997, 25, 4429-4443 and Uhlmann; Curr. Opinion in Drug Development, 2000, 3 (2), 293-213, and in Scheme 1:

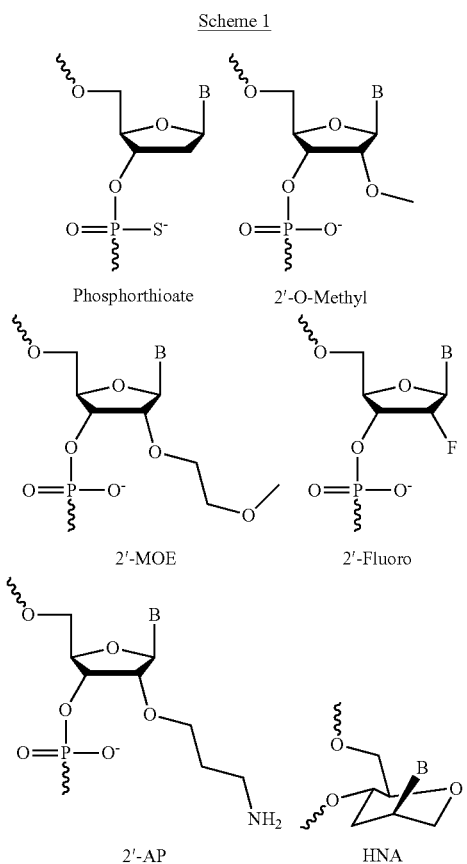

Scheme 1

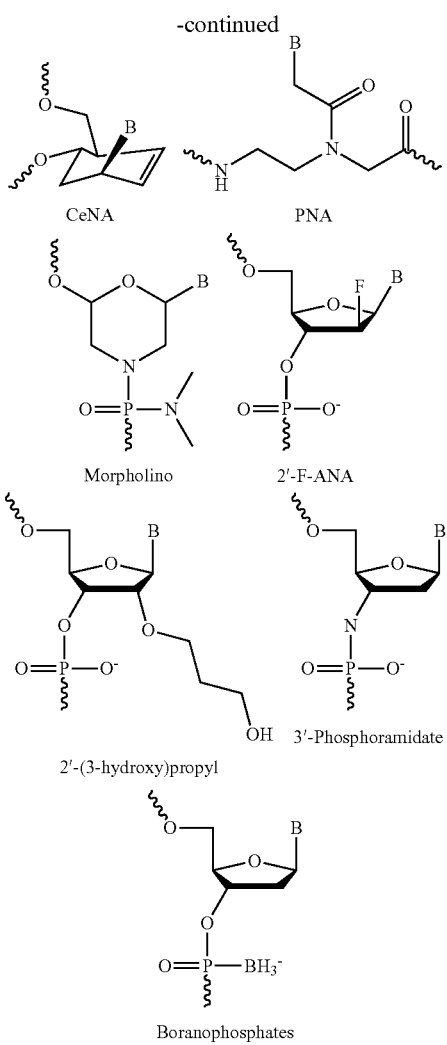

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by PCT/DK2006/000512 or are referenced therein.

Incorporation of affinity-enhancing nucleotide analogues in the oligomer, such as LNA or 2'-substituted sugars, can allow the size of the specifically binding oligomers to be reduced, and may also reduce the upper limit to the size of the oligomer before non-specific or aberrant binding takes place.

In some embodiments the oligomer comprises at least 2 nucleotide analogues. In some embodiments, the oligomer comprises from 3-8 nucleotide analogues, e.g. 6 or 7 nucleotide analogues. In the by far most preferred antimiR embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue for the antimiR oligomers is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid -Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the antimiR oligomer may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the antimiR oligomer comprises at least one Locked Nucleic Acid (LNA) unit, such as 1, 2, 3, 4, 5, 6, 7, or 8 LNA units, such as between 3-7 or 4 to 8 LNA units, or 3, 4, 5, 6 or 7 LNA units. In some embodiments, all the nucleotide analogues are LNA. In some embodiments, the antimiR oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-Cytosine. In some embodiments of the invention, the antimiR oligomer may comprise both LNA and DNA units. Preferably the combined total of LNA and DNA units is 10-25, preferably 10-20, even more preferably 12-16. In some embodiments of the invention, the nucleotide sequence of the antimiR oligomer, such as the contiguous nucleotide sequence consists of at least one LNA and the remaining nucleotide units are DNA units. In some embodiments the antimiR oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occuring a well as non-naturally occurring variants. Thus, "nucleobase" covers not only the known purine and pyrimidine heterocycles but also heterocyclic analogues and tautomeres thereof.

Examples of nucleotides include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleotides present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleotide analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a biradical 'bridge' between C2' and C4' of the ribose sugar ring—for example as shown as the biradical $R^{4*}$-$R^{2*}$ as described below.

The LNA used in the oligonucleotide compounds of the invention preferably has the structure of the general formula I

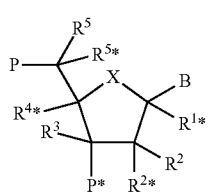

Formula 1 wherein for all chiral centers, asymmetric groups may be found in either R or S orientation;

wherein X is selected from —O—, —S—, —N($R^{N*}$)—, —C($R^6 R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a biradical consisting of 1-4 groups/atoms selected from —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; ; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^a R^b$)—C($R^a R^b$)—, C($R^a R^b$)—O—, C($R^a R^b$)—NR$^a$—, C($R^a R^b$)—S—, and C($R^a R^b$)—C($R^a R^b$)—O—, wherein each $R^a$ and $R^b$ may optionally be independently selected. In some embodiments, $R^a$ and $R^b$ may be, optionally independently selected from the group consisting of hydrogen and $C_{1-6}$alkyl, such as methyl, such as hydrogen.

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —CH$_3$, —CH$_2$—CH$_3$, —CH$_2$—O—CH$_3$, and —CH=CH$_2$. Suitably in some embodiments, either $R^5$ or $R^{5*}$ are hydrogen, where as the other group ($R^5$ or $R^{5*}$ respectively) is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(=O)$NJ_1J_2$, N(H)C(=NH)NR,$R_2$ or N(H)C(=X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$aminoalkyl, substituted $C_{1-6}$aminoalkyl or a protecting group. In some embodiments either $R^5$ or $R^{5*}$ is substituted $C_{1-6}$alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(=O)$NJ_1J_2$, N(H)C(=NH)$NJ_1J_2$ or N(H)C(O)N(H)$J_2$. In some embodiments each $J_1$ and $J_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH=CH— For all chiral centers, asymmetric groups may be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $0_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein Rc is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$) —O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$aminoalkyl or substituted $C_{1-6}$aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein Rc is $C_{1-12}$ alkyloxy. In some embodiments $R^{4*}$ and $R^{2*}$ together designate a biradical -$Cq_3q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, COOJ$_1$, CN, C—C(=O)NJ$_1$J$_2$, N(H)C(=NH)NJ$_1$J$_2$ or N(H)C(=X)=N(H)J$_2$ wherein X is O or S; and each of J$_1$ and J$_2$ is, independently, H, C$_{1-6}$ alkyl, C$_{2-6}$ alkenyl, C$_{2-6}$ alkynyl, C$_{1-6}$aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, R$^{1*}$, R$^2$, R$^3$, R$^5$, R$^{5*}$ are independently selected from the group consisting of hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl or substituted C$_{2-6}$ alkynyl, C$_{1-6}$alkoxyl, substituted C$_{1-6}$alkoxyl, acyl, substituted acyl, C$_{1-6}$aminoalkyl or substituted C$_{1-6}$ aminoalkyl. In some embodiments, R$^{1*}$, R$^2$, R$^3$, R$^5$, R$^{5*}$ are hydrogen. In some embodiments, R$^{1*}$, R$^2$, R$^3$ are hydrogen and one or both of R$^5$, R$^{5*}$ may be other than hydrogen as referred to above and in WO 2007/134181. In some embodiments R$^{4*}$ and R$^{2*}$ together designate a biradical (bivalent group) C(R$^a$R$^b$)—O—, wherein R$^a$ and R$^b$ are each independently halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxy, substituted C$_1$-C$_{12}$ alkoxy, OJ$_1$, SJ$_1$, SOJ$_1$, SO$_2$J$_1$, NJ$_1$J$_2$, N$_3$, CN, C(=O)OJ$_1$, C(=O)NJ$_1$J$_2$, C(=O)J$_1$, O—C(=O)NJ$_1$J$_2$, N(H)C(=NH)NJ$_1$J$_2$, N(H)C(=O)NJ$_1$J$_2$ or N(H)C(=S)NJ$_1$J$_2$; or R$^a$ and R$^b$ together are =C(q3)(q4); q$_3$ and q$_4$ are each, independently, H, halogen, C$_1$-C$_{12}$alkyl or substituted C$_1$-C$_{12}$ alkyl; each substituted group is, independently, mono or poly substituted with substituent groups independently selected from halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, OJ$_1$, SJ$_1$, NJ$_1$J$_2$, N$_3$, CN, C(=O)OJ$_1$, C(=O)NJ$_1$J$_2$, C(=O)J$_1$, O—C(=O)NJ$_1$J$_2$, N(H)C(=O)NJ$_1$J$_2$ or N(H)C(=S)NJ$_1$J$_2$ and; each J$_1$ and J$_2$ is, independently, H, C1-C$_6$ alkyl, substituted C1-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C1-C$_6$ aminoalkyl, substituted C1-C$_6$ aminoalkyl or a protecting group. Such compounds are disclosed in WO2009006478A, hereby incorporated in its entirety by reference.

In some embodiments, R$^{4*}$ and R$^{2*}$ form the biradical -Q-, wherein Q is C(q$_1$)(q$_2$)C(q$_3$)(q$_4$), C(q$_1$)=C(q$_3$), C[=C(q$_1$)(q$_2$)]—C(q$_3$)(q$_4$) or C(q$_1$)(q$_2$)—C[=C(q$_3$)(q$_4$)]; q$_1$, q$_2$, q$_3$, q$_4$ are each independently. H, halogen, C$_{1-12}$ alkyl, substituted C$_{1-12}$ alkyl, C$_{2-12}$ alkenyl, substituted C$_{1-12}$ alkoxy, OJ$_1$, SJ$_1$, SOJ$_1$, SO$_2$J$_1$, NJ$_1$J$_2$, N$_3$, CN, C(=O)OJ$_1$, C(=O)—NJ$_1$J$_2$, C(=O) J$_1$, —C(=O)NJ$_1$J$_2$, N(H)C(=NH)NJ$_1$J$_2$, N(H)C(=O)NJ$_1$J$_2$ or N(H)C(=S)NJ$_1$J$_2$; each J$_1$ and J$_2$ is, independently, H, C$_{1-6}$ alkyl, C$_{2-6}$ alkenyl, C$_{2-6}$ alkynyl, C$_{1-6}$ aminoalkyl or a protecting group; and, optionally wherein when Q is C(q$_1$)(q$_2$)(q$_3$)(q$_4$) and one of q$_3$ or q$_4$ is CH$_3$ then at least one of the other of q$_3$ or q$_4$ or one of q$_1$ and q$_2$ is other than H. In some embodiments, R$^{1*}$, R$^2$, R$^3$, R$^5$, R$^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, R$^{1*}$, R$^2$, R$^3$, R$^5$, R$^{5*}$ are independently selected from the group consisting of hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl or substituted C$_{2-6}$ alkynyl, C$_{1-6}$alkoxyl, substituted C$_{1-6}$alkoxyl, acyl, substituted acyl, C$_{1-6}$ aminoalkyl or substituted C$_{1-6}$ aminoalkyl. In some embodiments, R$^{1*}$, R$^2$, R$^3$, R$^5$, R$^{5*}$ are hydrogen. In some embodiments, R$^{1*}$, R$^2$, R$^3$ are hydrogen and one or both of R$^5$, R$^{5*}$ may be other than hydrogen as referred to above and in WO 2007/134181 or WO2009/067647 (alpha-L-bicyclic nucleic acids analogs).

In some embodiments the LNA used in the oligonucleotide compounds of the invention preferably has the structure of the general formula II:

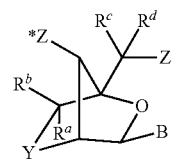

Formula II wherein Y is selected from the group consisting of —O—, —CH$_2$O—, —S—, —NH—, N(Re) and/or —CH$_2$—; Z and Z* are independently selected among an internucleotide linkage, R$^H$, a terminal group or a protecting group; B constitutes a natural or non-natural nucleotide base moiety (nucleobase), and R$^H$ is selected from hydrogen and C$_{1-4}$-alkyl; R$^a$, R$^b$ R$^c$, R$^d$ and R$^e$ are, optionally independently, selected from the group consisting of hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxycarbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkylcarbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH$_2$); and R$^H$ is selected from hydrogen and C$_{1-4}$-alkyl. In some embodiments R$^a$, R$^b$ R$^c$, R$^d$ and R$^e$ are, optionally independently, selected from the group consisting of hydrogen and C$_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

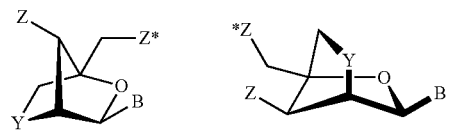

Specific exemplary LNA units are shown below:

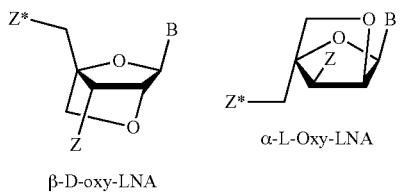

β-D-oxy-LNA    α-L-Oxy-LNA

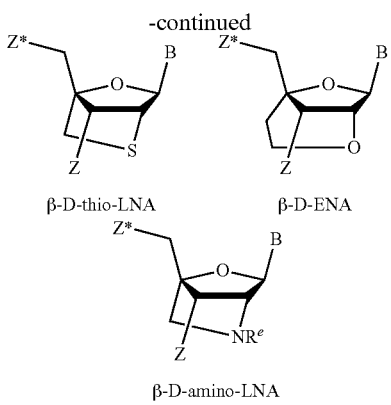

β-D-thio-LNA   β-D-ENA

β-D-amino-LNA

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Internucleotide Linkages

The terms "linkage group" or "internucleotide linkage" are intended to mean a group capable of covalently coupling together two nucleotides, two nucleotide analogues, and a nucleotide and a nucleotide analogue, etc. Specific and preferred examples include phosphate groups and phosphorothioate groups.

The nucleotides of the oligomer or contiguous nucleotides sequence thereof are coupled together via linkage groups. Suitably each nucleotide is linked to the 3' adjacent nucleotide via a linkage group.

Suitable internucleotide linkages include those listed within PCT/DK2006/000512, for example the internucleotide linkages listed on the first paragraph of page 34 of PCT/DK2006/000512 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

Conjugates

In the context the term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer may comprise both a polynucleotide region which typically consists of a contiguous sequence of nucleotides, and a further non-nucleotide region. When referring to the oligomer consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

Compositions

The oligomer may be used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference.

Applications and Medical Indications

The use of microRNA-155 modulators has been found to effect a range of targets, including cytokines, such as pro-inflammatory cytokines, such as CSFs. The modulators may therefore be used to simultaneously modulate several targets in the cell, and as such provides highly effective modulator of inflammatory responses, particularly those associated with inflammatory diseases, and autoimmune diseases.

The invention provides for a method of enhancing white blood cell count in a patient, such as a chemotherapy patient, said method comprising the step of administering a modulator of microRNA-155, such as the pharmaceutical composition of the invention, to said patient, such as during or subsequent to chemotherapy treatment—suitably the modulator of microRNA-155 is a microRNA 155 mimic.

Enhancing white blood cell count may be advantageous in reducing the severity or treating type I allergy responses. In some embodiments the inflammatory disease is Crohn's disease or a type I allergy, which may in some embodiments be treated with a microRNA 155 mimic. Decreasing white blood cell count may be advantageous in reducing the severity or treating type II allergy responses. In some embodiments the inflammatory disease is arthritis such as rheumatoid arthritis, which may for example be treated with an inhibitor of microRNA-155. In some embodiments the inflammatory disease is psoriasis. In some embodiments the inflammatory disease is atherosclerosis or pulmonary disease such as chronic obstructive pulmonary disease (COPD). In some embodiment the auto-immune disease is multiple sclerosis.

The invention provides for compositions comprising a miR-155 inhibitor, to be used in a method of treating a variety of diseases, including prevention or treatment of chronic or acute inflammatory or autoimmune diseases, especially those associated with aberrant lymphocyte or monocyte accumulation such as Chronic and acute inflammatory or autoimmune diseases, aberrant lymphocyte or monocyte accumulation, arthritis, juvenile idiopathic arthritis, rheumatoid arthritis, acute and chronic arthritis, asthma, atherosclerosis, diabetic nephropathy, inflammatory bowel disease, Crohn's disease, multiple sclerosis, nephritis, glomerulonephritis, pancreatitis, pulmonary fibrosis, psoriasis, restenosis, transplant rejection, early stages of allergic responses, inhibition of LTC4, to prevent AHR (airway hyper-responsiveness), tuberculosis infection and malignancy, stroke, castleman's disease, neoplasm, high-grade multiple myeloma, malignant mesotheliomas, paraneoplastic syndrome of mesotheliomas, immunosuppression, cachexia, thrombocytosis, amyloidosis, osteogenesis imperfect, homocystinuria, osteoporosis, osteopetrosis, inflammation of bone mass w arthritis and r. arthritis, peridontal disease, fibrous dysplasia, Paget's disease, chronic renal failure, endocrinopathies, hypercalcemia, deficiency states, malabsorption syndromes, cronic liver disease, cancer metastasis, mammary tumor progression to metastasis, all of which are to individual embodiments.

Embodiments

1. A method of modulating the expression of one or more colony stimulatory factors (CSF) in a cell, such as G-CSF, M-CSF and/or GM-CSF, said method comprising administering a modulator of microRNA-155 to the cell in an amount effective to modulate the expression of said CSF.
2. The method according to embodiment 1, wherein said method is a method of enhancing the expression of the CSF in the cell, wherein the modulator of microRNA-155 is a microRNA-155 mimic, which enhances (or supplements) microRNA-155 activity in said cell.
3. The method according to embodiment 1, wherein said method is a method of down-regulating the expression the CSF in a cell which is expressing CSF, wherein said modulator of microRNA-155 is an inhibitor of microRNA-155 to the cell.
4. A method for the simultaneous inhibition of the expression of G-CSF, M-CSF, CCL-2 and IL-6 in a cell, said method comprising administering a modulator of microRNA-155 to the cell in an amount effective to modulate the expression of said G-CSF, M-CSF, CCL-2 and IL-6.
5. The method according to any one of embodiments 1-4, wherein said cell is a mammalian cell, such as a monocytes/macrophages, granulocytes, neutrophils, and/or eosinophils, or precursor thereof, such as a pluripotent haemopoitic stem cell and/or colony forming unit (CFU),
6. The method according to embodiment 5, wherein said cell is a white blood cell precursor cell.
7. The method according to any one of embodiments 1-6, wherein said cell is over-expressing or under-expressing said CSF.
8. The method according to any one of embodiments 1-7, wherein said method is performed in vitro.
9. The method according to any one of embodiments 1-7, wherein said method is performed in vivo.
10. The method according to any one of embodiments 1-9, wherein said modulator of microRNA-155 comprises an oligomer of between 6 and 30 nucleotides in length, wherein said oligomer consists or comprises of a contiguous nucleotide sequence which is either
    a. fully complementary to at least six contiguous nucleotides present in microRNA-155 (the inhibitor of microRNA-155), or;
    b. Identical to (100% homologous to) at least six contiguous nucleotides present in microRNA-155 (the mimic of microRNA-155).
11. The method according to embodiment 10, wherein said oligomer consists or comprises of a contiguous nucleotide sequence which is either identical to or is fully complementary to the seed region of microRNA-155.
12. The method according to embodiment 10 or 11, wherein the contiguous nucleotide sequence of the oligomer is either identical to the corresponding region of microRNA-155, or complement thereof, or comprises no more than one or two mismatches with the corresponding region of microRNA-155, such as SEQ ID NO 1, 2, 3 or 4, or reverse complement thereof.
13. The method according to claim any one of embodiments 10-12, wherein the contiguous nucleotide sequence of the oligomer consists or comprises between 7-23 nucleotides which are complementary to the corresponding region of microRNA-155 or complement thereof, or comprise no more than 1 or 2 mismatches with the corresponding region of microRNA-155, or reverse complement thereof.
14. The method according to embodiment 13, wherein the contiguous nucleotide sequence consists of 7, 8, 9, 10, 11, 12, 13, 14, 15, 16, 17, 18, 19, 20, 21, 22 or 23 nucleotides which are either identical to or fully complementary to a sequence found in SEQ ID NO 2, or comprise no more than 1 or 2 mismatches with the corresponding region of SEQ ID NO 2, or reverse complement thereof.
15. The method according to embodiment 14, wherein the contiguous nucleotide sequence consists or comprises of between 17 and 23 nucleotides which are identical to a corresponding sequence in SEQ ID NO 2, or comprise no more than one to two mismatches with the corresponding sequence of SEQ ID NO 2 (mimic).
16. The method according to embodiment 14, wherein the contiguous nucleotide sequence consists or comprises of between 7 and 16 nucleotides which are fully complementary to a corresponding sequence found in SEQ ID NO 2, or comprise no more than 1 or 2 mismatches with the corresponding region of the reverse complement of SEQ ID NO 2.
17. The method according to embodiment 14, wherein the contiguous nucleotide sequence of the oligomer consists of between 8-11 nucleotides which are fully complementary to the corresponding region of SEQ ID NO 2.
18. The method according to any one of embodiments 10-17, wherein said oligomer consists of said contiguous nucleotide sequence.
19. The method according to any one of embodiments 10-18, wherein the oligomer is an antimiR, wherein the contiguous nucleotide sequence of the antimlR comprises one or more LNA units.
20. The method according to embodiment 19, wherein the oligomer is an antimiR, wherein the contiguous nucleotide sequence of the antimlR comprises or consist of any one of SEQ ID NO's: 5-25.
21. The method according to any one of embodiments 10-19 wherein said oligomer is a single stranded oligonucleotide.
22. The method according to any one of embodiments 10-19 wherein said oligomer forms one strand of a double stranded RNA complex such as a siRNA.
23. A method of treating an inflammatory or an autoimmune disease in a subject, said method comprising the step of administering an effective amount of a modulator of microRNA-155 to said subject.

24. The method according to embodiment 23, wherein said inflammatory disease is a chronic inflammatory disease or an auto-immune disease.

25. The method according to embodiment 23 or 24, wherein said modulator of microRNA-155 is an inhibitor of microRNA-155, and wherein said inflammatory disease is mediated via a type II hypersensitivity response.

26. The method according to claim any one of embodiments 23-24, wherein the disease is selected from the group consisting of; arthritis, such as rheumatoid arthritis or collagen induced arthritis; pulmonary disease, psoriasis, and multiple sclerosis.

27. The method according to embodiment 23 or 24, wherein said modulator of microRNA-155 is an enhancer or mimic of microRNA-155, and wherein said inflammatory disease is mediated via a type I hypersensitivity response.

28. The method according to embodiment 23, 24 or 27, wherein the disease is selected from the group consisting of Crohn's disease, or a type I (IgE mediated) allergy.

29. A method of reducing the concentration of white blood cells, such as monocytes/macrophages, granulocytes, neutrophils, and/or eosinophils, in a subject, said method comprising the step of administering of an inhibitor of microRNA-155 to said subject.

30. A method of enhancing the concentration of white blood cells, such as monocytes/macrophages, granulocytes, neutrophils, and/or eosinophils, in a subject, said method comprising the step of administering of a microRNA-155 mimic to said subject.

31. An inhibitor of microRNA-155 for use for down-regulating one or more CSFs in a cell.

32. An inhibitor of microRNA-155 for use for the treatment of a disease selected from the list: prevention or treatment of chronic or acute inflammatory or autoimmune diseases, especially those associated with aberrant lymphocyte or monocyte accumulation such as Chronic and acute inflammatory or autoimmune diseases, aberrant lymphocyte or monocyte accumulation, arthritis, juvenile idiopathic arthritis, rheumatoid arthritis, acute and chronic arthritis, asthma, atherosclerosis, diabetic nephropathy, inflammatory bowel disease, Crohn's disease, multiple sclerosis, nephritis, glomerulonephritis, pancreatitis, pulmonary fibrosis, psoriasis, restenosis, transplant rejection, early stages of allergic responses, inhibition of LTC4, to prevent AHR (airway hyper-responsiveness), tuberculosis infection and malignancy, stroke, castleman's disease, neoplasm, high-grade multiple myeloma, malignant mesotheliomas, paraneoplastic syndrome of mesotheliomas, immunosuppression, cachexia, thrombocytosis, amyloidosis, osteogenesis imperfect, homocystinuria, osteoporosis, osteopetrosis, inflammation of bone mass w arthritis and r. arthritis, peridontal disease, fibrous dysplasia, Paget's disease, chronic renal failure, endocrinopathies, hypercalcemia, deficiency states, malabsorption syndromes, cronic liver disease, cancer metastasis, mammary tumor progression to metastasis.

33. A microRNA-155 mimic for use for up-regulating one or more CSFs in a cell.

34. A microRNA-155 mimic for use for the treatment of an inflammatory disease.

35. Use of a microRNA-155 modulator in the preparation of a medicament for the treatment of one of the following diseases: prevention or treatment of chronic or acute inflammatory or autoimmune diseases, especially those associated with aberrant lymphocyte or monocyte accumulation such as Chronic and acute inflammatory or autoimmune diseases, aberrant lymphocyte or monocyte accumulation, arthritis, juvenile idiopathic arthritis, rheumatoid arthritis, acute and chronic arthritis, asthma, atherosclerosis, diabetic nephropathy, inflammatory bowel disease, Crohn's disease, multiple sclerosis, nephritis, glomerulonephritis, pancreatitis, pulmonary fibrosis, psoriasis, restenosis, transplant rejection, early stages of allergic responses, inhibition of LTC4, to prevent AHR (airway hyper-responsiveness), tuberculosis infection and malignancy, stroke, castleman's disease, neoplasm, high-grade multiple myeloma, malignant mesotheliomas, paraneoplastic syndrome of mesotheliomas, immunosuppression, cachexia, thrombocytosis, amyloidosis, osteogenesis imperfect, homocystinuria, osteoporosis, osteopetrosis, inflammation of bone mass w arthritis and r. arthritis, peridontal disease, fibrous dysplasia, Paget's disease, chronic renal failure, endocrinopathies, hypercalcemia, deficiency states, malabsorption syndromes, cronic liver disease, cancer metastasis, mammary tumor progression to metastasis.

36. A pharmaceutical composition comprising a modulator of microRNA-155, at least one further anti-inflammatory agent, and a pharmaceutical diluents, carrier or adjuvant.

37. The pharmaceutical composition according to embodiment 36, wherein the at least one further anti-inflammatory agent is selected from a group consisting of: non-steroidal anti-inflammatory drugs (NSAIDs), or tumor necrosis factor receptor inhibitors.

38. A method of enhancing white blood cell count in a patient, such as a chemotherapy patient, said method comprising the step of administering a modulator of microRNA-155, such as the pharmaceutical composition of the invention, to said patient, such as during or subsequent to chemotherapy treatment.

EXAMPLES

Example 1

LPS-Mediated Induction of MiR-155 Iin Cultured Mouse Raw264.7 Macrophages

We have recently reported on effective microRNA silencing using complementary LNA-antimiRs in combination with transcriptome analysis as a useful approach to dissect the biological roles of individual miRNAs in vitro and in vivo (Elmen et al. (2008) *Nature* 452:896-899; Elmen et al. (2008) *Nucleic Acids Res.* 36:1153-1162. Hence, to enable further studies on miR-155 targets and miR-155 associated gene networks, we designed LNA-antimiRs targeting the murine and the human miR-155 as well as a LNA-control oligonucleotide.

We first investigated the expression of miR-155 in murine Raw264.7 macrophage cells upon LPS stimulation.

Results: Treatment of cultured mouse macrophages with LPS showed dose-dependent induction of miR-155 with more than ten-fold increase in miR-155 expression levels at a concentration of 100 ng/ml LPS after 18 h (FIG. 1A). Consistent with these data, a miR-155 luciferase reporter construct harbouring a perfect match miR-155 target site in the 3' UTR of the *Renilla* luciferase gene showed a dose-dependent repression of the luciferase reporter, which correlated with the increased expression of miR-155 in LPS-treated mouse Raw264.7 macrophages (FIG. 1B). The LNA-antimiR-155 showed dose-dependent silencing of miR-155 in LPS-treated mouse Raw264.7 macrophages as shown by efficient de-repression of the miR-155 luciferase reporter, whereas the LNA mismatch control oligonucleotide had no effect on the luciferase reporter activity at the same concentrations (FIG. 1C).

Since the LNA-antimiR resulted in potent and specific antagonism of miR-155 in cultured Raw264.7 cells at 5 nM concentration, we chose these experimental conditions for further studies in mouse macrophages.

Conclusion: LNA-antimiR-155 potently and specifically antagonized murine miR-155 in cultured Raw264.7 cells at 5 nM concentration.

Materials and Methods: Design and synthesis of LNA oligonucleotides: The LNA-antimiR oligonucleotides were synthesized as unconjugated and fully phosphorothiolated oligonucleotides. The perfectly matching LNA-antimiR oligonucleotide 5'-TcAcAATtaG$^m$CAtTA-3' (SEQ ID NO: 17) was complementary to nucleotides 2-16 in the mature murine miR-155 sequence. The mismatch LNA control oligonucleotide was synthesized with the following sequence: 5'-TcAa$^m$CATtaGA$^m$CtTA-3' (SEQ ID NO: 18) (uppercase: LNA; lowercase: DNA; $^m$C denotes LNA methylcytosine).

Cell culture: Raw264.7 cells were grown in Dulbecco's modified Eagles medium (DMEM) (Invitrogen) supplemented with 10% FBS, 4 mM Glutamax I and 25 µg/ml Gentamicin (Invitrogen). Lipopolysaccharide (LPS) was purchased from Sigma and activation of Raw264.7 cells was induced by treating cells with 1, 10 or 100 ng/ml LPS for indicated time periods.

Transfection: Raw264.7 cells were transfected with the Lipofectamine 2000 transfection reagent according to the manufacturer's protocol (Invitrogen) and the LNA-antimiR oligonucleotides were used at a final concentration of 1 or 5 nM as indicated. The transfections and luciferase activity measurements were carried out according to the manufacturer's instructions (Invitrogen Lipofectamine 2000/Promega Dual-luciferase kit). Relative luciferase activity levels were expressed as Renilla/Firefly luciferase ratios.

Plasmids: The perfect match target sequence for the murine-miR-155 was cloned downstream of the Renilla luciferase gene (XhoI/NotI sites) in the psiCHECK2 vector (Promega) using 5' phosphorylated oligos: murine miR-155 forward 5'-tcgagccctatcacaattagcatmagc-3' (SEQ ID NO:26), and reverse 5'-ggccgcttaatgctaattgtgataggggc-3' (SEQ ID NO:27).

Real-time quantitative RT-PCR: Total RNA was extracted with Trizol reagent according to the manufacturer's instructions (Invitrogen), except that the precipitated RNA pellet was washed in 80% ethanol and not mixed. The miR-155 levels were quantified using the mirVana real-time RT-PCR detection kit (Ambion) following the manufacturer's instructions, except that 200 ng total RNA was used in the reverse transcription (RT) reaction. A two-fold total RNA dilution series from LPS-treated mouse spleen RNA or LPS-treated Raw264.7 RNA served as standard to ensure a linear range (Ct versus relative copy number) of the amplification. The RT reaction was diluted ten times in water and 10 µl aliquots were subsequently used for RT-PCR amplification according to the manufacturer's instructions (Ambion).

The Applied Biosystems 7500 Real-Time PCR instrument was used for amplification.

Example 2

Translational Repression of c/ebp Beta Isoforms By MiR-155

LPS stimulation of cultured mouse Raw264.7 cells leads to an inflammatory response in which miR-155 and more than 700 genes are up-regulated (Huang et al. (2006) Arch. Pharm. Res. 29:890-897), including the transcription factor c/ebp Beta gene (Gorgoni B et al. (2002) J. Immunol. 168:4055-4062). miR-155 target site sequences are present in the 3' UTR c/ebp Beta transcript, which is highly conserved among five vertebrate species (FIG. 2A). The c/ebp Beta transcript encodes three isoforms, designated as LAP*, LAP and LIP, that are generated by differential translational initiation (FIG. 2A). The short LIP form lacks the transactivation domain (TAD), but is still capable of binding to DNA and forms homo- or heterodimers through the basic region leucine zipper (bZIP) domain and therefore behaves as a dominant negative. The expression of the three isoforms is regulated in a complex manner, and even differential activation of the isoforms upon LPS stimulation has been reported (O'Connel et al. (2008) J. Exp. Med. 205:585-594).

Figure 2C:
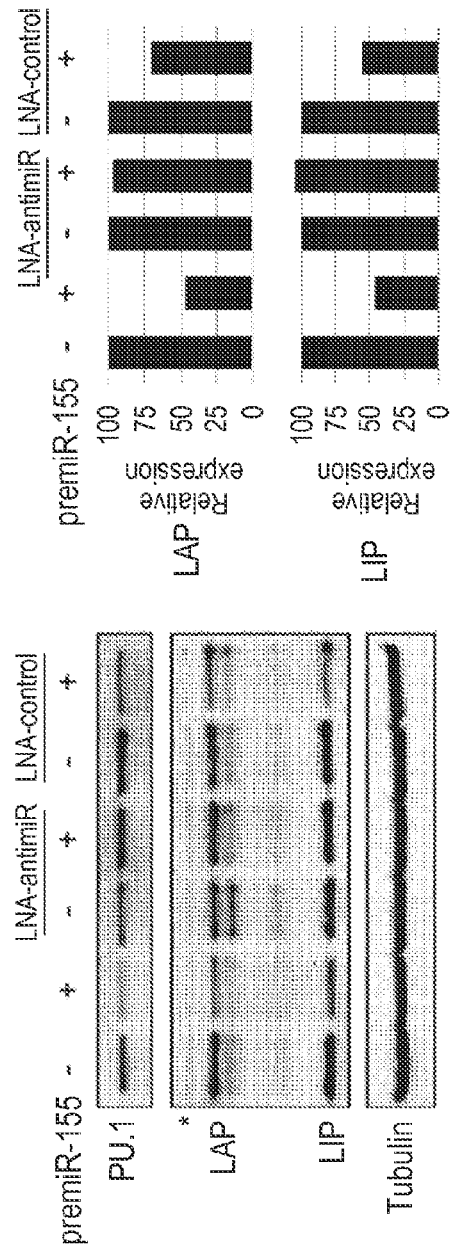

Results: We found that a luciferase reporter harbouring the c/ebp Beta 3' UTR showed significant ($p<0.001$) miR-155 dependent repression relative to a control reporter plasmid (FIG. 2B), strongly indicating that c/ebp Beta is a direct target of miR-155, consistent with two recent reports (19, 20). To better understand the miR-155 mediated regulation of the various c/ebp Beta isoforms, we first investigated protein extracts from untreated murine macrophages by Western blot analyses using a C-terminal specific c/ebp Beta antibody that recognizes all three isoforms. Transient transfection of the precursor miR-155 (premiR-155) into mouse macrophage Raw264.7 cells resulted in repression of all three c/ebp Beta isoforms, whereas concomitant transfection of the LNA-antimiR into the cells effectively antagonized the miR-155 mediated repression (FIG. 2C). We also observed repression of another direct miR-155 target, the Ets family transcription factor Pu.1 in Raw264.7 cells (FIG. 2C), (10), implying that both c/ebp Beta and Pu.1 are targeted by miR-155 in Raw264.7 macrophages.

Figure 2D:
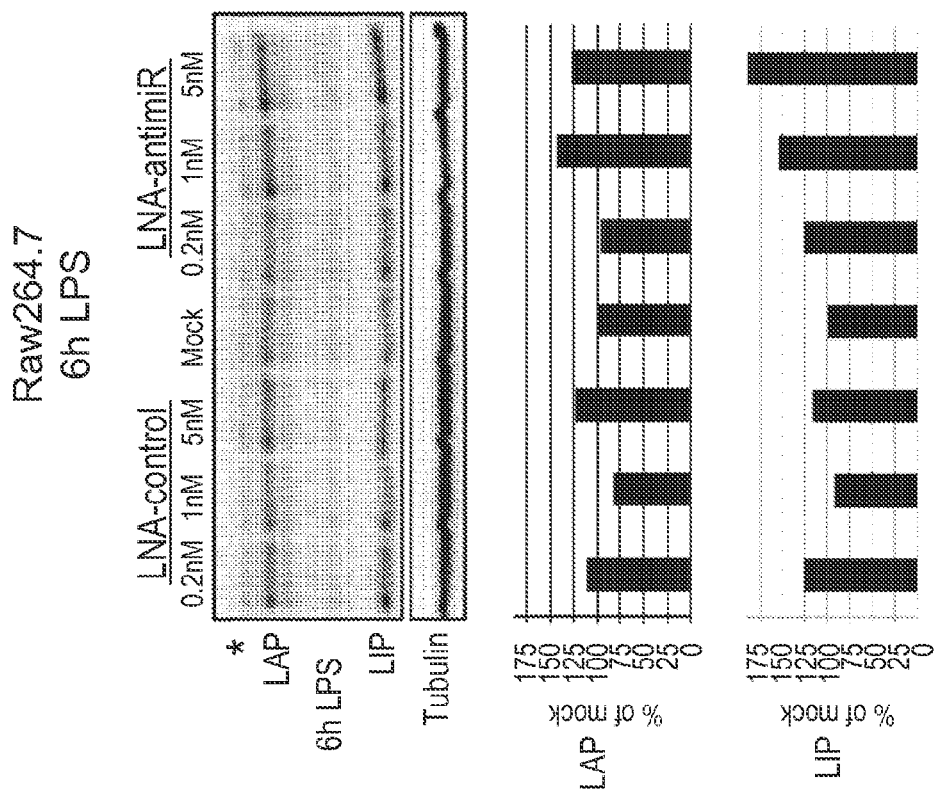
Figure 2E:
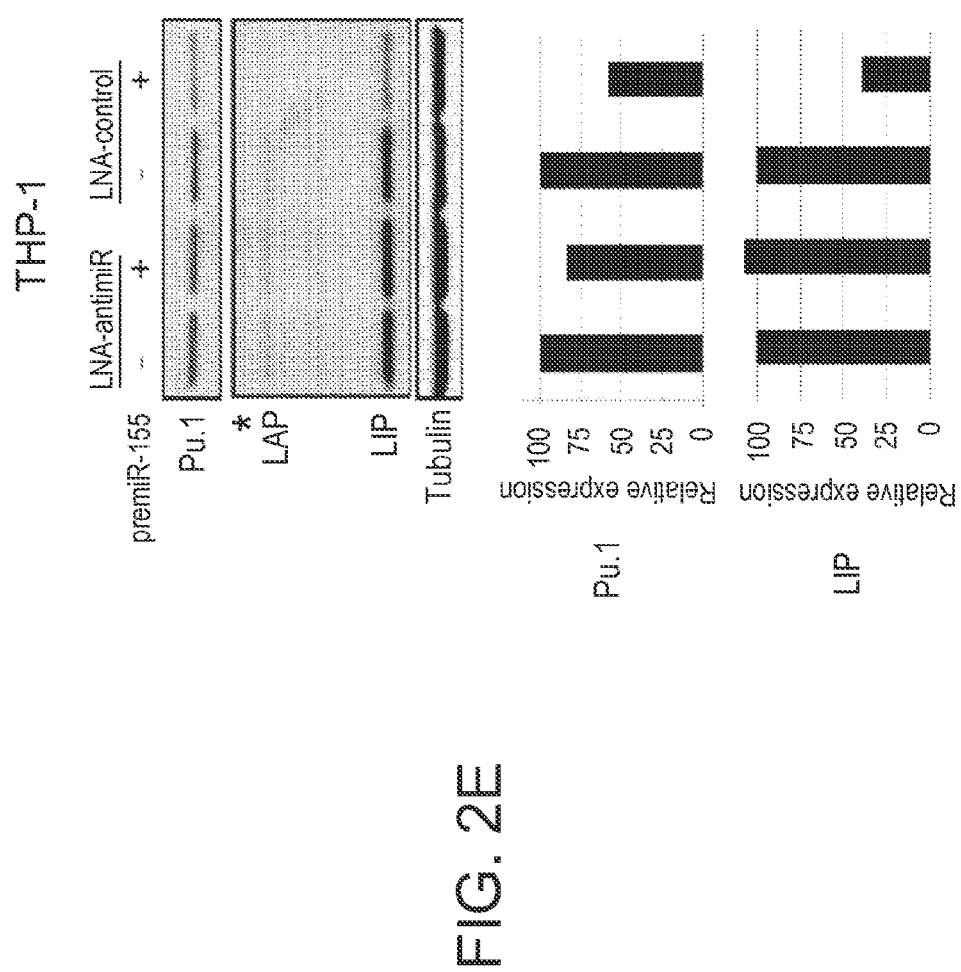

Next, we investigated miR-155 mediated repression of c/ebp Beta isoforms upon LPS activation of macrophages by transfection of the LNA-antimiR or the LNA control, respectively, into mouse Raw264.7 cells in combination with a six-hour treatment with LPS, which was previously shown to result in a strong inflammatory-like response in Raw264.7 cells (18). Silencing of miR-155 by LNA-antimiR led to a dose-dependent de-repression of the short LIP isoform showing 80% derepression at the highest concentration of 5 nM as determined by Western blot analysis (FIG. 2D). By comparison, derepression of the LAP isoform levels was less pronounced (FIG. 2D). Similar results were observed in the undifferentiated human monocytic THP-1 cells, in which treatment with LNA-antimiR resulted in derepression of the short LIP isoform (FIG. 2E). Taken together, our data demonstrate that the levels of individual c/ebp Beta isoforms are tightly regulated by miR-155.

Conclusion: Antagonizing miR-155 by LNA-antimiRs block translational repression of c/ebp Beta isoforms.

Materials and Methods: Design and synthesis of LNA oligonucleotides: The LNA-antimiR oligonucleotides were synthesized as unconjugated and fully phosphorothiolated oligonucleotides. The perfectly matching LNA-antimiR oligonucleotide 5'-TcAcAATtaG$^m$CAtTA-3' (SEQ ID NO: 17) was complementary to nucleotides 2-16 in the mature murine miR-155 sequence and the has LNA-antimiR-155 oligonucleotide 5'-TcAcGATtaG$^m$CAtTA-3' (SEQ ID NO: 9) was complementary to nucleotides 2-16 in the mature human miR-155 sequence. The mismatch LNA control oligonucleotide was synthesized with the following sequence: 5'-TcAa$^m$CATtaGA$^m$CtTA-3' (SEQ ID NO: 18) (uppercase: LNA; lowercase: DNA; $^m$C denotes LNA methylcytosine).

Cell culture: Raw264.7 cells were grown in Dulbecco's modified Eagles medium (DMEM) (Invitrogen) supplemented with 10% FBS, 4 mM Glutamax I and 25 µg/ml Gentamicin (Invitrogen). Lipopolysaccharide (LPS) was purchased from Sigma and activation of Raw264.7 cells was induced by treating cells with 100 ng/ml LPS. THP-1 cells were grown in RPMI-1640 (Invitrogen) supplemented with 10% FBS, 4 mM Glutamax I and 25 µg/ml Gentamicin (Invitrogen). Raw264.7 and THP-1 cells were transfected with the Lipofectamine 2000 transfection reagent according to the manufacturer's protocol (Invitrogen) and the LNA-antimiR oligonucleotides were used at a final concentration of 5 nM unless otherwise stated. Human miR-155 precursor (premiR-155, Ambion) was cotransfected at a final concentration of 5 nM. HeLa cells were cultivated in Eagles MEM (Invitrogen) with 10% FBS, 2 mM Glutamax I, non-essential amino acids and 25 µg/ml Gentamicin (Invitrogen). HeLa cells were cotransfected with human premiR-155 (Ambion) at a final concentration of 50 nM and 0.1 µg luciferase reporter plasmid using Lipofectamine 2000. The transfections and luciferase activity measurements were carried out according to the manufacturer's instructions (Invitrogen Lipofectamine 2000/Promega Dual-luciferase kit). Relative luciferase activity levels were expressed as *Renilla*/Firefly luciferase ratios.

Plasmids: The perfect match target sequence for the human-miR-155 was cloned downstream of the *Renilla* luciferase gene (XhoI/NotI sites) in the psiCHECK2 vector (Promega) using 5' phosphorylated oligos: human miR-155 forward 5'-tcgagccctatcacgattagcattaagc-3' (SEQ ID NO:34), and reverse 5'-ggccgcttaatgctaatcgtgatagggg-3' (SEQ ID NO:35). The 3' UTR of human c/ebp Beta was cloned downstream of the *Renilla* luciferase gene (XhoI/NotI sites) in the psiCHECK2 vector PCR primers used for amplification of the human c/EBPBeta 3' UTR (basepairs 1328-1837 accession no. NM_005194) were forward 5'-aaaaaactc-gagaaaactttggcactggggca-3' (SEQ ID NO:36) (inlc. A XhoI site), reverse 5'-aaaaaageggccgcggattgtaaccattctcaaa-3' (SEQ ID NO:37) (incl. a NotI site).

Western blot analysis: Raw264.7 proteins were extracted using RIPA lysis buffer (50 mM Tris-HCl pH 7.4, 150 mM NaCl, 1 mM EDTA, 1% Triton X-100, 0.1% SDS, 1% Sodium Deoxycholate) and electrophoresed on NuPAGE Bis Tris 4-12% gels (Invitrogen) using 100 µg protein per sample. The proteins were transferred to a nitrocellulose membrane using iBlot (Invitrogen) according to manufacturer's instructions. ECL advanced western kit (GE Healthcare Life Sciences) was used for blocking, antibody dilution and detection according to the manufacturer. A primary monoclonal mouse-anti-c/ebp Beta antibody (SC-7962, Santa Cruz Biotechnology), a primary rabbit-anti-PU.1 (#2258, Cell signaling Technology), a primary mouse-anti-Tubulin-alpha Ab-2 (MS-581-P, Neomarkers) and HRP-conjugated secondary rabbit anti-mouse (PO447, DAKO) or swine anti-rabbit antibodies (P0399, DAKO) were used according to the manufacturer's instructions.

Example 3

MiR-155 Regulates c/ebp Beta In the Splenocytes of LPS-Treated Mice

The expression of c/ebp Beta is induced during macrophage activation, whereas Pu.1 is expressed both in resting B cells and macrophages and in the spleen germinal center B cells (Gorgoni B et al. (2002) *J. Immunol.* 168:4055-4062; Schebesta M et al. (2002) *Curr. Opin. Immunol.* 14:216-223). Since spleen contains populations of monocytes and macrophages together with B and T cells, we investigated miR-155 mediated regulation of c/ebp Beta in the splenocytes of LPS-treated mice in combination with LNA-antimiR based miR-155 silencing.

Results: We first asked whether these cells could be targeted by systemically administered LNA oligonucleotides in vivo by isolating B cells and monocytic cell populations from murine spleen after intravenous dosing with a 6-carboxyfluorescein (FAM)-labeled LNA oligonucleotide. Confocal microscopy of the murine B cells and monocyte/macrophages showed that the FAM-labeled LNA control was readily taken up by these cells, indicating that miR-155 could be targeted in both cell types by an LNA-antimiR (FIG. 3A). Intraperitoneal administration of LPS significantly induced the expression of miR-155 in splenocytes 2 hours post treatment, thereby corroborating our results obtained with LPS-stimulated murine macrophages (FIG. 3B). The splenocytes of untreated mice showed low levels of c/ebp Beta proteins, whereas the levels of both the LAP and LIP isoform of c/ebp Beta were significantly increased 24 hours after treatment with LPS (FIG. 3C), in accordance with a previous report (Gorgoni B et al. (2002) *J. Immunol.* 168:4055-4062). Systemic administration of the LNA-antimiR in LPS-treated mice effectively antagonized miR-155 compared to the vehicle and LNA mismatch control treated mice, respectively (FIG. 3B). This resulted in marked derepression of both the LAP and LIP isoform in comparison to the control mice (FIG. 3C), which is consistent with the notion that miR-155 negatively regulates c/ebp Beta in vivo in mouse splenocytes during acute inflammatory response.

Conclusion: LNA oligonucleotides are located in B cells (CD19) and monocyte/macrophages (CD11b) isolated from murine spleen after intravenous dosing and miR-155 regulates c/ebp Beta in the splenocytes of LPS-treated mice.

Materials and Methods: Design and synthesis of LNA oligonucleotides: The LNA-antimiR oligonucleotides were synthesized as unconjugated and fully phosphorothiolated oligonucleotides. The perfectly matching LNA-antimiR oligonucleotide 5'-TcAcAATtaG$^m$CAtTA-3' (SEQ ID NO: 17) was complementary to nucleotides 2-16 in the mature murine miR-155 sequence. The mismatch LNA control oligonucleotide was synthesized with the following sequence: 5'-TcAa$^m$CATtaGA$^m$CtTA-3' (SEQ ID NO: 18) (uppercase: LNA; lowercase: DNA; $^m$C denotes LNA methylcytosine).

Isolation of B cells and monocytic/macrophage cell fractions from mice splenocytes: C57BL/6J female mice (Taconic M&B Laboratory Animals) were injected intravenously with a FAM-labeled LNA-control for three consecutive days, receiving daily doses of 25 mg/kg and the animals were sacrificed 24 hours after last dose. Spleens were surgically removed and positive selection of Monocytes/macrophages was carried out by MACS® Cell separation systems (Miltenyi Biotech) using magnetic beads conjugated with CD11b antibodies and the MACS® Cell separation columns according to the manufacturer's instructions (Miltenyi Biotec). B cells were isolated using magnetic beads conjugated with CD19 antibodies (Miltenyi Biotec). PE-conjugated CD11b and CD19 antibodies were added to isolated fractions to verify the identity of the isolated cells by FACS analysis. Fixed isolated cells were DAPI stained and transferred to microscope slides. Cellular uptake of the FAM-labeled LNA oligonucleotide was investigated by confocal microscopy.

In vivo experiments: C57BL/6J female mice (Taconic M&B Laboratory Animals) with 27 g average body weight at first dosing were used in all experiments and received regular chow diet (Altromin no 1324, Brogaarden). The LNA compounds were formulated in physiological saline (0.9% NaCl) to a final concentration allowing the mice to receive a tail vein injection volume of 10 ml/kg. The animals were dosed for three consecutive days with LNA-antimiR, LNA mismatch control or saline (vehicle control), receiving daily doses of 25 mg/kg and sacrificed 24 hours after last dose. Saline-formulated bacterial LPS was administered by intraperitoneal injections at 0.5 mg/kg and the mice were sacrificed either 2 or 24 hours post LPS treatment. Immediately after sacrificing the animals, spleen samples were dissected. All experiments were performed according to the principles stated in the Danish law on animal experiments and were approved by the Danish Animal Experiments Inspectorate, Ministry of Justice, Denmark.

Real-time quantitative RT-PCR: The dissected mice spleens were immediately stored in RNA later (Ambion). Total RNA from spleens was extracted with Trizol reagent according to the manufacturer's instructions (Invitrogen), except that the precipitated RNA pellet was washed in 80% ethanol and not mixed. The miR-155 levels were quantified using the mirVana real-time RT-PCR detection kit (Ambion) following the manufacturer's instructions, except that 200 ng total RNA was used in the reverse transcription (RT) reaction. A two-fold total RNA dilution series from LPS-treated mouse spleen RNA or LPS-treated Raw264.7 RNA served as standard to ensure a linear range (Ct versus relative copy number) of the amplification. The RT reaction was diluted ten times in water and 10 µl aliquots were subsequently used for RT-PCR amplification according to the manufacturer's instructions (Ambion). The Applied Biosystems 7500 Real-Time PCR instrument was used for amplification.

Western blot analysis: Spleen proteins were extracted using RIPA lysis buffer (50 mM Tris-HCl pH 7.4, 150 mM NaCl, 1 mM EDTA, 1% Triton X-100, 0.1% SDS, 1% Sodium Deoxycholate) and electrophoresed on NuPAGE Bis Tris 4-12% gels (Invitrogen) using 100 µg protein per sample. The proteins were transferred to a nitrocellulose membrane using iBlot (Invitrogen) according to manufacturer's instructions. ECL advanced western kit (GE Healthcare Life Sciences) was used for blocking, antibody dilution and detection according to the manufacturer. A primary monoclonal mouse-anti-c/ebp Beta antibody (SC-7962, Santa Cruz Biotechnology), a primary rabbit-anti-PU.1 (#2258, Cell signaling Technology), a primary mouse-anti-Tubulin-alpha Ab-2 (MS-581-P, Neomarkers) and HRP-conjugated secondary rabbit anti-mouse (PO447, DAKO) or swine anti-rabbit antibodies (P0399, DAKO) were used according to the manufacturer's instructions.

Example 4

MiR-155 Mediates Regulation of Granulocyte-Colony Stimulating Factor (G-CSF)

In order to identify immune response genes whose expression could be mediated by miR-155 in activated macrophages, we carried out expression profiling of RNA samples extracted from bacterial lipopolysaccharide (LPS)-stimulated mouse macrophage Raw264.7 cells using mouse immune real-time RT-PCR arrays. To establish a link between miR-155 and the expression of immune response genes, the LPS-stimulated Raw264.7 cells were transfected with either LNA-antimiR-155, and miR-155 mimic, purchased from Ambion, and as described above or LNA mismatch control also as described above. The findings were extended to a human monocytic cell line and to an in vivo setting. A direct link between the c/ebp Beta LIP isoform and G-CSF was established.

Figure 4C:
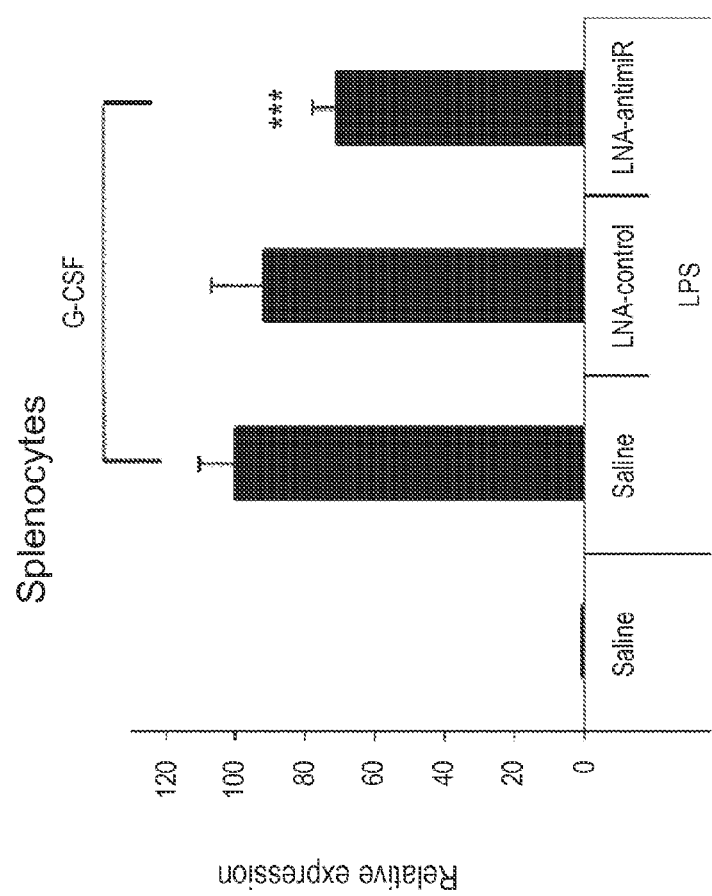
Figure 4D:
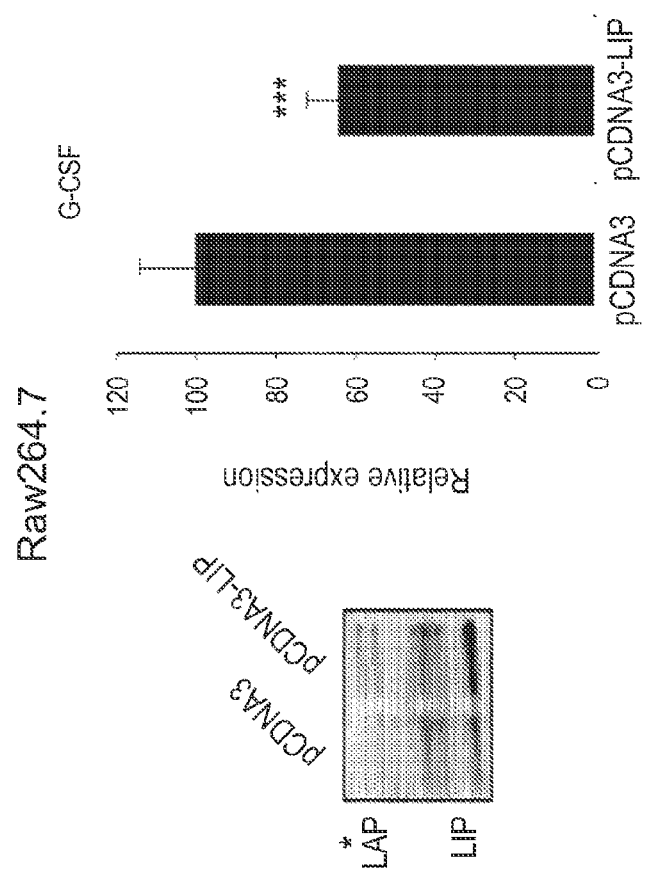

Results: Expression profiling demonstrated that among the immune response genes induced by LPS treatment, the Csf3 gene encoding Granulocyte colony-stimulating factor (G-CSF) was significantly down-regulated in LNA-antimiR treated cells compared to untreated and LNA mismatch controls ($p=0.014$ and $p=0.008$, respectively, Student's t-test, two-sided), implying that the regulation of G-CSF expression is mediated by miR-155 (Table 1 in FIG. 6 and FIG. 4A). To validate this conclusion we assessed the effect of miR-155 on G-CSF expression in human monocytic THP-1 cells. Transient transfection of premiR-155 into LPS-stimulated THP-1 cells resulted in significant up-regulation of the G-CSF mRNA ($p<0.01$, Student's t-test, two-sided), that reverted to control levels upon antagonism of miR-155 by LNA-antimiR (FIG. 4B). Consistent with our data on mouse macrophages and human monocytes, we observed that G-CSF mRNA was significantly down-regulated in the splenocytes of miR-155 antagonized LPS-treated mice ($p=0.0007$ and $p=0.02$, Student's t-test, two-sided) compared to saline and LNA-control treated animals (FIG. 4C). Since we found that miR-155 exerted a pronounced regulatory effect on the LIP isoform of c/ebp Beta, we next asked whether over-expression of LIP in Raw264.7 cells would lead to down-regulation of G-CSF. Indeed, transfection of an expression construct for the short LIP isoform into LPS-stimulated Raw264.7 cells resulted in over-expression of LIP as shown by Western blot analysis, which coincided with a marked down-regulation of the G-CSF transcript in mouse Raw264.7 macrophages (FIG. 4D).

Conclusion: During LPS stimulation of mouse macrophage Raw264.7 cells antagonizing miR-155 leads to reduction of G-CSF mRNA levels. In vivo, antagonizing miR-155 during LPS stimulation leads to reduced levels of G-CSF mRNA levels in splenocytes. Considered together, our data provide evidence that miR-155 mediates regulation of multiple CSF gene expression, probably through its direct target c/ebp Beta during acute inflammatory response.

Materials and Methods: Design and synthesis of LNA oligonucleotides: The LNA-antimiR oligonucleotides were synthesized as unconjugated and fully phosphorothiolated oligonucleotides. The perfectly matching LNA-antimiR oligonucleotide 5'-TcAcAATtaG$^m$CAtTA-3' (SEQ ID NO: 17) was complementary to nucleotides 2-16 in the mature murine miR-155 sequence and 5'-TcAcGATtaG$^m$CAtTA-3' (SEQ ID NO: 9) was complementary to nucleotides 2-16 in the mature human miR-155 sequence. The mismatch LNA control oligonucleotide was synthesized with the following sequence: 5'-TcAa$^m$CATtaGA$^m$CtTA-3' (SEQ ID NO: 18) (uppercase: LNA; lowercase: DNA; $^m$C denotes LNA methylcytosine).

Cell culture: Raw264.7 cells were grown in Dulbecco's modified Eagles medium (DMEM) (Invitrogen) supplemented with 10% FBS, 4 mM Glutamax I and 25 µg/ml Gentamicin (Invitrogen). Lipopolysaccharide (LPS) was purchased from Sigma and activation of Raw264.7 cells was induced by treating cells with 100 ng/ml LPS for indicated time periods. THP-1 cells were grown in RPMI-1640 (Invitrogen) supplemented with 10% FBS, 4 mM Glutamax I and 25 µg/ml Gentamicin (Invitrogen). Raw264.7 and THP-1 cells were transfected with the Lipofectamine 2000 transfection reagent according to the manufacturer's protocol (Invitrogen) and the LNA-antimiR oligonucleotides were used at a final concentration of 5 nM unless otherwise stated. Human miR-155 precursor (premiR-155, Ambion) was cotransfected at a final concentration of 5 nM. The transfections and luciferase activity measurements were carried out according to the manufacturer's instructions (Invitrogen Lipofectamine 2000/Promega Dual-luciferase kit). Relative luciferase activity levels were expressed as *Renilla*/Firefly luciferase ratios.

Plasmids: The pCDNA3.1 expression construct for the truncated rat c/ebp Beta isoform LIP (amino acids 153-297) was kindly provided by Dr. M. A. Chidgey and has been described elsewhere (Smith C et al. (2004) *Biochem. J.* 380: 757-765). Western blot analysis: Raw264.7 proteins were extracted using RIPA lysis buffer (50 mM Tris-HCl pH 7.4, 150 mM NaCl, 1 mM EDTA, 1% Triton X-100, 0.1% SDS, 1% Sodium Deoxycholate) and electrophoresed on NuPAGE Bis Tris 4-12% gels (Invitrogen) using 100 µg protein per sample. The proteins were transferred to a nitrocellulose membrane using iBlot (Invitrogen) according to manufacturer's instructions. ECL advanced western kit (GE Healthcare Life Sciences) was used for blocking, antibody dilution and detection according to the manufacturer. A primary monoclonal mouse-anti-c/ebp Beta antibody (SC-7962, Santa Cruz Biotechnology) and HRP-conjugated secondary rabbit anti-mouse (P0447, DAKO) were used according to the manufacturer's instructions.

Real-time quantitative RT-PCR: The dissected mice spleens were immediately stored in RNA later (Ambion). Total RNA from spleens or Raw264.7 cells was extracted with Trizol reagent according to the manufacturer's instructions (Invitrogen), except that the precipitated RNA pellet was washed in 80% ethanol and not mixed. G-CSF mRNA quantification was done using standard TaqMan assays (Applied Biosystems). The reverse transcription reaction was carried out with random decamers, 0.5 µg total RNA, and the M-MLV RT enzyme from Ambion according to protocol. First strand cDNA was subsequently diluted 10 times in nuclease-free water before addition to the RT-PCR reaction mixture. The Applied Biosystems 7500 Real-Time PCR instrument was used for amplification.

In vivo experiments: C57BL/6J female mice (Taconic M&B Laboratory Animals) with 27 g average body weight at first dosing were used in all experiments and received regular chow diet (Altromin no 1324, Brogaarden). The LNA compounds were formulated in physiological saline (0.9% NaCl) to a final concentration allowing the mice to receive a tail vein injection volume of 10 ml/kg. The animals were dosed for three consecutive days with LNA-antimiR, LNA mismatch control or saline (vehicle control), receiving daily doses of 25 mg/kg and sacrificed 24 hours after last dose. Saline-formulated bacterial LPS was administered by intraperitoneal injections at 0.5 mg/kg and the mice were sacrificed either 2 or 24 hours post LPS treatment. Immediately after sacrificing the animals, spleen samples were dissected. All experiments were performed according to the principles stated in the Danish law on animal experiments and were approved by the Danish Animal Experiments Inspectorate, Ministry of Justice, Denmark.

Example 5

Identification of CCL2 (Mcp-1), IL-6, M-CSF (Csf1) and G-CSF (Csf3), as miR-155 regulated transcripts.

Expression of CCL2 (Mcp-1), IL-6, M-CSF (Csf1) and G-CSF (Csf3) transcripts extracted from mouse Raw264.7 cells stimulated with 100 ng/ml LPS for 6 h (LPS+) or Raw264.7 cells pretransfected with 5 nM LNA-antimiR-155 (SPC3989) before stimulation with 100 ng/ml LPS for 6 h (LPS+antimiR). Based on data shown in table 1 in FIG. 6, the expression levels of the CCL2 (MCP-1), IL-6 and M-CSF (Csf1) and G-CSF(Csf3) transcripts are shown in FIG. 5. All transcripts are normalized to β2-microglobulin transcripts. The expression levels of the CCL2 (MCP-1), IL-6 and M-CSF(Csf1) and G-CSF (Csf3) transcripts are reduced when treated with LNA-antimiR.

---

The invention claimed is:

1. A method of inhibiting the expression of one or more colony stimulatory factors (CSF) in a mammalian cell, said method comprising administering an inhibitor of microRNA-155 to the mammalian cell in an amount effective to inhibit the expression of said CSF; wherein said inhibitor of microRNA-155 comprises an oligomer of between 6 and 30 nucleotides in length, and wherein said oligomer comprises a contiguous nucleotide sequence which is fully complementary to at least six contiguous nucleotides present in the sequence of microRNA-155.

2. The method according to claim 1, wherein the mammalian cell is selected from the group consisting of monocytes/macrophages, granulocytes, neutrophils, eosinophils, pluripotent haemopoitic stem cell, colony forming units (CFU), and white blood cell precursor cells.

3. The method according to claim 1, wherein said mammalian cell is over-expressing CSF.

4. The method according to claim 1, wherein said method is performed in vitro.

5. The method according to claim 1, wherein said method is performed in vivo.

6. The method according to claim 1, wherein said oligomer comprises a contiguous nucleotide sequence which is either identical to or is fully complementary to the sequence of the seed region of microRNA-155.

7. The method according to claim 1, wherein said oligomer consists of a contiguous nucleotide sequence which is either identical to or is fully complementary to the sequence of the seed region of microRNA-155.

8. The method according to claim 1, wherein the contiguous nucleotide sequence of the oligomer is fully complementary to the sequence of a region of microRNA-155.

9. The method according to claim 1, wherein the contiguous nucleotide sequence of the oligomer comprises between 7 and 23 nucleotides, which are fully complementary to the sequence of the corresponding region of microRNA-155.

10. The method according to claim 9, wherein the contiguous nucleotide sequence of the oligomer comprises between 7 and 23 nucleotides which are fully complementary to a sequence found in SEQ ID NO: 2.

11. The method according to claim 9, wherein the contiguous nucleotide sequence of the oligomer consists of between 7 and 23 nucleotides which are fully complementary to a sequence found in SEQ ID NO: 2.

12. The method according to claim 10, wherein the contiguous nucleotide sequence of the oligomer comprises between 7 and 16 nucleotides which are fully complementary to a sequence found in SEQ ID NO: 2.

13. The method according to claim 10, wherein the contiguous nucleotide sequence of the oligomer consists of between 7 and 16 nucleotides which are fully complementary to a sequence found in SEQ ID NO: 2.

14. The method according to claim 10, wherein the contiguous nucleotide sequence of the oligomer consists of between 8 and 11 nucleotides which are fully complementary to a sequence found in SEQ ID NO: 2.

15. The method according to claim 1, wherein the oligomer comprises one or more LNA units.

16. The method according to claim 1, wherein the contiguous nucleotide sequence of the oligomer is any one of SEQ ID NO's: 5 to 25.

* * * * *

SEQUENCE LISTING

```
<160> NUMBER OF SEQ ID NOS: 37

<210> SEQ ID NO 1
<211> LENGTH: 65
<212> TYPE: RNA
<213> ORGANISM: Homo sapiens

<400> SEQUENCE: 1
cuguuaaugc uaaucgugau aggguuuuu gccuccaacu gacuccuaca uauuagcauu    60
aacag                                                              65

<210> SEQ ID NO 2
<211> LENGTH: 23
<212> TYPE: RNA
<213> ORGANISM: Homo sapiens

<400> SEQUENCE: 2
uuaaugcuaa ucgugauagg ggu                                          23

<210> SEQ ID NO 3
<211> LENGTH: 65
<212> TYPE: RNA
<213> ORGANISM: Murine
```

-continued

```
<400> SEQUENCE: 3 cguuaaugc uaauugugau aggguuuug gccucugacu gacuccuacc uguuagcauu      60
aacag                                                               65

<210> SEQ ID NO 4
<211> LENGTH: 23
<212> TYPE: RNA
<213> ORGANISM: Murine

<400> SEQUENCE: 4
uuaaugcuaa uugugauagg ggu                                           23

<210> SEQ ID NO 5
<211> LENGTH: 22
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(22)
<223> OTHER INFORMATION: phosphorothioate internucleotide bonds
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (19)..(22)
<223> OTHER INFORMATION: LNA

<400> SEQUENCE: 5
cccctatcac gattagcatt aa                                            22

<210> SEQ ID NO 6
<211> LENGTH: 22
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(22)
<223> OTHER INFORMATION: phosphorothioate internucleotide bonds
<220> FEATURE:
<221> NAME/KEY: misc_feature
<222> LOCATION: (7)..(14)
<223> OTHER INFORMATION: LNA

<400> SEQUENCE: 6
cccctatcac gattagcatt aa                                            22

<210> SEQ ID NO 7
<211> LENGTH: 22
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(22)
<223> OTHER INFORMATION: phosphorothioate internucleotide bonds
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
```

```
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA
<220> FEATURE:
<221> NAME/KEY: misc_feature
<222> LOCATION: (17)..(17)
<223> OTHER INFORMATION: LNA
<220> FEATURE:
<221> NAME/KEY: misc_feature
<222> LOCATION: (20)..(20)
<223> OTHER INFORMATION: LNA

<400> SEQUENCE: 7
cccctatcac gattagcatt aa                                              22

<210> SEQ ID NO 8
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleotide bonds
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 8
tcacgattag catta                                                      15

<210> SEQ ID NO 9
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleotide bonds
```

```
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(7)
<223> OTHER INFORMATION: LNA
<220> FEATURE:
<221> NAME/KEY: misc_feature
<222> LOCATION: (10)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 9
tcacgattag catta                                                      15

<210> SEQ ID NO 10
<211> LENGTH: 13
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(13)
<223> OTHER INFORMATION: phosphorothioate internucleotide bonds
<220> FEATURE:
<221> NAME/KEY: misc_feature
<222> LOCATION: (1)..(5)
<223> OTHER INFORMATION: LNA
<220> FEATURE:
<221> NAME/KEY: misc_feature
<222> LOCATION: (7)..(10)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 10
acgattagca tta                                                        13

<210> SEQ ID NO 11
<211> LENGTH: 11
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(11)
<223> OTHER INFORMATION: phosphorothioate internucleotide bonds
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (5)..(7)
<223> OTHER INFORMATION: LNA
<220> FEATURE:
<221> NAME/KEY: misc_feature
<222> LOCATION: (9)..(11)
<223> OTHER INFORMATION: LNA

<400> SEQUENCE: 11
```
gattagcatt a                                                          11

<210> SEQ ID NO 12
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleotide bonds
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (2)..(2)
<223> OTHER INFORMATION: 2'OME
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (4)..(5)
<223> OTHER INFORMATION: 2'OME
<220> FEATURE:
<221> NAME/KEY: misc_feature
<222> LOCATION: (6)..(8)
<223> OTHER INFORMATION: LNA
<220> FEATURE:
<221> NAME/KEY: misc_feature
<222> LOCATION: (9)..(9)
<223> OTHER INFORMATION: 2'OME
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (11)..(11)
<223> OTHER INFORMATION: 2'OME
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (13)..(13)
<223> OTHER INFORMATION: 2'OME
<220> FEATURE:
<221> NAME/KEY: misc_feature
<222> LOCATION: (14)..(15)
<223> OTHER INFORMATION: LNA

<400> SEQUENCE: 12
tcacgattag catta                                                      15

<210> SEQ ID NO 13
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleotide bonds
<220> FEATURE:
<221> NAME/KEY: misc_feature
<222> LOCATION: (1)..(1)
<223> OTHER INFORMATION: LNA

```
<220> FEATURE:
<221> NAME/KEY: misc_feature
<222> LOCATION: (2)..(2)
<223> OTHER INFORMATION: 2'Fluoro DNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (4)..(5)
<223> OTHER INFORMATION: 2'Fluoro DNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (8)..(9)
<223> OTHER INFORMATION: 2'Fluoro DNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (11)..(11)
<223> OTHER INFORMATION: 2'Fluoro DNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (13)..(13)
<223> OTHER INFORMATION: 2'Fluoro DNA
<220> FEATURE:
<221> NAME/KEY: misc_feature
<222> LOCATION: (14)..(15)
<223> OTHER INFORMATION: LNA

<400> SEQUENCE: 13
tcacgattag catta                                                  15

<210> SEQ ID NO 14
<211> LENGTH: 22
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(22)
<223> OTHER INFORMATION: phosphorothioate internucleotide bonds
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
```

```
<223> OTHER INFORMATION: LNA
<220> FEATURE:
<221> NAME/KEY: misc_feature
<222> LOCATION: (14)..(14)
<223> OTHER INFORMATION: LNA
<220> FEATURE:
<221> NAME/KEY: misc_feature
<222> LOCATION: (16)..(16)
<223> OTHER INFORMATION: LNA
<220> FEATURE:
<221> NAME/KEY: misc_feature
<222> LOCATION: (18)..(18)
<223> OTHER INFORMATION: LNA
<220> FEATURE:
<221> NAME/KEY: misc_feature
<222> LOCATION: (20)..(20)
<223> OTHER INFORMATION: LNA

<400> SEQUENCE: 14
cccctatcac gattagcatt aa                                              22

<210> SEQ ID NO 15
<211> LENGTH: 16
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(16)
<223> OTHER INFORMATION: phosphorothioate internucleotide bonds
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 15
tcacgattag cattaa                                                     16

<210> SEQ ID NO 16
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleotide bonds
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
```

```
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 16
tcacgattag catta                                                      15

<210> SEQ ID NO 17
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleoside bonds
<220> FEATURE:
<221> NAME/KEY: misc_feature
<222> LOCATION: (1)..(15)
<223> OTHER INFORMATION: phosphorothioate internucleotide bonds
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(7)
<223> OTHER INFORMATION: LNA
<220> FEATURE:
<221> NAME/KEY: misc_feature
<222> LOCATION: (10)..(12)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 17
tcacaattag catta                                                      15

<210> SEQ ID NO 18
<211> LENGTH: 15
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(15)
<223> OTHER INFORMATION: phosphorothioate internucleotide bonds
<220> FEATURE:
<221> NAME/KEY: misc_feature
<222> LOCATION: (1)..(1)
```

```
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(7)
<223> OTHER INFORMATION: LNA
<220> FEATURE:
<221> NAME/KEY: misc_feature
<222> LOCATION: (10)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 18
tcaacattag actta                                                    15

<210> SEQ ID NO 19
<211> LENGTH: 10
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(10)
<223> OTHER INFORMATION: phosphorothioate internucleotide bonds
<220> FEATURE:
<221> NAME/KEY: misc_feature
<222> LOCATION: (1)..(10)
<223> OTHER INFORMATION: LNA

<400> SEQUENCE: 19
attagcatta                                                          10

<210> SEQ ID NO 20
<211> LENGTH: 9
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(9)
<223> OTHER INFORMATION: phosphorothioate internucleotide bonds
<220> FEATURE:
<221> NAME/KEY: misc_feature
<222> LOCATION: (1)..(9)
<223> OTHER INFORMATION: LNA

<400> SEQUENCE: 20 ttagcatta                                                            9

<210> SEQ ID NO 21
<211> LENGTH: 8
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(8)
<223> OTHER INFORMATION: phosphorothioate internucleotide bonds
<220> FEATURE:
<221> NAME/KEY: misc_feature
<222> LOCATION: (1)..(8)
<223> OTHER INFORMATION: LNA
```

```
<400> SEQUENCE: 21 tagcatta                                                               8

<210> SEQ ID NO 22
<211> LENGTH: 7
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(7)
<223> OTHER INFORMATION: phosphorothioate internucleotide bonds
<220> FEATURE:
<221> NAME/KEY: misc_feature
<222> LOCATION: (1)..(7)
<223> OTHER INFORMATION: LNA

<400> SEQUENCE: 22 agcatta                                                                7

<210> SEQ ID NO 23
<211> LENGTH: 9
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(9)
<223> OTHER INFORMATION: phosphorothioate internucleoside bonds
<220> FEATURE:
<221> NAME/KEY: misc_feature
<222> LOCATION: (1)..(9)
<223> OTHER INFORMATION: LNA

<400> SEQUENCE: 23 tatgtagga                                                              9

<210> SEQ ID NO 24
<211> LENGTH: 8
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(8)
<223> OTHER INFORMATION: phosphorothioate internucleotide bonds
<220> FEATURE:
<221> NAME/KEY: misc_feature
<222> LOCATION: (1)..(8)
<223> OTHER INFORMATION: LNA

<400> SEQUENCE: 24 atgtagga                                                               8

<210> SEQ ID NO 25
<211> LENGTH: 7
<212> TYPE: DNA
<213> ORGANISM: Artificial
<220> FEATURE:
<223> OTHER INFORMATION: nucleotide motif sequence e.g. DNA/LNA oligomer
      sequences
<220> FEATURE:
<221> NAME/KEY: misc_feature
<222> LOCATION: (1)..(7)
<223> OTHER INFORMATION: phosphorothioate internucleotide bonds
```

```
<220> FEATURE:
<221> NAME/KEY: misc_feature
<222> LOCATION: (1)..(7)
<223> OTHER INFORMATION: LNA

<400> SEQUENCE: 25 tgtagga                                                                   7

<210> SEQ ID NO 26
<211> LENGTH: 29
<212> TYPE: DNA
<213> ORGANISM: Mus musculus

<400> SEQUENCE: 26
tcgagcccct atcacaatta gcattaagc                                          29

<210> SEQ ID NO 27
<211> LENGTH: 29
<212> TYPE: DNA
<213> ORGANISM: Mus musculus

<400> SEQUENCE: 27
ggccgcttaa tgctaattgt gatagggggc                                         29

<210> SEQ ID NO 28
<211> LENGTH: 37
<212> TYPE: RNA
<213> ORGANISM: Homo sapiens

<400> SEQUENCE: 28
uuuuccguuu caagcauuaa gaacacuuuu aauaaac                                 37

<210> SEQ ID NO 29
<211> LENGTH: 41
<212> TYPE: RNA
<213> ORGANISM: Mus musculus

<400> SEQUENCE: 29
uuuuccguuu cgagcauuaa agugaagaca uuuuaauaaa c                            41

<210> SEQ ID NO 30
<211> LENGTH: 41
<212> TYPE: RNA
<213> ORGANISM: Rattus norvegicus

<400> SEQUENCE: 30
uuuuccguuu cgagcauuaa agugaagaca uuuuaauaaa c                            41

<210> SEQ ID NO 31
<211> LENGTH: 37
<212> TYPE: RNA
<213> ORGANISM: Canis familiaris

<400> SEQUENCE: 31
uuuuccguuu caagcauuaa gaacacuuuu aauaaac                                 37

<210> SEQ ID NO 32
<211> LENGTH: 38
<212> TYPE: RNA
<213> ORGANISM: Gallus gallus

<400> SEQUENCE: 32
ugcuacauuu gaagcauuaa ugaacgauuu uaauaaac                                38
```

-continued

```
<210> SEQ ID NO 33
<211> LENGTH: 22
<212> TYPE: RNA
<213> ORGANISM: Homo sapiens

<400> SEQUENCE: 33
ccccuaucac gauuagcauu aa                                              22

<210> SEQ ID NO 34
<211> LENGTH: 29
<212> TYPE: DNA
<213> ORGANISM: Homo sapiens

<400> SEQUENCE: 34
tcgagcccct atcacgatta gcattaagc                                       29

<210> SEQ ID NO 35
<211> LENGTH: 28
<212> TYPE: DNA
<213> ORGANISM: Homo sapiens

<400> SEQUENCE: 35
ggccgcttaa tgctaatcgt gatagggg                                        28

<210> SEQ ID NO 36
<211> LENGTH: 32
<212> TYPE: DNA
<213> ORGANISM: Homo sapiens

<400> SEQUENCE: 36
aaaaaactcg agaaaacttt ggcactgggg ca                                   32

<210> SEQ ID NO 37
<211> LENGTH: 35
<212> TYPE: DNA
<213> ORGANISM: Homo sapiens

<400> SEQUENCE: 37
aaaaaagcgg ccgcggcttt gtaaccattc tcaaa                                35
```